(12) United States Patent
Alizadeh et al.

(10) Patent No.: US 10,775,332 B2
(45) Date of Patent: Sep. 15, 2020

(54) ELECTRICAL METHODS AND SYSTEMS FOR CONCRETE TESTING

(71) Applicant: GIATEC SCIENTIFIC INC., Nepean (CA)

(72) Inventors: Rouhollah Alizadeh, Gloucester (CA); Pouria Ghods, Gloucester (CA); Amir Hosein Ghods, Toronto (CA); Mustafa Salehi, Ottawa (CA)

(73) Assignee: Giatec Scientific Ltd., Ottawa, Ontario (CA)

( * ) Notice: Subject to any disclaimer, the term of this patent is extended or adjusted under 35 U.S.C. 154(b) by 5 days.

(21) Appl. No.: 15/311,055

(22) PCT Filed: May 13, 2015

(86) PCT No.: PCT/CA2015/000314
§ 371 (c)(1),
(2) Date: Nov. 14, 2016

(87) PCT Pub. No.: WO2015/172231
PCT Pub. Date: Nov. 19, 2015

(65) Prior Publication Data
US 2017/0108456 A1    Apr. 20, 2017

Related U.S. Application Data

(60) Provisional application No. 61/992,364, filed on May 13, 2014.

(51) Int. Cl.
*G01N 27/02*    (2006.01)
*G01N 33/38*    (2006.01)
(Continued)

(52) U.S. Cl.
CPC ....... *G01N 27/021* (2013.01); *C04B 40/0007* (2013.01); *C04B 40/0096* (2013.01);
(Continued)

(58) Field of Classification Search
None
See application file for complete search history.

(56) References Cited

U.S. PATENT DOCUMENTS 3,468,001 A    9/1969    Bodine
6,396,265 B1    5/2002    Shtakelberg
(Continued)

FOREIGN PATENT DOCUMENTS

WO    2011130637 A2    10/2011
WO    2015172231 A1    11/2015

OTHER PUBLICATIONS

Brameshuber, et al., "Non-Destructive Determination of Water-Content in the Concrete Cover using the Multiring Electrode", Int. Symp. Non-Destructive Testing in Civil Engineering, vol. 8, No. 10, pp. 1-4, Sep. 2003.
(Continued)

*Primary Examiner* — Douglas X Rodriguez
(74) *Attorney, Agent, or Firm* — Rosenberg, Klein & Lee

(57) ABSTRACT

Concrete can be one of the most durable building materials and structures made of concrete can have a long service life. Consumption is projected to reach approximately 40 billion tons in 2017. Despite this the testing of concrete at all stages of its life cycle is still in its early stages although testing for corrosion is well established. Further many of the tests today are time consuming, expensive, and provide results only after it has been poured and set. Embodiments of the invention provide concrete suppliers, construction companies, regulators, architects, and others with rapid testing and performance data regarding the cure, performance, corrosion of concrete at different points in its life cycle based upon a simple electrical tests that remove subjectivity, allow for rapid assessment, are integrable to the construction process, and provided full life cycle assessment. Wireless
(Continued)

sensors can be embedded from initial loading through post-cure into service life.

27 Claims, 25 Drawing Sheets

(51) Int. Cl.
*C04B 40/00* (2006.01)
*G01M 5/00* (2006.01)
*G01R 27/16* (2006.01)
*C04B 111/00* (2006.01)
*C04B 111/92* (2006.01)

(52) U.S. Cl.
CPC ........ *G01M 5/0083* (2013.01); *G01N 33/383* (2013.01); *C04B 2111/00991* (2013.01); *C04B 2111/92* (2013.01); *G01R 27/16* (2013.01)

(56) References Cited

U.S. PATENT DOCUMENTS

| | | | |
|---|---|---|---|
| 7,181,978 B2 | 2/2007 | Shtakelberg | |
| 7,225,682 B2 | 6/2007 | Shtakelberg | |
| 7,289,916 B2 * | 10/2007 | Drnevich | ................ C04B 28/02 |
| | | | 702/138 |
| 8,610,444 B2 | 12/2013 | Shtakelberg | |
| 2002/0057097 A1 * | 5/2002 | Kelly | .................... G01N 17/006 |
| | | | 324/700 |
| 2002/0154029 A1 | 10/2002 | Watters | |
| 2004/0153270 A1 * | 8/2004 | Yamashita | ........... G01N 33/383 |
| | | | 702/81 |
| 2005/0210995 A1 | 9/2005 | Drnevich | |
| 2007/0090945 A1 | 4/2007 | Hoogenboom | |
| 2014/0062489 A1 | 3/2014 | Pindiprolu | |
| 2016/0018383 A1 * | 1/2016 | Radjy | ....................... B28C 7/02 |
| | | | 73/53.01 |
| 2016/0061751 A1 * | 3/2016 | Carr | ..................... G01N 27/026 |
| | | | 324/637 |

OTHER PUBLICATIONS

Stackelberg, et al., "Principles of Monitoring Hardening and Strengthening of Shotcrete", J. Chinese Ceramic Society, vol. 42, No. 5, pp. 568-573, May 2014.

Stackelberg, et al., "Physical Nature if Linear Correlations "Strength-Resistivity" by Control Hardening Cement-Concrete Compositions", Building Materials, vol. 3, pp. 118-122, 2010.

McCarter, et al., "Dependence of Electrical Impedance of Cement-Based Materials on their Moisture Condition", J. Physics D, Applied Physics, vol. 22, No. 11, pp. 1773-1776, Institute of Physics Publishing, 1989.

* cited by examiner

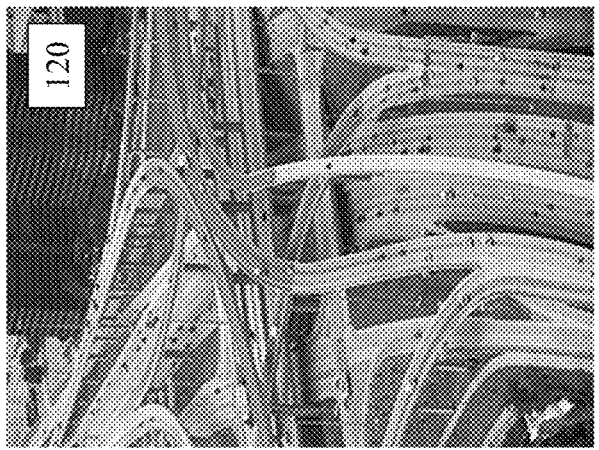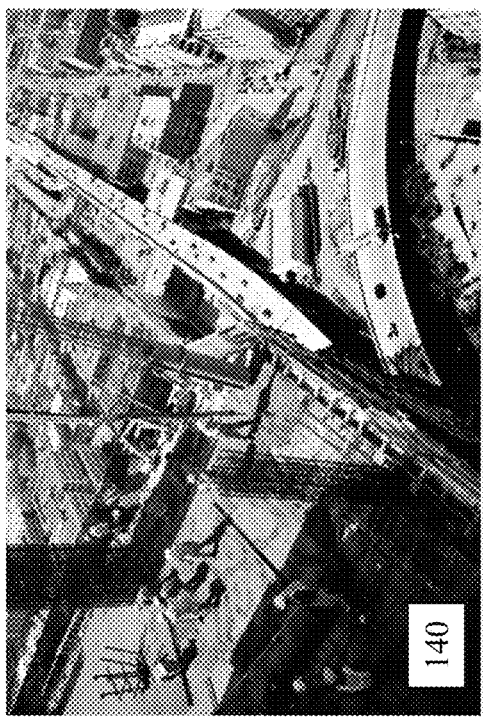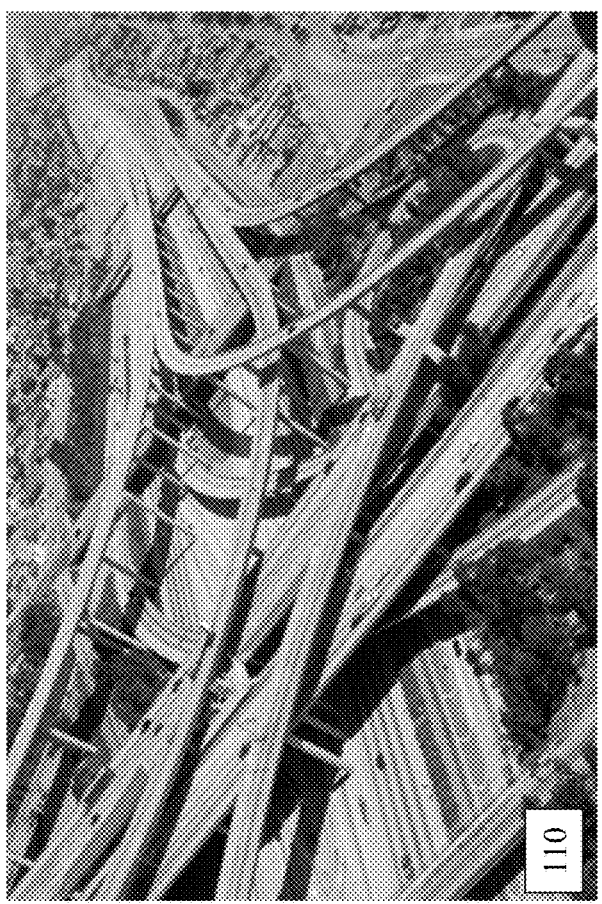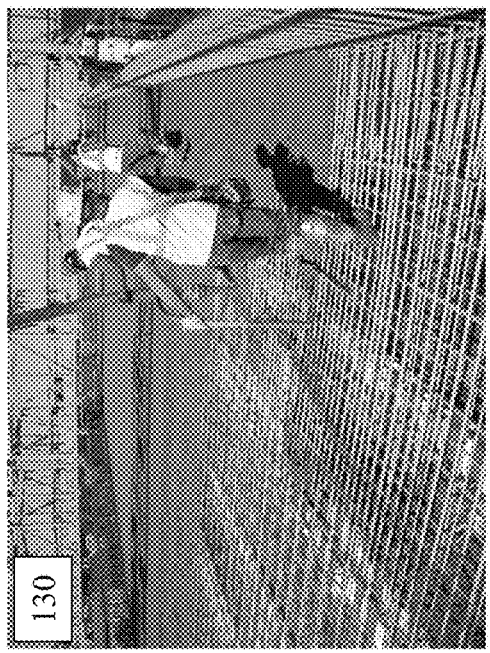
Figure 1

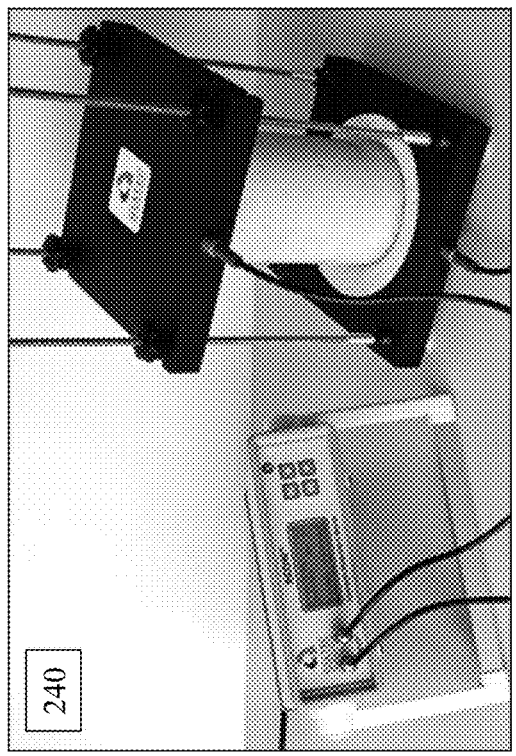
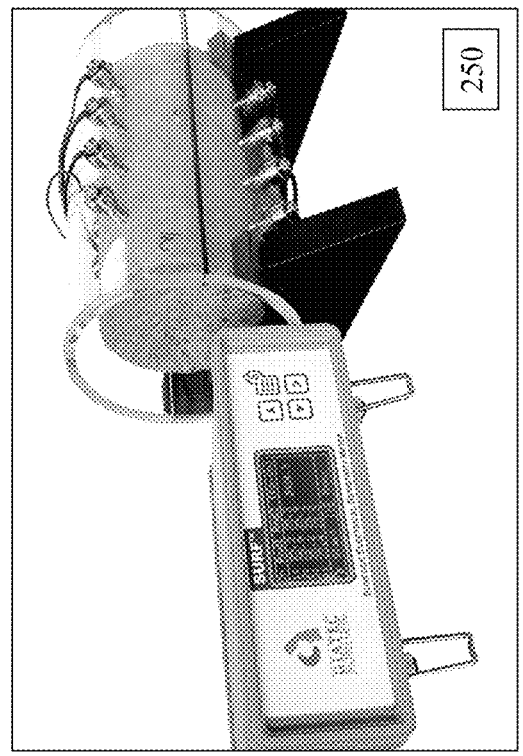
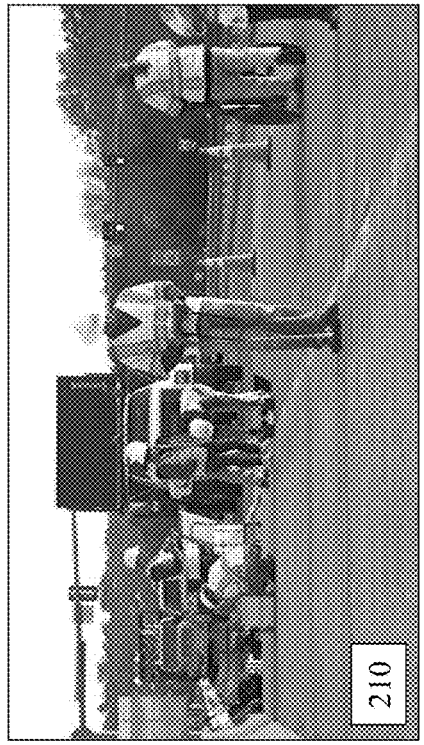
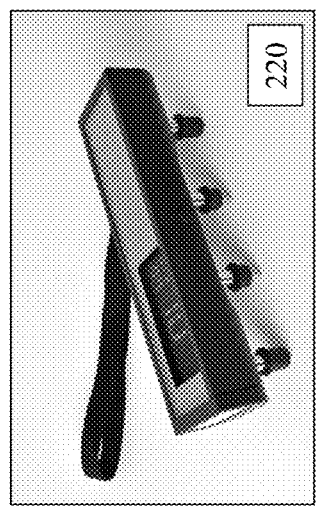
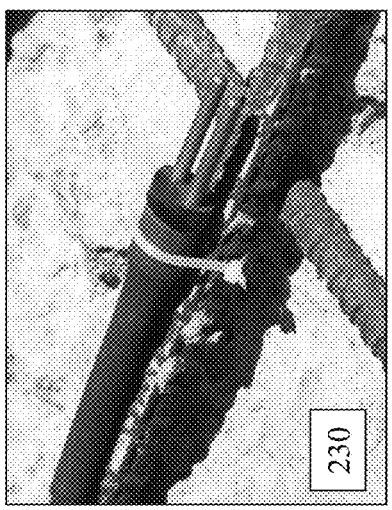
Figure 2 PRIOR ART

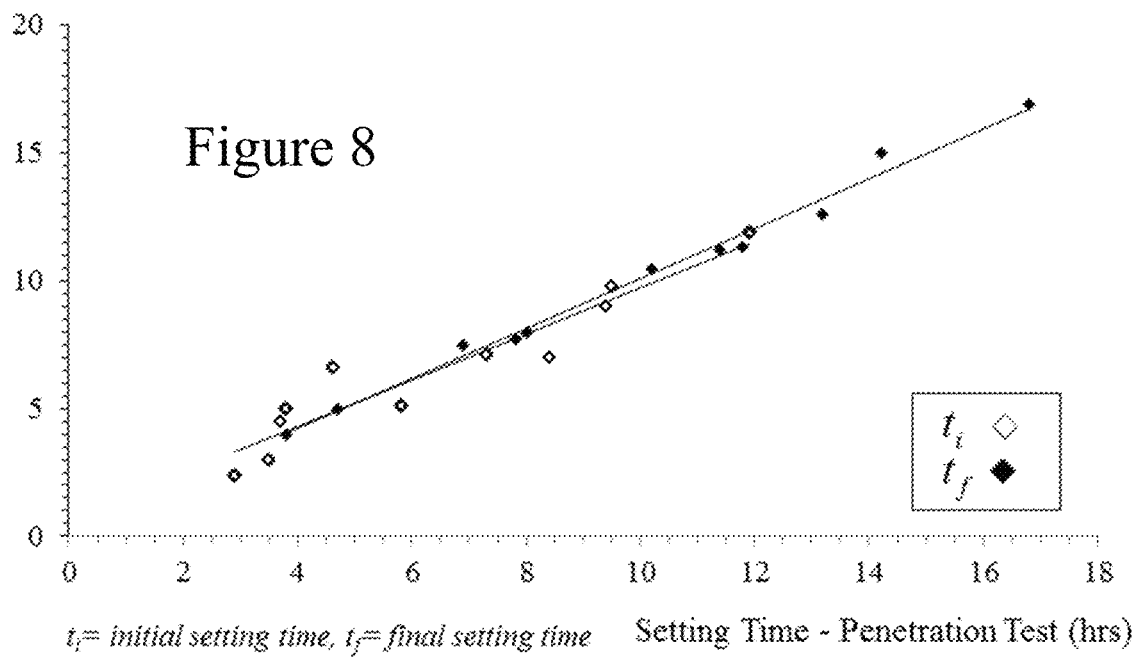
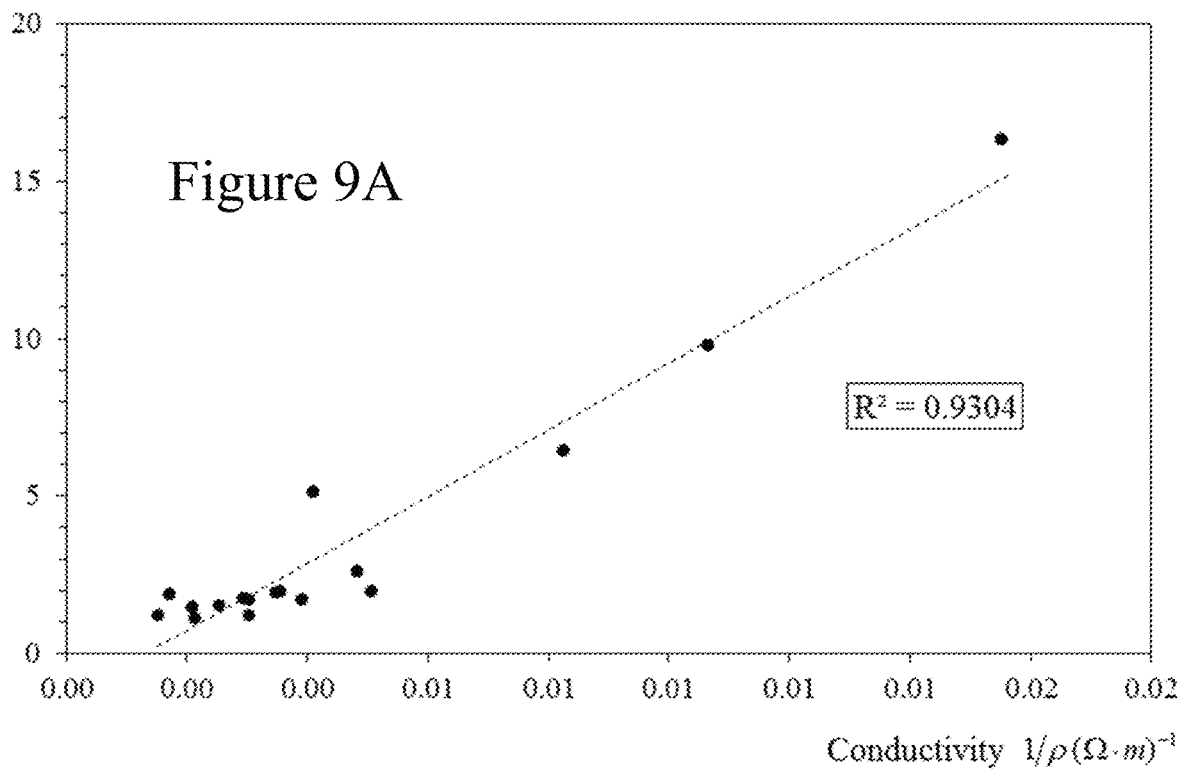

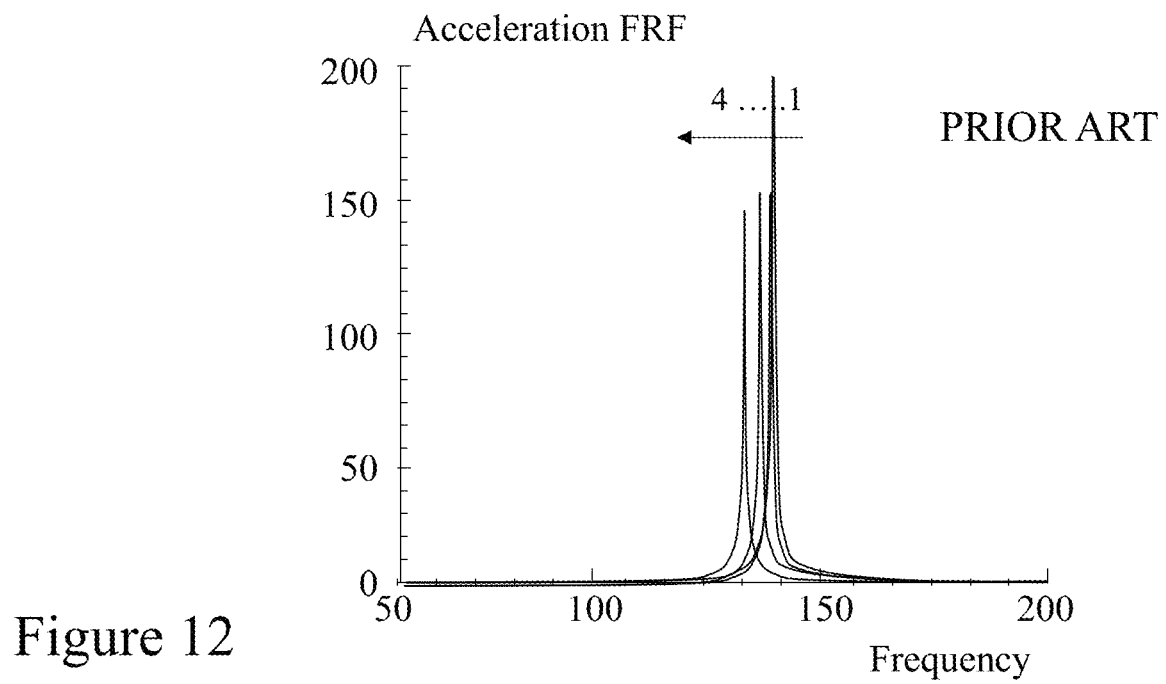
Figure 12
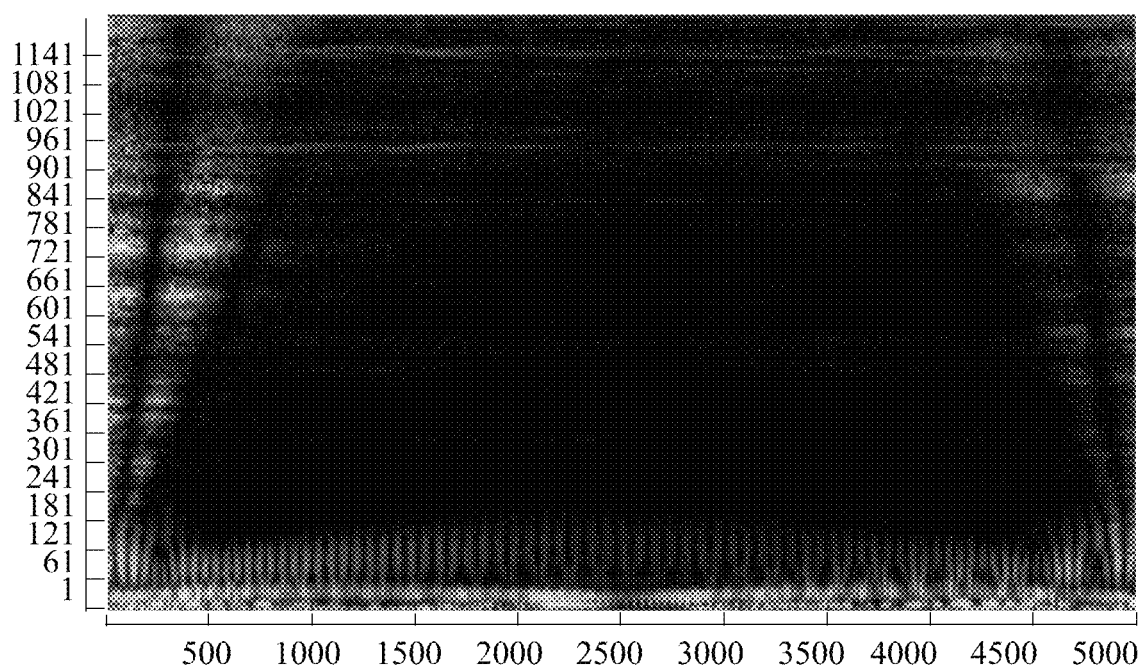
Figure 13   x(t)/0.002 x(t)/0.002

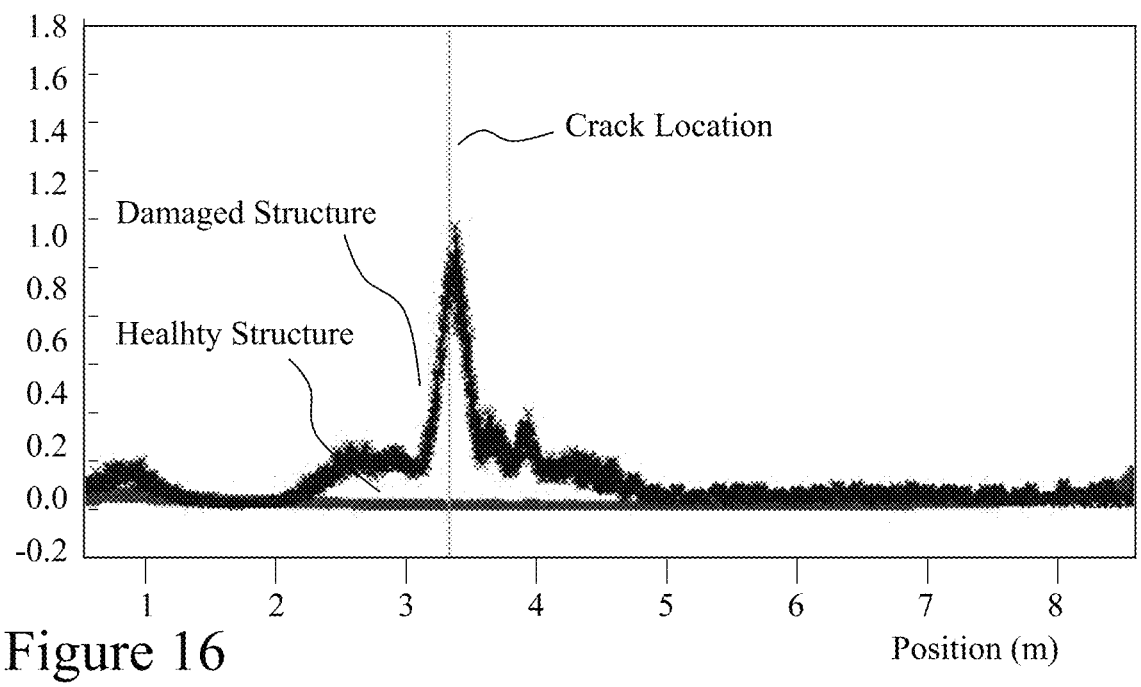
Figure 16
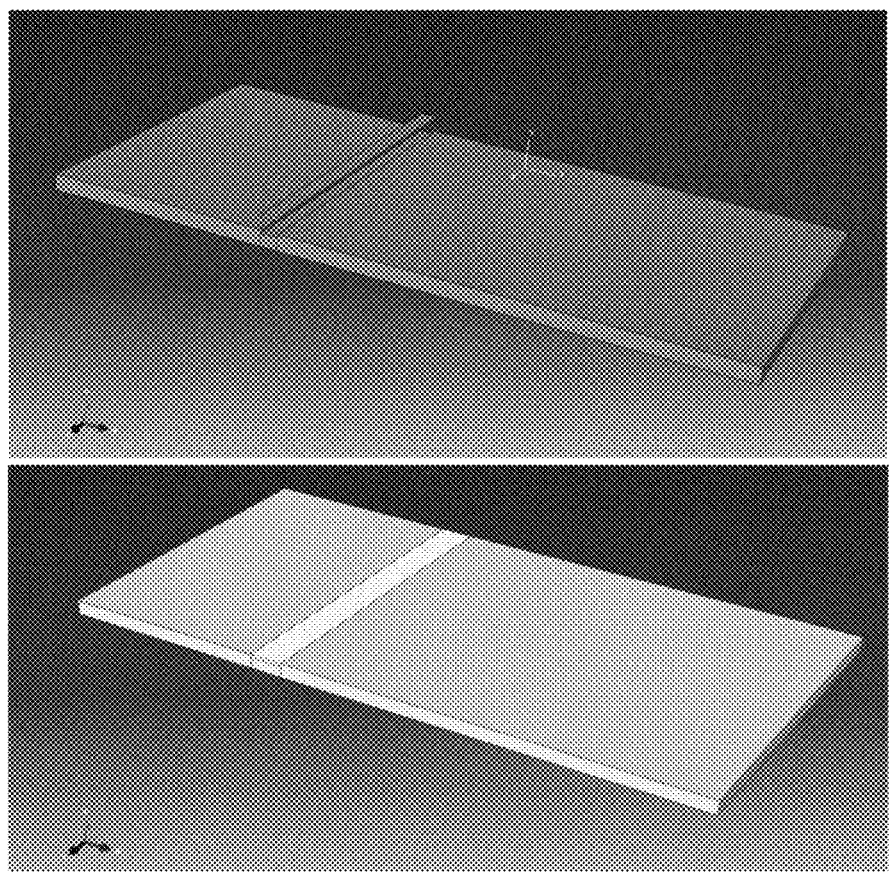
Figure 17
Figure 18

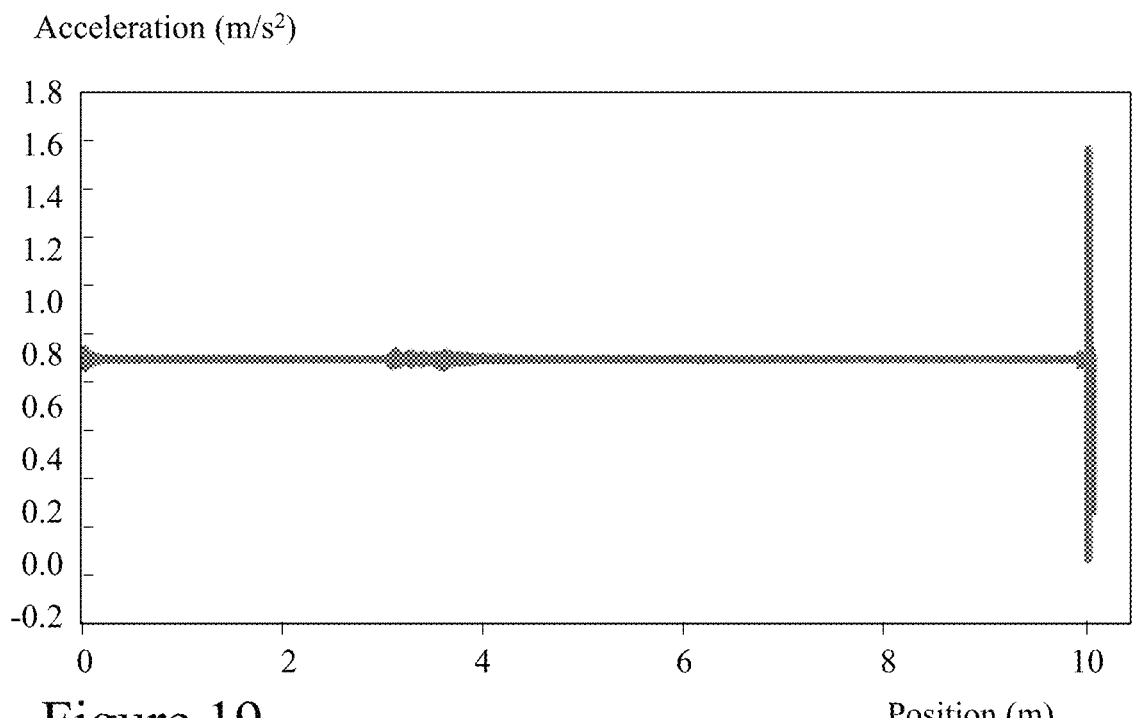
Figure 19
Figure 20
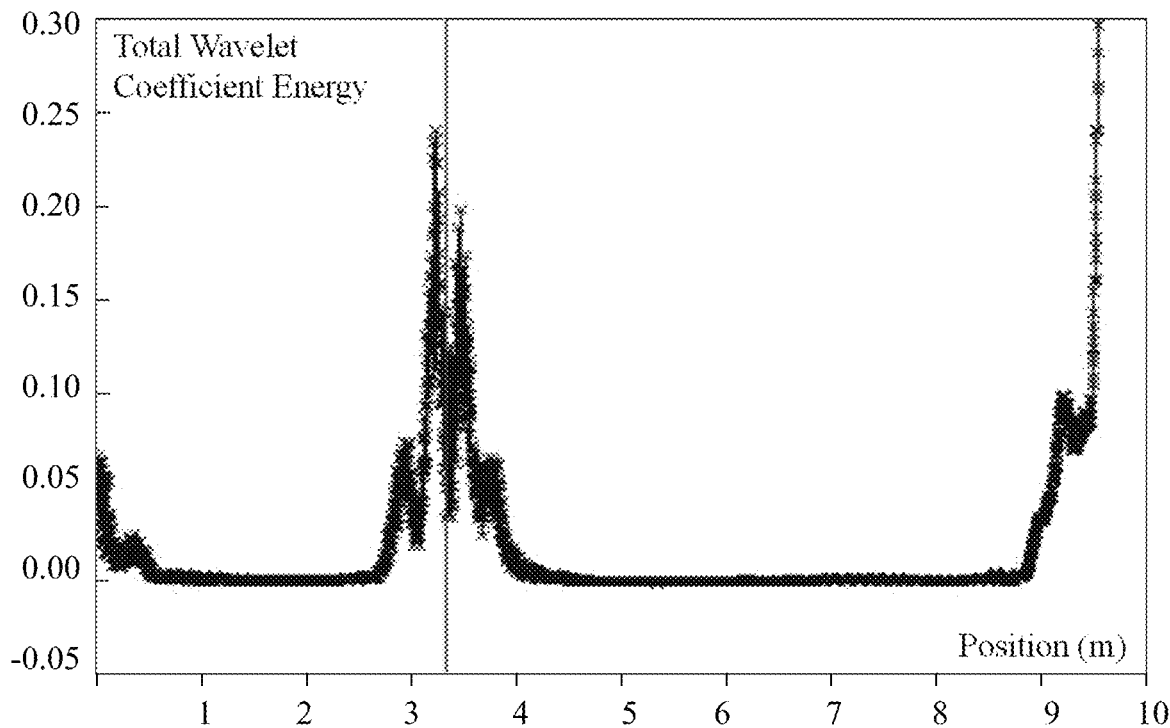

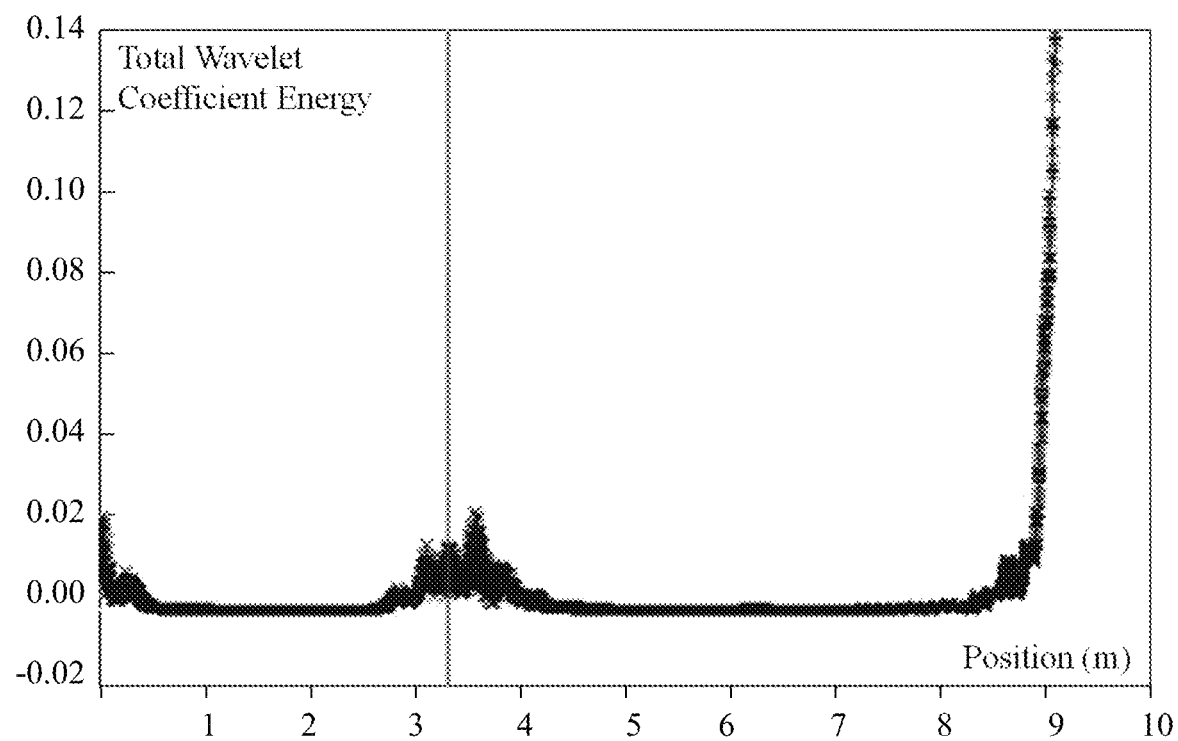
Figure 21
Figure 22
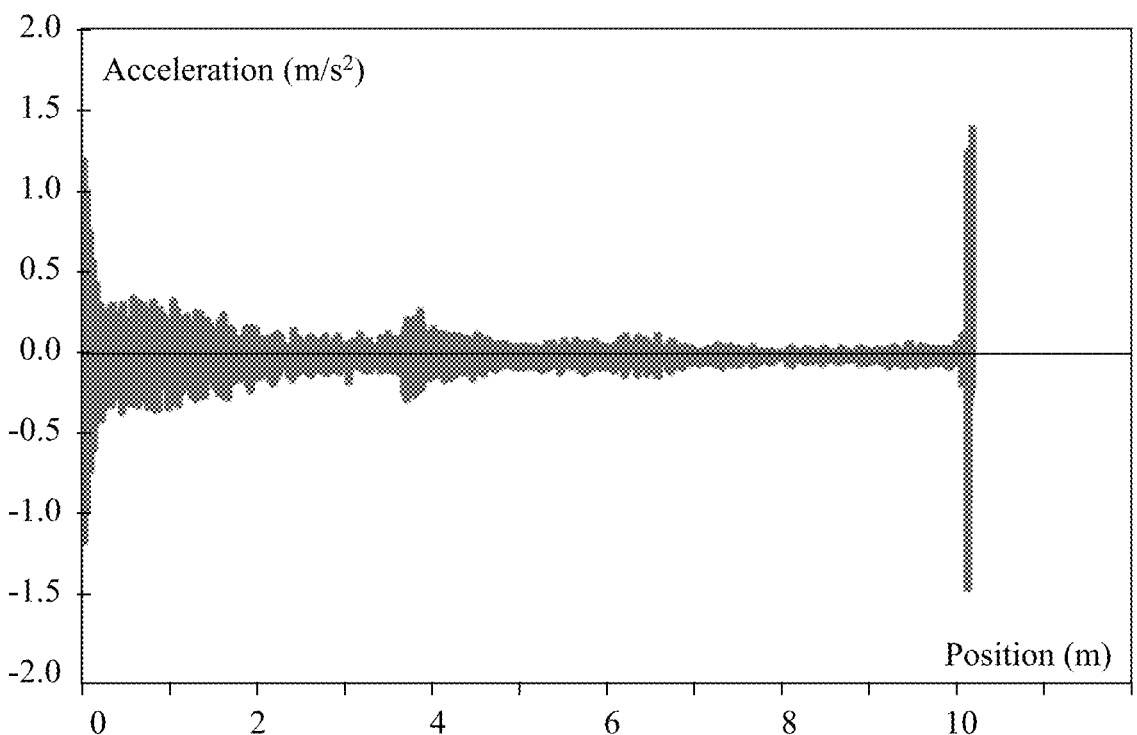

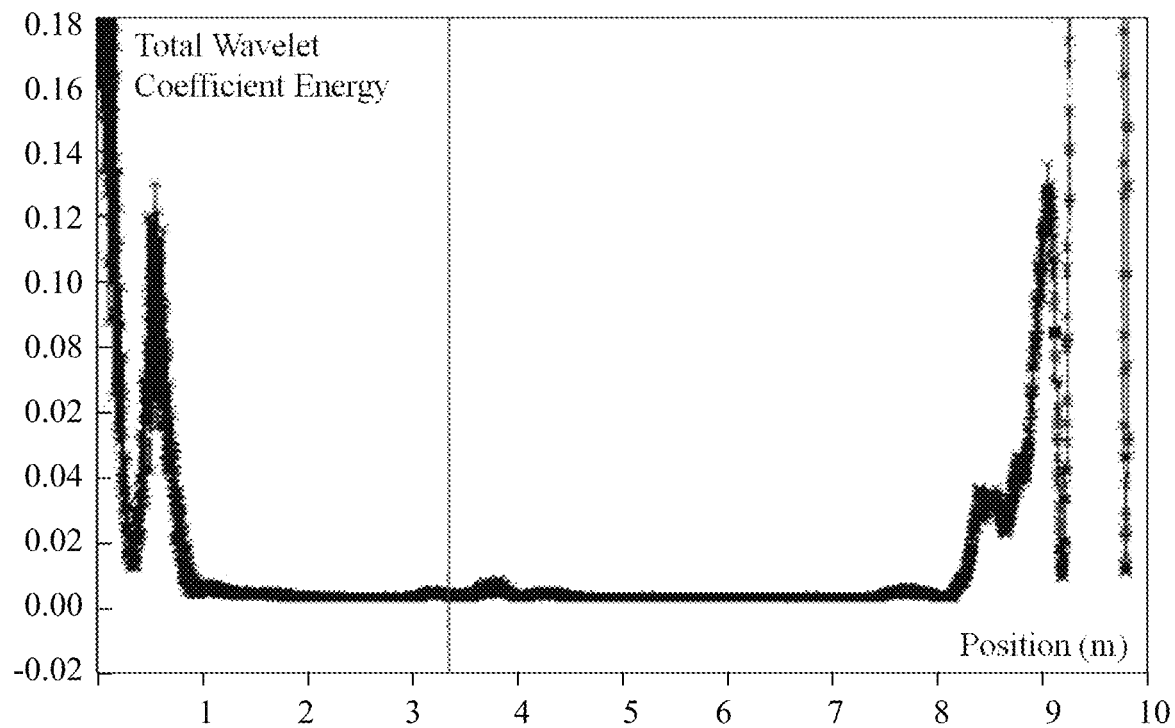
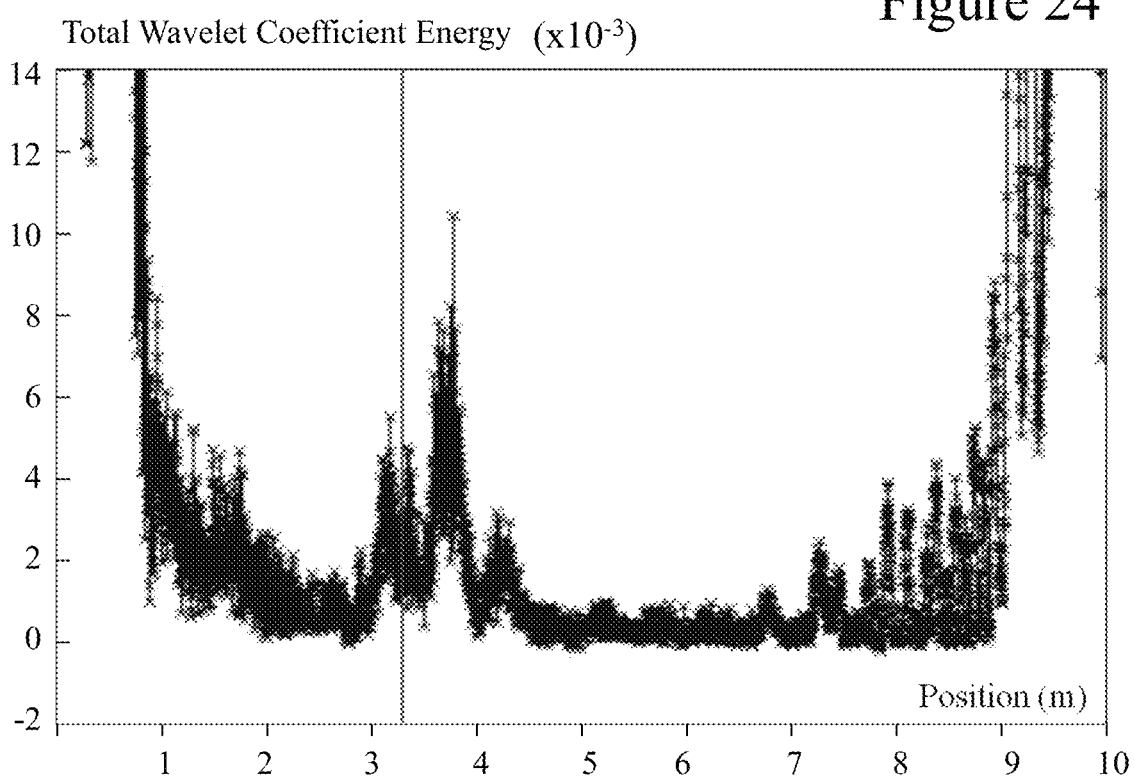
Figure 23
Figure 24

ELECTRICAL METHODS AND SYSTEMS FOR CONCRETE TESTING

CROSS-REFERENCE TO RELATED APPLICATIONS

This patent application claims the benefit of Patent Cooperation Treaty Application PCT/CA2015/000,314 entitled "Electrical Methods and Systems for Concrete Testing" filed May 13, 2015, which itself claims the benefit of U.S. Provisional Patent Application 61/992,364 filed May 13, 2014 entitled "Electrical Methods and Systems for Concrete Testing" filed May 13, 2014, the entire contents of both being included by reference.

FIELD OF THE INVENTION

The present invention relates to concrete testing and concrete structure characterization, more particularly to electrical methods and systems for establishing cured concrete performance from measurements of wet concrete and automated methods and systems for periodic and/or continuous characterization of concrete structures.

BACKGROUND OF THE INVENTION

Concrete can be one of the most durable building materials and structures made of concrete can have a long service life. Concrete is a composite construction material composed primarily of aggregate, cement, and water. It provides superior fire resistance, compared with wooden construction and can gain strength over time. Further, as it is used as liquid that subsequently hardens it can be formed into complex geometries and may poured either directly into formworks at the construction sites (so called ready mix concrete) or employed remotely to pre-build concrete elements and structures. Overall concrete is the most widely used construction material in the world with an annual consumption estimated at approximately 30 billion tons in 2006, compared to 2 billion in 1950. During the next 5 years concrete consumption is estimated to grow with a Compound Annual Growth Rate (CAGR) between 6% and 9% according to market forecasts of cement and concrete admixtures globally over the period 2012 to 2017 such that the 30 billion ton consumption will increase to approximately 40 billion tons.

Concrete is widely used for making architectural structures, foundations, brick/block walls, pavements, bridges/overpasses, motorways/roads, runways, parking structures, dams, pools/reservoirs, pipes, footings for gates, fences and poles and even boats. Reinforced concrete, pre-stressed concrete and precast concrete are the most widely used types of concrete functional extensions. Concrete is strong in compression, as the aggregate efficiently carries the compression load. However, it is weak in tension as the cement holding the aggregate in place can crack, allowing the structure to fail. Reinforced concrete solves these problems by adding steel reinforcing bars, steel fibers, glass fiber, or plastic fiber to carry tensile loads. Thereafter the concrete is reinforced to withstand the tensile loads upon it. Due to their low cost and wide availability steel reinforcing bar (commonly referred to as rebar) has been the dominant reinforcing material for the past 50 years. However, these steel rebars may corrode whereby the oxidation products (rust) expand and tend to flake, thereby cracking the concrete and reducing the bonding between the rebar and the concrete. Such corrosion may arise from several sources including carbonation when the surface of concrete is exposed to high concentration of carbon dioxide or chlorides, such as when the concrete structure is in contact with a chloride-contaminated environment such as arises with de-icing salts and marine environment.

Just as the exploitation of concrete increased over the past 50 years then so have the requirements on it as engineering structures continue to push new boundaries of higher buildings, longer bridges, larger dams, artificial islands etc. Further disasters with poor concrete etc. have led to stricter regulation and compliance requirements. Accordingly, today the concrete industry faces competing demands for faster construction, shorter durations of formwork use, cost reductions whilst ensuring safety and quality are met or exceeded. As such testing techniques for concrete have evolved and will continue to evolve to meet these requirements. However, many of these techniques require samples be taken, full extended curing of the concrete performed, or simple mechanical tests be performed on site with the concrete being delivered.

However, it would be beneficial to provide concrete suppliers, construction companies, regulators, architects, and others requiring data regarding the cure, performance, corrosion of concrete at different points in its life cycle with a series of simple electrical tests that removed subjectivity, allowed for rapid assessment, were integrable to the construction process, and provided full life cycle assessment.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to address limitations within the prior art relating to concrete testing and concrete structure characterization, more particularly to electrical methods and systems for establishing cured concrete performance from measurements of wet concrete and automated methods and systems for periodic and/or continuous characterization of concrete structures.

In accordance with an embodiment of the invention there is provided a method comprising performing an electrical impedance measurement upon concrete, and determining based upon at least the electrical impedance measurement a characteristic of the concrete.

In accordance with an embodiment of the invention there is provided a method comprising performing an electrical impedance measurement upon concrete, and determining based upon at least the electrical impedance measurement a characteristic of the concrete, wherein the electrical impedance measurement is adjusted in dependence upon the temperature at the time of the electrical impedance measurement, the adjustment comprising an activation energy established in dependence upon which characteristic of the concrete is being determined, the characteristic of the concrete being at least one of:

determination of the water to cement ratio of the concrete;
estimation of in-situ compressive strength of the concrete after pouring;
prediction of at least one of 7-day, 28-day and 56-day compressive strength of the concrete;
detection of at least one of the initial and final setting time of the concrete;

assessment of a transport properties of the concrete selected from the group comprising permeability, diffusivity and porosity;

is the presence of a crack within the concrete; and a change in the pore solution.

In accordance with an embodiment of the invention there is provided a method comprising:

performing an electrical impedance measurement upon wet concrete;

determining based upon at least the electrical impedance measurement a characteristic of the wet concrete; and communicating either the characteristic of the wet concrete or a change to be made to the wet concrete.

In accordance with an embodiment of the invention there is provided a method comprising:

performing an electrical impedance measurement upon wet concrete within a framework;

determining based upon at least the electrical impedance measurement a characteristic of the wet concrete; and adjusting the characteristics of a heating system at least one of attached to, in contact with, and forming part of the framework.

In accordance with an embodiment of the invention there is provided a method comprising:

performing electrical impedance measurements upon wet concrete as it is poured and/or dispensed;

transmitting the electrical impedance measurements to a remote server;

processing upon the remote server the electrical impedance measurements to determine a value for a characteristic of a plurality of characteristics of the wet concrete; and communicating the characteristic of the wet concrete to a predetermined enterprise based upon at least one of the characteristic of a plurality of characteristics of the wet concrete and the determined value.

In accordance with an embodiment of the invention there is provided a method comprising method of determining a location of damage within a structure through mathematical processing of accelerometer data.

In accordance with an embodiment of the invention there is provided a method comprising:

providing at least one accelerometer of a plurality of accelerometers attached to a structure;

exciting the structure in a predetermined manner;

receiving from the at least one accelerometer of the plurality of accelerometers data relating to acceleration of the structure during at least the excitation of the structure;

receiving excitation data relating to the excitation of the structure;

performing with a microprocessor a wavelet transformation process on the received data from the at least one accelerometer of the plurality of accelerometers in dependence upon at least the excitation data;

automatically with the microprocessor generating and storing in a non-volatile non-transitory memory at least one of a three-dimensional coefficient plot and a two-dimensional wavelet coefficient plot in dependence upon the output from the wavelet transformation process.

In accordance with an embodiment of the invention there is provided of establishing at least one of scale and distance relating to objects within an image by providing a plurality of optical pointers approximately collimated optical beams in predetermined spatial relationship to a camera capturing the image, capturing the image comprising the objects and the landing points of the plurality of optical beams, and processing the acquired image with a series of algorithms to determine the at least one of scale and distance.

In accordance with an embodiment of the invention there is provided a method of determining at least one of a corrosion state and a depth of a rebar within reinforced concrete comprising providing four probes inline in contact with the reinforced concrete, applying a DC voltage to the outer pair of probes, measuring the time evolving potential difference across the inner pair of probes, and determining the at least one of the corrosion state and the depth of the rebar within the reinforced concrete in dependence upon at least the measured time evolved potential difference.

In accordance with an embodiment of the invention there is provided a device comprising:

a shell comprising an outer surface, a hollow interior, and a pair of outer electrical contacts disposed on the outer surface and coupled to a pair of inner electrical contacts on the interior of the shell;

an electrical circuit disposed within the shell and comprising a battery, a wireless transceiver, a memory, and a microprocessor;

a measurement circuit coupled to the microprocessor disposed within the shell coupled to the pair of inner electrical contacts and providing a predetermined electrical measurement of a characteristic of the environment adjacent to the pair of outer electrical contacts.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached figures, wherein:

FIG. 1 depicts examples of concrete infrastructure that require characterization as well as rebar reinforced concrete;

FIG. 2 depicts surface electrical resistivity measurements and embedded resistance probes according to the prior art;

FIG. 8 depicts the comparison between setting times established by the ASTM 803 standard versus predictions from electrical resistivity measurements according to an embodiment of the invention;

FIG. 9A depicts the relationship between electrical conductivity and chloride diffusion coefficient of concrete for twenty concrete samples as measured according to an embodiment of the invention;

FIG. 12 depicts a graph produced by Wang according to the prior art showing the shift in natural frequency of a structure with varying levels of damage;

FIG. 13 depicts a 3D wavelet coefficient plot for a moving load moving across a 10 m long undamaged structure according to an embodiment of the invention;

FIG. 16 depicts 2D wavelet coefficient plot for damaged and undamaged structures for scales 300-900 according to an embodiment of the invention;

FIG. 17 depicts a 2-piece model for use within an ARAQUS simulation;

FIG. 18 depicts a 1-piece model for use within an ARAQUS simulation;

FIG. 19 depicts the acceleration response due to a moving load for a measurement point 6 m from damage using a 2-piece model according to an embodiment of the invention;

FIG. 20 depicts the 2D energy wavelet plot from the measurement point 6 m away from the damaged area derived from the acceleration data in FIG. 9 with a damaged area of width 0.25 m according to an embodiment of the invention;

FIG. 21 depicts the 2D energy wavelet plot from a measurement point 6 m away from a damaged area derived from acceleration data with a damaged area of width 0.50 m according to an embodiment of the invention;

FIG. 22 depicts acceleration response due to moving load from a measurement point 4 m from damage using a 1-piece model according to an embodiment of the invention;

FIGS. 23 to 25 respectively depict 2D wavelet energy plots for measurements points 6 m, 4 m and 2.25 m respectively away from a damaged region of width 0.25 m according to an embodiment of the invention;

DETAILED DESCRIPTION

Figure 3:
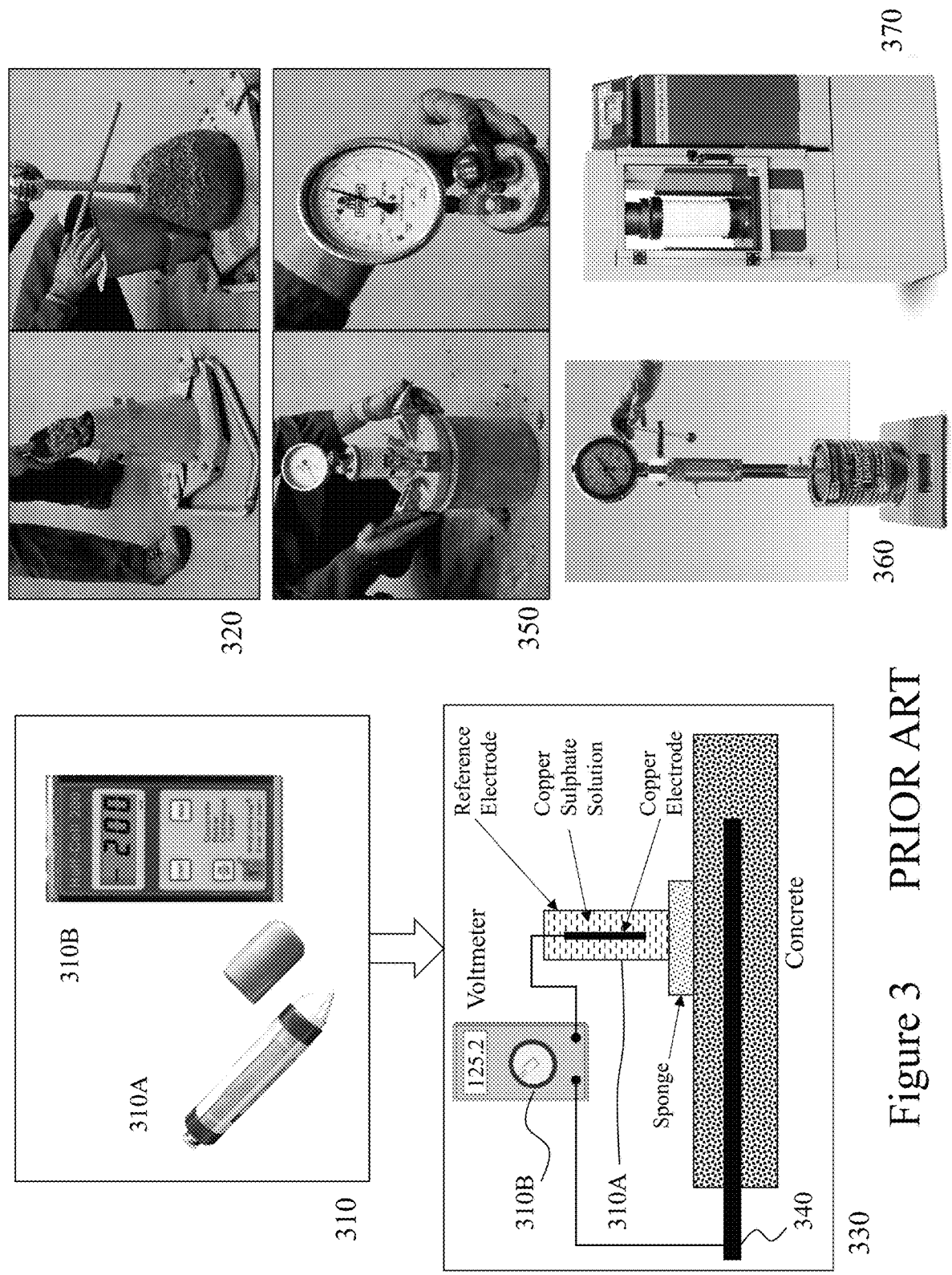
FIG. 3 depicts half-cell potential and surface resistivity measurements according to the prior art.
Figure 4:
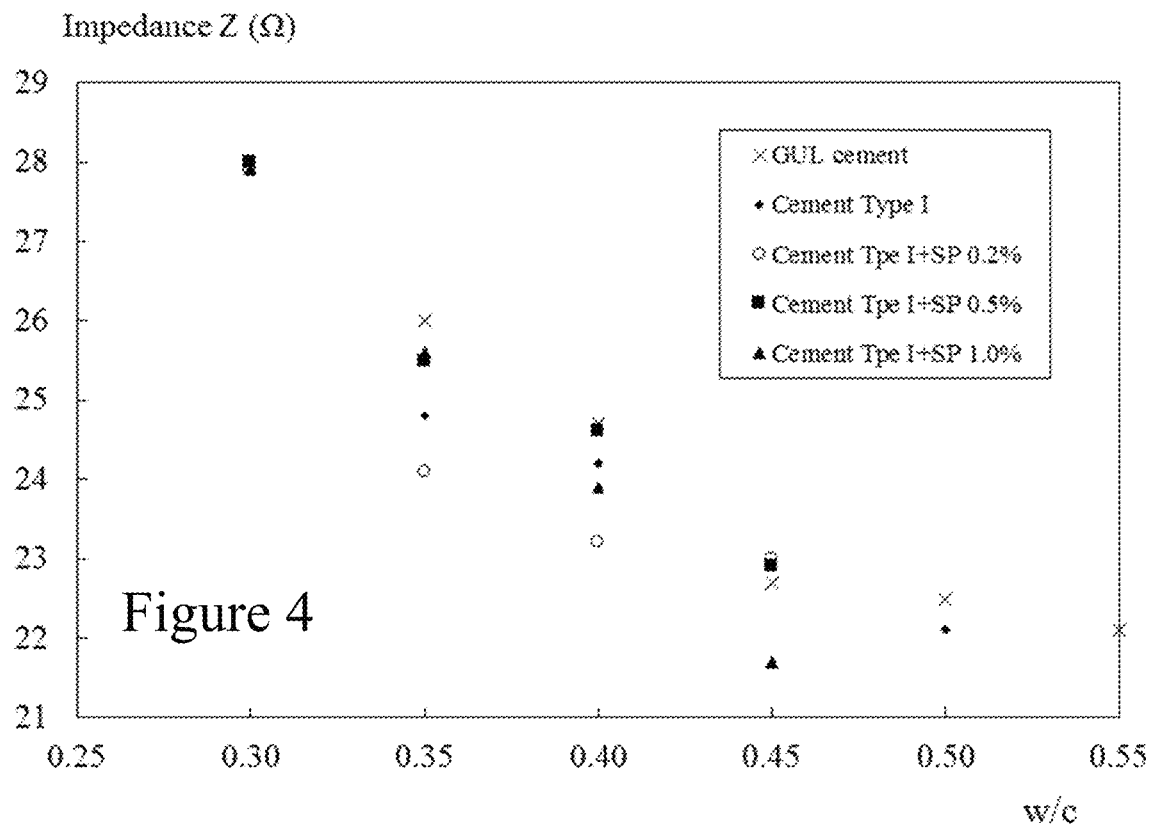
FIG. 4 depicts the estimation of water to cement ratio using electrical impedance data according to an embodiment of the invention.

The present invention is directed to concrete testing and concrete structure characterization, more particularly to electrical methods and systems for establishing cured concrete performance from measurements of wet concrete and automated methods and systems for periodic and/or continuous characterization of concrete structures.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device that requires a battery or other independent form of energy for power. This includes devices including, but not limited to, cellular telephone, smartphone, personal digital assistant (PDA), portable computer, pager, portable multimedia player, portable gaming console, laptop computer, tablet computer, and an electronic reader. A "fixed electronic device" (FED) as used herein and throughout this disclosure, refers to a wired and/or wireless device used which is dependent upon a form of energy for power provided through a fixed network, e.g. an electrical mains outlet coupled to an electrical utilities network. This includes devices including, but not limited to, portable computer, desktop computer, computer server, Internet enabled display, mainframe, and server cluster. Such PEDs and FEDs supporting one or more functions and/or applications including, but not limited to, data acquisition, data storage, data analysis, communications, and Internet/Web interface.

Referring to FIG. 1 there are depicted first and second concrete infrastructures 110 and 120 which are the "Judge Harry Pregerson" Interchange in Los Angeles and "High Five" Interchange in Dallas, Tex. respectively. Whilst perhaps overly dramatic these are just two of the 600,000 bridges and millions of buildings in the United States alone requiring characterization for corrosion. Similarly, these represent albeit similarly overly dramatic examples of the new concrete infrastructure being constructed both to address new requirements and replace existing infrastructure either from evolving requirements or addressing safety issues. Examples of such infrastructure builds are presented with first and second pouring images 130 and 140 respectively. First pouring image 130 depicts the westbound West Dodge Expressway bridge deck pour at approximately 117th Street in Omaha, Nebr. This is at least ground level where the concrete is piped a short distance from the truck to where it is poured. In second pouring image 140 there is depicted pouring concrete on the 45th story of the 600-foot-tall condominium tower called One Rincon Hill in San Francisco, Calif. In this instance the wet concrete is provided from a plant at Hunters Point nearly 2 miles (approximately 3.2 km) away before being pumped to the pouring on the 45$^{th}$ floor of the ultimately 60 story building.

1. Prior Art Electrical Resistivity Measurements

Now referring to FIG. 2 there is depicted first image 210 of a surface electrical resistivity measurements according to the prior art. First image 210 shows a worker walking across a road surface performing measurements wherein they walk one pace, stop, make a measurement, walk another pace, stop, make a measurement. There is no reference to their position along the road surface and their position across the road whilst defined by the eroded white line at this point will be lost when the road surface is resurfaced, repainted, etc. Accordingly, these measurements are isolated, discrete measurements that cannot be correlated to any subsequent measurements taken in 1, 2, 3, or 5 years' time for example to determine structure changes. Equally, the data when taken away and analysed identifies an area of corrosion requiring correction through physical intervention. A work crew returning may be addressing a small area but without alignment to the physical structure the measurements provide no additional benefit and accordingly it is likely that the physical intervention will involve a substantial portion of the road surface. Likewise, a simple error in denoting which side of the road the measurements were made on results in the wrong side of the road surface being ripped up.

Second image 220 depicts a four-point Wenner probe as employed in surface electrical resistivity measurements such as those made by the worker in first image 210. It applies a 40 Hz AC electrical current from the outer pair of electrodes and measures the voltage between the inner pair of electrodes which is then converted to an electrical resistivity displayed on the screen and in the instance of first image 210 is manually entered into a portable device by the worker. Alternatively, rather than onsite measurements through such Wenner probes as depicted in fourth image 220 embedded sensors such as depicted in third image 230 may be employed. The probe depicted is a CORRATER Model 800 probe from Rohrback Cosasco Systems that measures the instantaneous corrosion rate of reinforcing steel in concrete by the method of linear polarization resistance (LPR). Each reading gives the instantaneous corrosion rate of the electrodes in the concrete environment, and the probes are monitored frequently or continuously to track changes in corrosion rate. However, these are expensive individually and deploying a matrix of them across say a 100 m×10 m bridge prohibitive even without considering the additional complexities of interface cabling, measurement electronics etc. Also depicted are fourth and fifth image 240 and 250 respectively for electrical resistance measurements systems. Fourth image 240 depicts the Giatec RCON™ which is a non-destructive device for measuring the electrical resistivity of concrete specimens in the laboratory without any additional sample preparation requirements and allows measurements to be made on the same concrete samples that are currently used for the compressive strength testing of concrete. Fifth image 250 depicts Giatec Surf™ which is a laboratory test device for rapid, easy and accurate measurement of the surface electrical resistivity of concrete based on the four-probe (Wenner Array) technique.

Referring to FIG. 3 there is depicted half-cell potential meter 310 according to the prior art which comprises half-cell 310B and multimeter 310A which are depicted in deployment 330 and are connected to each other via an interconnection cable. The other side of the multimeter 310A is electrically connected to the rebar 340 such that the electrical circuit for the multimeter 310A therefore completed via the rebar 340, concrete and half-cell 310B. Electrical contact of the half-cell 310B to the concrete is facilitated by a wet sponge. As corrosion of reinforcing steel is an electro-chemical process then the behaviour of the steel can be characterized by measuring its half-cell potential where the greater the potential the higher the risk that corrosion is taking place. An electrode forms one half of the cell and the reinforcing steel in the concrete forms the other. A common reference electrode for site use is silver/silver chloride in potassium chloride solution although the copper/copper sulphate electrode is still widely used. It should be noted that the measured potential should be corrected relatively based on the type of the electrode. The survey procedure is firstly to locate the steel and determine the bar spacing using a cover meter, then the cover concrete is removed locally over a suitable bar and an electrical connection made to the steel. It is necessary to check that the steel is electrically continuous by measuring the resistance between two widely separated points. The reinforcing bar is connected to the half-cell 310B via the multimeter 310A. Accordingly, this is a time consuming process and mapping subject to the same issues as discussed supra in respect of FIG. 2.

2. Testing at Installation—Formation of Concrete Structure

As noted supra these prior art electrical resistance measurements whilst easier to perform than the wet concrete tests are performed upon cured installed concrete infrastructure. Also noted supra standard wet concrete tests include slump test, air retention test, set time, and compressive strength. Examples of these test are depicted in FIG. 3 as:

slump test 320, with the cone filling and slump measurement stages depicted;

air retention test 350, with securing of the lid to the concrete filled bucket and measurement stages depicted;

set time 360, with a measurement depicted; and compressive strength 370, with a measurement system depicted.

Electrical impedance method for in-situ measuring and monitoring of concrete properties would be beneficial in order to simplify testing procedures, reduce the time taken to perform tests, allow for increased sampling rates, reduce errors, and reduce time before issues are identified with concrete delivered that is out of specification.

As the electrical impedance of concrete can be simply related to the pore network characteristics of concrete such as pore size and their connectivity, moisture content in the pores and pore solution chemistry and in general the microstructure of concrete. The electrical impedance of concrete at certain ranges of frequency therefore, according to embodiments of the invention, has been well correlated with important early-stage properties of concrete such that a variety of properties may be established including:

Determination of water to cement ratio of concrete;

Estimation of in-situ compressive strength of concrete after pouring;

Prediction of 7-day, 28-day and 56-day compressive strength of concrete (ASTM C39)

Detection of initial and final setting of concrete (ASTM C403);

Assessment of transport properties of concrete such as permeability, diffusivity and porosity (ASTM C1202, ASTM C1543);

Crack detection; and

Detection of changes in the pore solution.

2.1 Determination of Water to Cement Ratio of Concrete:

The measurement of water to cement ratio of concrete before or during pouring the concrete is critically important in the construction industry to ensure the appropriate quality of the concrete delivered by concrete trucks to the construction site. The water/cement ratio is a parameter that is specified for a concrete mixture. Higher water content increases the porosity of the hardened concrete and thus decreases its strength and durability but low water content, in contrast, decreases the workability of concrete. So, it is important to have just enough water in the concrete mixture. Whilst the amount of water within the concrete truck may be known when it leaves the concrete supplier's facility what it is by the time it is poured depends upon a variety of factors, including but not limited to, ambient temperature, time period between mixing and pouring, and additional water added by the truck driver/contractor etc. during transit and at the construction site. Accordingly, monitoring the water/cement ratio in real-time beneficially provides concrete suppliers, builders, owners, regulators, etc. with enhanced data which can be archived, accessed, analysed, etc. subsequently as well as avoiding pouring low-quality concrete, the replacement of which will be very costly and in some cases impossible.

Accordingly, referring to FIG. 1 there is depicted the estimated water content from electrical impedance data by the inventors according to an embodiment of the invention exploiting electrical impedance data on wet concrete. Accordingly, based upon no information of the concrete type a first water content range may be specified based upon a simple electrical measurement and this water content range may be specified with improved accuracy based upon specification of the concrete type. Optionally, depending upon the sampling time, integration time, number of measurements, number of measurement frequencies etc. required for the measurement continuous or pseudo-continuous monitoring may be performed on the concrete at the construction site, at the pouring location, at the delivery location, and/or during transport.

2.2 Estimation of In-Situ Compressive Strength of Concrete after Pouring:

Monitoring the compressive strength of concrete during the first few days from pouring up to 7 days after pouring is important for the optimization of formwork removal, especially in the winter time. Aside from the type of concrete mixture, the rate of strength development in concrete also significantly depends on other factors, such as the concrete temperature fluctuation which becomes important in different geographic regions at different times of the year, e.g. winter in north-eastern US, summer in south-west US, etc. The electrical resistivity of concrete can be used to estimate the compressive strength of concrete.

Figure 5:
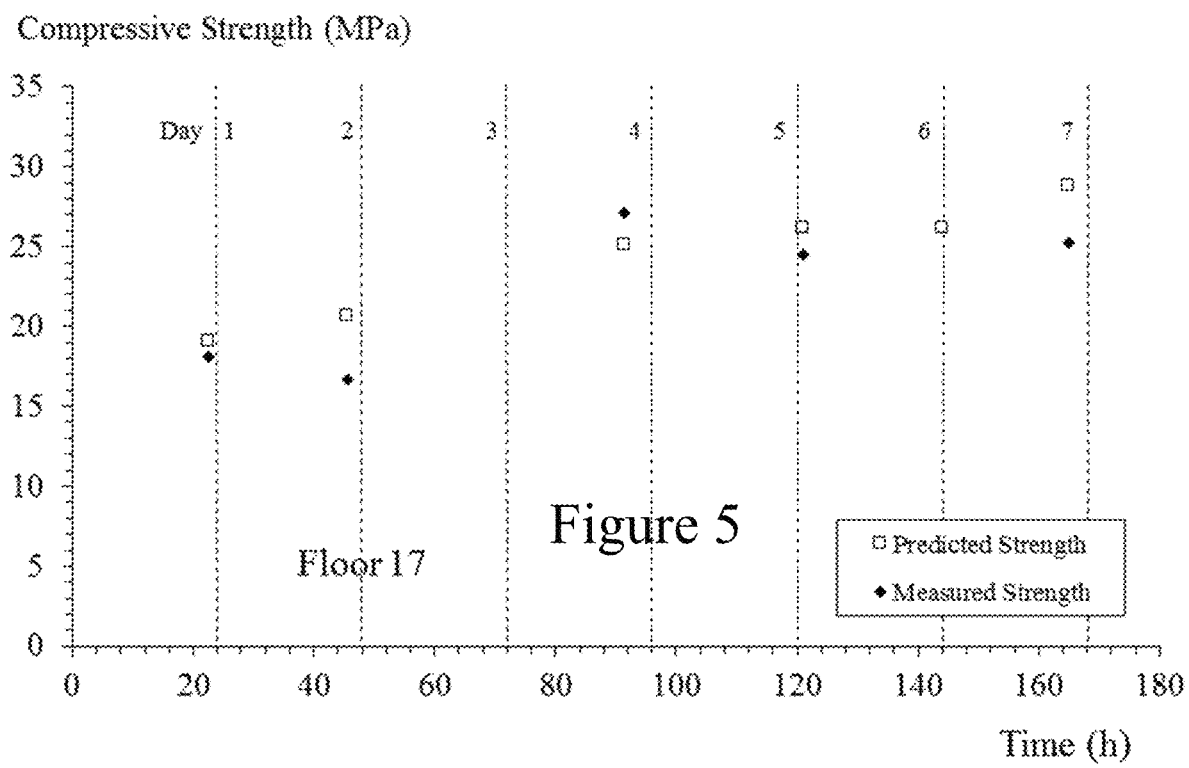
FIG. 5 depicts the estimation of real-time in-situ strength of concrete using electrical resistivity data according to an embodiment of the invention for floor 17 of a building.
Figure 6:
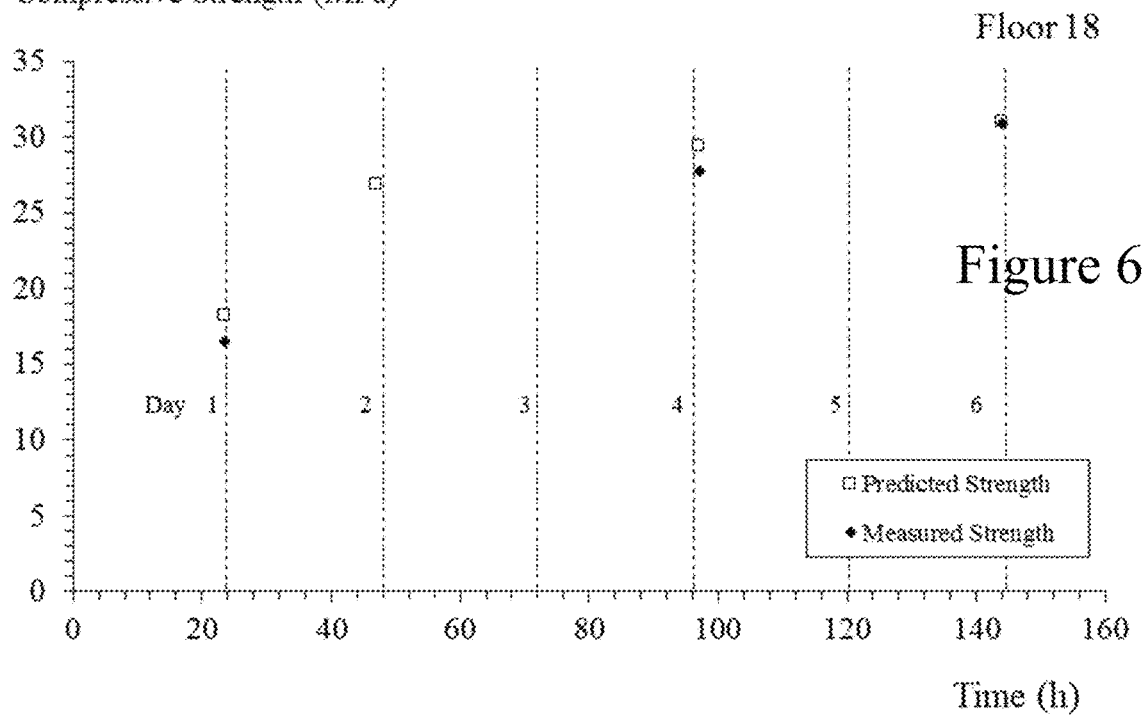
FIG. 6 depicts the estimation of real-time in-situ strength of concrete using electrical resistivity data according to an embodiment of the invention for floor 17 of a building.

Referring to FIGS. 5 and 6 there are depicted graphs for the $17^{th}$ and $18^{th}$ floors of a construction projected wherein the predicted compressive strength of concrete as derived by the inventors using electrical resistance measurements is plotted as a function of time. Accordingly, based upon a minimum target compressive strength of 25 MPa, for example, it is evident that this is reached from electrical measurement based analysis after 2 days allowing removal of framework at that time as only slight increase is noted from measurements over the following 5 days. Accordingly, electrical measurements allow for rapid, onsite measurements to be performed without requiring poured concrete to be sampled and characterised at a laboratory.

Figure 7:
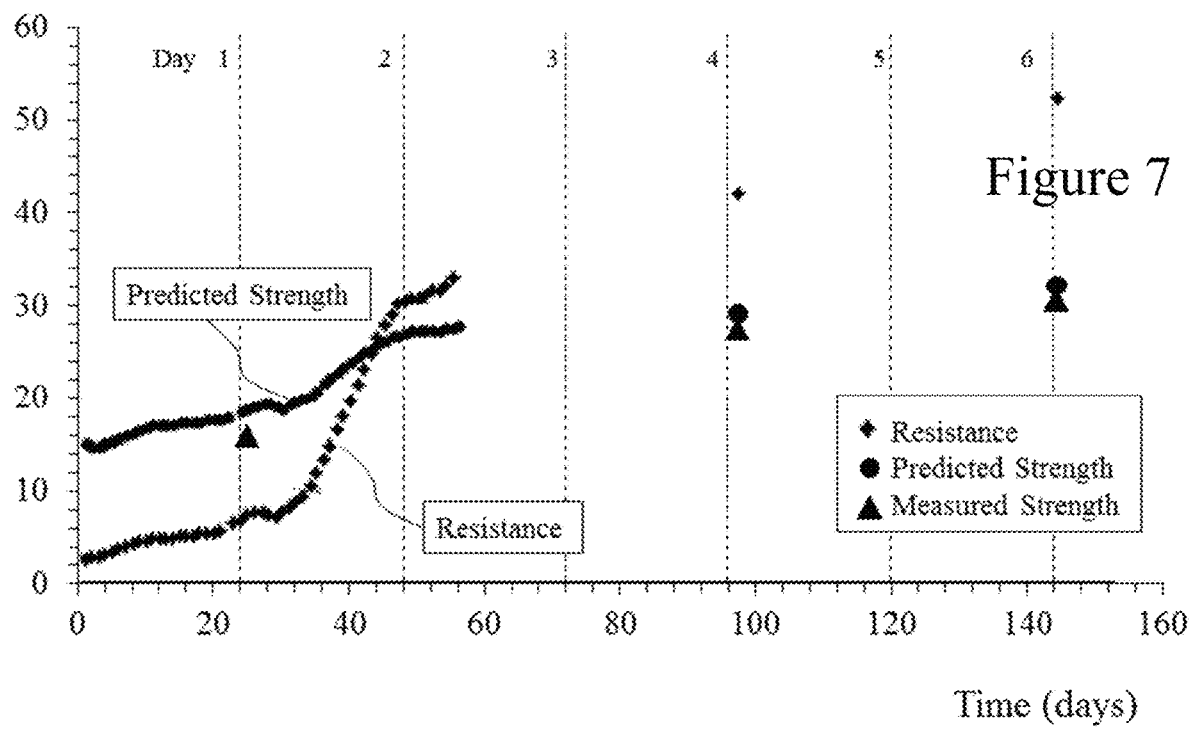
FIG. 7 depicts the extrapolation of concrete electrical resistivity for prediction of long-term compressive strength estimation according to an embodiment of the invention.

2.3 Prediction of 7-Day, 28-Day and 56-Day Compressive Strength of Concrete (ASTM C39):

The inventors have established that the electrical impedance of concrete measured at a certain frequency range can also be used to predict the long term strength of concrete such as those required at 7-day, 28-day and 56-day. The long-term compressive strength of concrete is an important design parameter that needs to be met during the construction but as with short-term compressive strength the complexity/cost/delay of physical sampling and laboratory testing can be removed through onsite testing with handheld meters providing electrical impedance measurements or temporarily installed electrical impedance data loggers that can be removed, relocated, reused etc. Referring to FIG. 7 there is depicted a plot of predicted and measured strength as a function of time together with electrical impedance measurements of the concrete.

2.4 Detection of Initial and Final Setting of Concrete (ASTM C403):

The determination of initial and final setting of concrete is also important in deciding when to start the process of finishing the surface of concrete and also for sequential construction systems in which the concrete pouring is performed sequentially such as those in dams, silos and towers. As noted supra the prior art technique is based upon periodic physical testing of concrete samples taken from the pour. In contrast the inventors have established the determination of setting time through electrical impedance measurements as depicted in FIG. 8 where these are compared to the setting times of fresh concrete measured using the current standard, see ASTM C403 "Standard Test Method for Time of Setting of Concrete Mixtures by Penetration Resistance." Accordingly, electrical impedance measurements present a non-invasive, onsite test for setting time wherein data acquisition and determination can be automated and/or simplified allowing the removal for the requirement of trained personal, dedicated laboratory etc.

2.5 Assessment of Transport Properties of Concrete such as Permeability, Diffusivity and Porosity:

Historically, standards such as ASTM C1202 "Standard Test Method for Electrical Indication of Concrete's Ability to Resist Chloride Ion Penetration" and ASTM C1543 "Standard Test Method for Determining the Penetration of Chloride Ion into Concrete by Ponding." Acceptance criteria for this test according to such tests must consider multiple factors, including for example sample age and curing procedure, that affect the results and ensure balanced risk between supplier and purchaser. Accordingly, the inventors have established the electrical impedance of hardened concrete at long term measured at a certain frequency range and defined moisture level correlates with the transport properties of concrete such as diffusivity, permeability and porosity. As depicted in FIG. 9A the chloride diffusion constant is plotted as a function of the electrical conductivity determined from electrical impedance measurements is presented for twenty different proportions.

Figure 9B:
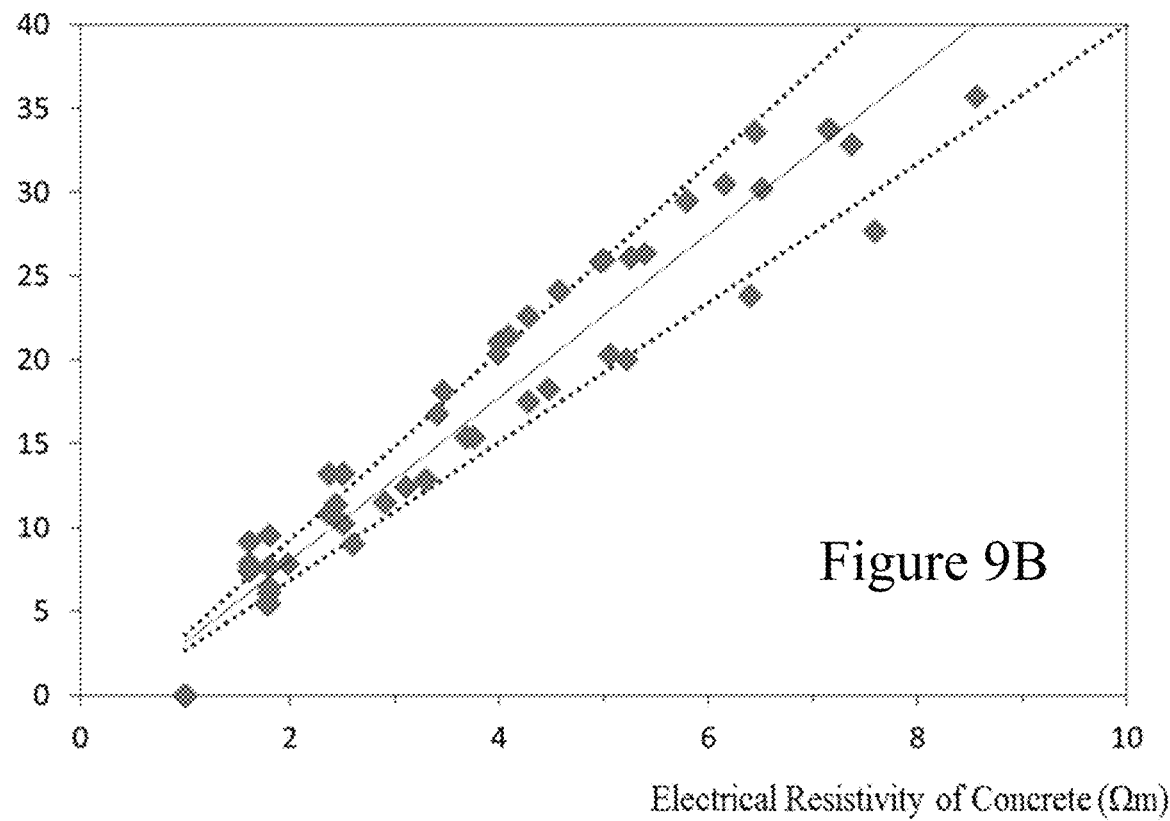
FIG. 9B depicts the relationship between electrical conductivity and compressive strength for concrete for concrete samples as measured according to an embodiment of the invention.

2.6 Assessment of Ultimate Compressive Strength of Concrete:

Now referring to FIG. 9B there is depicted a graph showing the compressive strength of concrete samples plotted as a function of the electrical resistivity of the concrete samples as measured according to an embodiment of the invention. Accordingly, it is evident that the compressive strength shows a strong essentially linear correlation with electrical resistivity allowing such electrical measurements to be made and provide an indication of mechanical strength without requiring a concrete core sample be taken and measured in a laboratory at a later point in time. As such point of use measurements can provide earlier feedback and decision making for a construction activity involving a concrete pour.

Within other embodiments of the invention the electrical impedance measurements allows for ongoing structural factor determination such as crack detection and changes in pore solution. In the former case the electrical resistivity of concrete can provide an indication of the cracking initiation and the propagation in concrete structures as in general cracking decreases the solid connectivity and the cross section of the concrete element and thus increases the electrical resistivity. In the latter, the ingress of aggressive ions such as chlorides into the pore structure of concrete increases the conductivity of the pore solution and thus decreases the electrical impedance of concrete. Accordingly electrical impedance can be employed to detect and monitor the penetration of such ions that can lead to the deterioration of concrete.

In addition to the benefits of knowing the water/cement ratio and strength development of concrete as described above other benefits can be derived including, for example, a feedback system to the concrete batching plant such that the amounts of the concrete ingredients can be optimized knowing the variations in the water/cement ratio and strength of the poured concrete and accordingly adjust for the effects of the transportation, delivery and pouring to ensure the poured concrete meets the minimum requirements established and to save on the cost of materials.

Beneficially, electrical impedance analysis in situ allows for curing/acceleration techniques such as the heating of formwork during the first few days after concrete pouring can be also optimized/adjusted to save energy and achieve the desired strength to allow framework removal earlier.

Within the experimental electrical impedance procedures described supra it is known that the electrical impedance of concrete changes with temperature variation such that higher temperature translates into lower electrical impedance. Accordingly, in order to compensate the effect of temperature on the results, a modification factor needs to be applied to offset the effect of temperature using Arrhenius equation as given by Equation (1).

$$F = e^{\left(\frac{E_a}{R}\right)\left(\frac{1}{T_0} - \frac{1}{T}\right)} \quad (1)$$

where F is the modification factor, $T_0$ is the reference temperature, $E_a$ is the activation energy, and R is the gas constant. Within the prior art values of this activation energy have been reported. In contrast, the inventors have established that for each application described supra in respect of exploiting electrical impedance measurements that there is a specific value of the activation energy coefficient.

Within the embodiments of the invention described supra the electrical measurement may be made using disposable and/or reusable wireless sensors deployed upon the infrastructure and pulled/pushed via a network and/or PED/FED to an application or applications for storage and analysis. For example, a disposable sensor may exploit Bluetooth connectivity for short range low power communications and ad-hoc network protocols so communicate electrical measurement data to a node or nodes wherein it is pushed to remote servers, what is commonly referred to today as "the cloud", through one or more different network interfaces and/or network protocols. Subsequently, this cloud stored data can be analysed in real time and/or periodically to determine one or more of the measurements described supra. At that point the derived performance data may be pushed to one or more entities including, for example, the concrete supplier, builder, owner of the structure, regulatory authorities etc. Alternatively, wired sensors or sensor nets may be deployed.

2.6 Exemplary Network and Device Configurations for Testing at Installation

Figure 10:
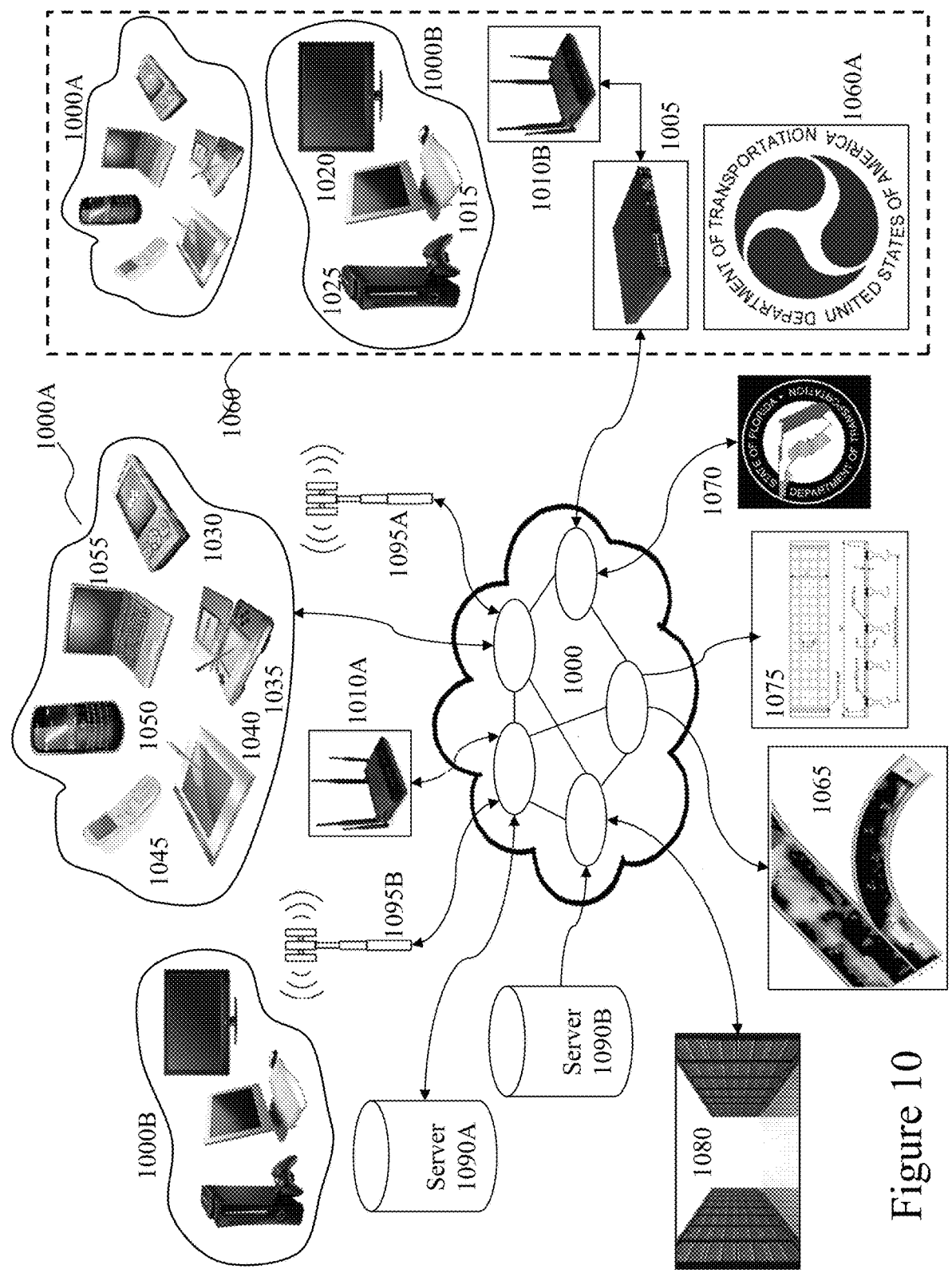
FIG. 10 depicts a network supporting communications to and from electronic devices implementing contextual based UIs according to embodiments of the invention.

Now referring to FIG. 10 there is depicted a network 1000 supporting communications to and from electronic devices implementing embodiments of the invention. As shown first and second user groups 1000A and 1000B respectively interface to a telecommunications network 1000. Within the representative telecommunication architecture a remote central exchange 1080 communicates with the remainder of a telecommunication service providers network via the network 1000 which may include for example long-haul OC-48/OC-192 backbone elements, an OC-48 wide area network (WAN), a Passive Optical Network, and a Wireless Link. The central exchange 1080 is connected via the network 1000 to local, regional, and international exchanges (not shown for clarity) and therein through network 1000 to first and second wireless access points (AP) 1095A and 1095B respectively which provide Wi-Fi cells for first and second user groups 1000A and 1000B respectively. Also connected to the network 1000 are first and second Wi-Fi nodes 1010A and 1010B, the latter of which being coupled to network 1000 via router 1005. Second Wi-Fi node 1010B is associated with Government Body 1060A and environment 1060 within which are first and second user groups 1000A and 1000B. Second user group 1000B may also be connected to the network 1000 via wired interfaces including, but not limited to, DSL, Dial-Up, DOCSIS, Ethernet, G.hn, ISDN, MoCA, PON, and Power line communication (PLC) which may or may not be routed through a router such as router 1005.

Within the cell associated with first AP 1010A the first group of users 1000A may employ a variety of portable electronic devices including for example, laptop computer 1055, portable gaming console 1035, tablet computer 1040, smartphone 1050, cellular telephone 1045 as well as portable multimedia player 1030. Within the cell associated with second AP 1010B are the second group of users 1000B which may employ a variety of fixed electronic devices including for example gaming console 1025, personal computer 1015 and wireless/Internet enabled television 1020 as well as cable modem 1005.

Also connected to the network 1000 are first and second APs which provide, for example, cellular GSM (Global System for Mobile Communications) telephony services as well as 3G and 4G evolved services with enhanced data transport support. Second AP 1095B provides coverage in the exemplary embodiment to first and second user groups 1000A and 1000B. Alternatively the first and second user groups 1000A and 1000B may be geographically disparate and access the network 1000 through multiple APs, not shown for clarity, distributed geographically by the network operator or operators. First AP 1095A as show provides coverage to first user group 1000A and environment 1060, which comprises second user group 1000B as well as first user group 1000A. Accordingly, the first and second user groups 1000A and 1000B may according to their particular communications interfaces communicate to the network 1000 through one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-2000. It would be evident to one skilled in the art that many portable and fixed electronic devices may support multiple wireless protocols simultaneously, such that for example a user may employ GSM services such as telephony and SMS and Wi-Fi/WiMAX data transmission, VOIP and Internet access. Accordingly portable electronic devices within first user group 1000A may form associations either through standards such as IEEE 802.15 and Bluetooth as well in an ad-hoc manner.

Also connected to the network 1000 are concrete mapping environment 1065, State Body 1070, and Bridge Structure environment 1075 as well as first and second servers 1090A and 1090B which together with others not shown for clarity, may host according to embodiments of the inventions multiple services associated with one or more organizations, including but not limited to, a provider of the software operating system(s) and/or software application(s) associated with the electronic device(s), a provider of the electronic device, provider of one or more aspects of wired and/or wireless communications, provider of the electrical measurement devices, provider of mapping analysis software, provider of electrical measurement analysis software, provider of wired/wireless sensors, global position system software, materials databases, building databases, regulatory databases, license databases, construction organizations, websites, construction organization databases, infrastructure owner databases, and software applications for download to or access by FEDs, PEDs, and electrical measurement systems. First and second servers 1090A and 1090B may also host for example other Internet services such as a search engine, financial services, third party applications and other Internet based services. Not shown, for clarity, are the electrical impedance measurement systems (for example, a PED and/or FED with a software application or a dedicated measurement device) and/or electrical impedance measurement sensors. Accordingly, within the embodiment of the invention wherein a PED and/or FED may accumulate data from one or more electrical impedance sensors and/or electrical impedance systems then this may communicate this through network 1000 to one or more servers, e.g. first and/or second servers 1090A and 1090B respectively. Accordingly based upon one or more applications in execution on first and/or second servers 1090A and 1090B the processed data may be stored as well as being pushed to databases for one or more entities including, for example, the concrete supplier, builder, owner of the structure, regulatory authorities etc.

Accordingly, it would be evident to one skilled in the art that electrical measurement systems and/or concrete corrosion analysis according to embodiments of the invention described supra in respect of FIGS. 4 through 9 may be connected to a communications network such as network 1000 either continuously or intermittently. It would be further evident that the electrical measurements of concrete together with the analysis of the measurements and their mapping may be triggered as a result of activities triggered by, for example, the Government Body 1060A and/or State Body 1070 in order to address regulatory requirements, safety concerns etc.

Accordingly, the engineers, workers and/or technicians who will be performing the measurements may be able to access Bridge Structure Environment 1075 to obtain architect drawings, engineering data, design data, etc. relating to the concrete structure being assessed. It would be evident that other databases addressing other environments such as for example, shopping malls, road surfaces, public walkways, residential housing, and commercial buildings may be accessed where the requirements for assessment relate to these structures and the regulatory bodies may be similarly transportation or include others such as Department of Housing, Federal Highway Department, and Bureau of Industry and Security. Where all or part of the structure being assessed has been previously assessed then data may be retrieved from the Concrete Mapping Environment for example. It would be evident that with coordinated based measurement acquisition that an engineer may view in real time a contour map of the structure being assessed as the data is acquired and accordingly may ask for additional measurements or repeated measurements to be performed. Additionally, previous contour mapping and electrical measurements may allow for targeted re-assessment of areas of concern at a different frequency to that of the overall structure.

Figure 11:
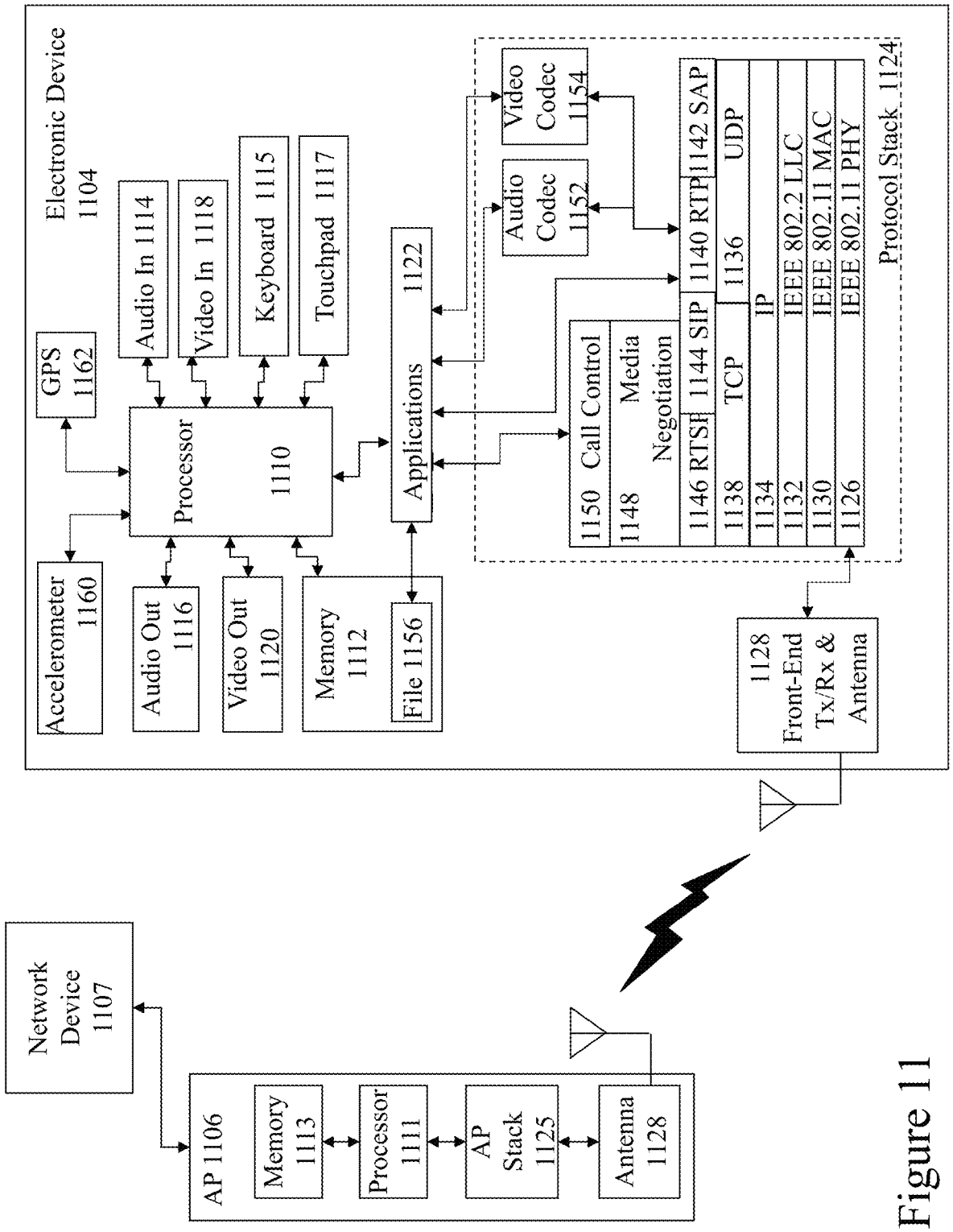
FIG. 11 depicts an electronic device and network access point supporting contextual based UIs according to embodiments of the invention.

FIG. 11 there is depicted an electronic device 1104 and network access point 1107 supporting contextual based UIs according to embodiments of the invention. Electronic device 1104 may for example be a portable electronic device or a fixed electronic device and may include additional elements above and beyond those described and depicted. Also depicted within the electronic device 1104 is the protocol architecture as part of a simplified functional diagram of a system 1100 that includes an electronic device 1104, such as a smartphone 1055, an access point (AP) 1106, such as first AP 1010, and one or more network devices 1107, such as communication servers, streaming media servers, and routers for example such as first and second servers 1090A and 1090B respectively. Network devices 1107 may be coupled to AP 1106 via any combination of networks, wired, wireless and/or optical communication links such as discussed above in respect of FIG. 10. The electronic device 1104 includes one or more processors 1110 and a memory 1112 coupled to processor(s) 1110. AP 1106 also includes one or more processors 1111 and a memory 1113 coupled to processor(s) 1111. A non-exhaustive list of examples for any of processors 1110 and 1111 includes a central processing unit (CPU), a digital signal processor (DSP), a reduced instruction set computer (RISC), a complex instruction set computer (CISC) and the like. Furthermore, any of processors 1110 and 1111 may be part of application specific integrated circuits (ASICs) or may be a part of application specific standard products (ASSPs). A non-exhaustive list of examples for memories 1112 and 1113 includes any combination of the following semiconductor devices such as registers, latches, ROM, EEPROM, flash memory devices, non-volatile random access memory devices (NVRAM), SDRAM, DRAM, double data rate (DDR) memory devices, SRAM, universal serial bus (USB) removable memory, and the like.

Electronic device 1104 may include an audio input element 1114, for example a microphone, and an audio output element 1116, for example, a speaker, coupled to any of processors 1110. Electronic device 1104 may include a video input element 1118, for example, a video camera, and a video output element 1120, for example an LCD display, coupled to any of processors 1110. Electronic device 1104 also includes a keyboard 1115 and touchpad 1117 which may for example be a physical keyboard and touchpad allowing the user to enter content or select functions within one of more applications 1122. Alternatively the keyboard 1115 and touchpad 1117 may be predetermined regions of a touch sensitive element forming part of the display within the electronic device 1104. The one or more applications 1122 that are typically stored in memory 1112 and are executable by any combination of processors 1110. Electronic device 1104 also includes accelerometer 1160 providing three-dimensional motion input to the process 1110 and GPS 1162 which provides geographical location information to processor 1110.

Electronic device 1104 includes a protocol stack 1124 and AP 1106 includes a communication stack 1125. Within system 1100 protocol stack 1124 is shown as IEEE 802.11 protocol stack but alternatively may exploit other protocol stacks such as an Internet Engineering Task Force (IETF) multimedia protocol stack for example. Likewise AP stack 1125 exploits a protocol stack but is not expanded for clarity. Elements of protocol stack 1124 and AP stack 1125 may be implemented in any combination of software, firmware and/or hardware. Protocol stack 1124 includes an IEEE 802.11-compatible PHY module 1126 that is coupled to one or more Front-End Tx/Rx & Antenna 1128, an IEEE 802.11-compatible MAC module 1130 coupled to an IEEE 802.2-compatible LLC module 1132. Protocol stack 1124 includes a network layer IP module 1134, a transport layer User Datagram Protocol (UDP) module 1136 and a transport layer Transmission Control Protocol (TCP) module 1138.

Protocol stack 1124 also includes a session layer Real Time Transport Protocol (RTP) module 1140, a Session Announcement Protocol (SAP) module 1142, a Session Initiation Protocol (SIP) module 1144 and a Real Time Streaming Protocol (RTSP) module 1146. Protocol stack 1124 includes a presentation layer media negotiation module 1148, a call control module 1150, one or more audio codecs 1152 and one or more video codecs 1154. Applications 1122 may be able to create maintain and/or terminate communication sessions with any of devices 1107 by way of AP 1106. Typically, applications 1122 may activate any of the SAP, SIP, RTSP, media negotiation and call control modules for that purpose. Typically, information may propagate from the SAP, SIP, RTSP, media negotiation and call control modules to PHY module 1126 through TCP module 1138, IP module 1134, LLC module 1132 and MAC module 1130.

It would be apparent to one skilled in the art that elements of the electronic device 1104 may also be implemented within the AP 1106 including but not limited to one or more elements of the protocol stack 1124, including for example an IEEE 802.11-compatible PHY module, an IEEE 802.11-compatible MAC module, and an IEEE 802.2-compatible LLC module 1132. The AP 1106 may additionally include a network layer IP module, a transport layer User Datagram Protocol (UDP) module and a transport layer Transmission Control Protocol (TCP) module as well as a session layer Real Time Transport Protocol (RTP) module, a Session Announcement Protocol (SAP) module, a Session Initiation Protocol (SIP) module and a Real Time Streaming Protocol (RTSP) module, media negotiation module, and a call control module.

Portable and fixed electronic devices represented by electronic device 1104 may include one or more additional wireless or wired interfaces in addition to the depicted IEEE 802.11 interface which may be selected from the group comprising IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, IMT-2000, DSL, Dial-Up, DOCSIS, Ethernet, G.hn, ISDN, MoCA, PON, and Power line communication (PLC).

3. Testing During Operational Lifetime of Concrete Structure

Within the prior art one common analysis technique is an output only method based upon the Fourier transform method based upon the principal that damage will cause a reduction in stiffness in a given structure, which in turn, will cause a shift in its natural frequency. This being commonly referred to as the Fourier Transform Method (FTM) or Natural Frequency Method. Referring to FIG. 12 there is presented a graph produced by Wang et al in "A Non-destructive Damage Detection Method for Reinforced Concrete Structures Based on Modal Strain Energy" (University of Technology, Sydney, PhD Thesis, 2010) which demonstrates the shift in natural frequency due to damage of a structure. The reference numerals 1 to 4 indicate increasing levels of damage severity. Although obtaining the natural frequency of a structure is often easily done with few measurement points required, see for example Fan et al. in "Vibration-based Damage Identification Methods: A Review and Comparative Study" (Structural Health Monitoring, Vol. 10(1), pp. 83-111), it does not have a high sensitivity to damage and may be masked by environmental noise. Another disadvantage of using the Fourier transformation is that although the presence of damage may be indicated, the location of damage is still unknown. This may be compensated for using a short-time Fourier transformation method, however, resolution problems arise in which damage is still not able to be located accurately especially within larger, more complicated structures.

Another analysis technique within the prior art is that of Mode Shape (MS) methods that operate under the similar assumption of natural frequency methods in that the presence of damage will produce a measureable difference in the mode shape. Considering a simple bridge of uniform cross-section supported at its ends then this simply supported beam is considered to be split up into "N" discrete segments. Using an accelerometer at each segment, the mode shape of the structure can be determined. This is usually done through some sort of forced or natural source of excitation with the use of techniques such as the natural excitation technique (NExT), see for example Yun in "Detection and quantification of structural damage under ambient vibration environment" (Structural Engineering and Mechanics, Vol. 42(3), pp. 425-448); an eigensystem realization algorithm (ERA), see for example Yun; or a stochastic subspace identification (SSI) method, see for example Ubertini et al in "Automated modal identification in operational conditions and its application to bridges. Engineering Structures, Vol. 46, pp. 264-278). Once the mode shape is obtained, the change in mode shape may be used as a damage indicator.

$$\Delta\varphi_i = \varphi_i^* - \varphi_i \qquad (2)$$

$$Z_j = \frac{\Delta\varphi_j - \mu}{\sigma} > 2 \qquad (3)$$

Considering Equation (2) then $\varphi$ is an N length vector that represents the undamaged mode shape of the mode of the structure and $\varphi^*$ represents the N length vector of the damaged mode shape. If there is a significant difference in the mode shape of one of the segments within the structure, damage has most likely occurred at this location. "Significant" damage may be defined for example by Equation (3) where $\Delta\varphi_j$ signifies the change in mode shape of the $j^{th}$ segment, $\mu$ represents the mean value of change in mode shape for the entire beam, and $\sigma$ is the standard deviation. Although mode shape methods are commonly documented, they are restricted in application as they do not contain a high sensitivity to damage. Often, they are only useful for preliminary rough localization of damage within a structure. For these reasons, application in in-situ structures has been highly limited.

Accordingly, within the prior art Mode Shape Curvature (MSC) and Modal Strain Energy (MSE) approaches have been established. The MSC of a structure is the second derivative of its mode shape and such methods seek to improve on the sensitivity of mode shape to damage. To obtain the MSC of a beam that has been separated into discrete segments wherein Equation (4) is one such method to define the MSC for the $j^{th}$ segment.

$$MSC_j = \frac{(\varphi_{j+1} + \varphi_{j-1} - 2\varphi_j)}{h_j^2} \quad (4)$$

Here, $\varphi_j$ represents the $j^{th}$ component of the MS vector (i.e. the $j^{th}$ discrete segment of the beam) and $h_j$ signifies the length of the $j^{th}$ discrete segment of the beam. The MSC can be used in place of mode shape in the damage index method discussed in the above section. Doing so has been shown to improve damage localization and reduce noise effects. However, MSC methods also have some of their own disadvantages. For example, a finer mesh measurement points is often required to acquire an accurate depiction of modal curvature. Second, Equation (4) as used to derive the modal shape curvature can introduce errors. This error may become significant if a fine mesh of measurement instruments is not employed. Although MSC by itself is a good indicator of location of moderate to high levels of damage; it is still not able to detect smaller levels of damage. To further complicate the matter, only the MSC of lower modes of vibration should be used. If the MSC of higher modes are used, this often leads to the detection of damages even though they may not be present, i.e. false-positives, see Biswas.

$$\beta_{ij} = \frac{\int_j (MSC_i^*)^2 dx + \int_0^L (MSC_i^*)^2 dx}{\int_j (MSC_i)^2 dx + \int_0^L (MSC_i)^2 dx} * \frac{\int_0^L (MSC_i)^2 dx}{\int_0^L (MSC_i^*)^2 dx} \quad (5)$$

In contrast the Modal Strain Energy (MSE) of a structure is derived from the modal shape curvature can also be used as a damage indicator in the form of fractional strain energy, see for example Stubbs et al. in "Field Verification of a Nondestructive Damage Localization and Severity Estimation Algorithm" (Proc. of IMAC 1995, pp. 210-218. Such a definition of fraction strain energy is given by Equation (5) where i represents the $i^{th}$ mode and all symbols are the same as previous Equations. As the amplitude of each mode shape is trivial, we may take the normalized vector such that $\varphi\varphi^T=1$. By doing so, we are now able to use the modal strain energy of all available modes up to the $n^{th}$ mode as given by Equation (6) which may be re-written in discrete form as Equation (7).

$$\beta_{ij} = \sum_{i=1}^{n} \left( \frac{\int_j (MSC_i^*)^2 dx + \int_0^L (MSC_i^*)^2 dx}{\int_j (MSC_i)^2 dx + \int_0^L (MSC_i)^2 dx} * \frac{\int_0^L (MSC_i)^2 dx}{\int_0^L (MSC_i^*)^2 dx} \right) \quad (6)$$

$$\beta_{ij} = \sum_{i=1}^{n} \left( \frac{(MSC_{ij}^*)^2 dx + \sum_{j=1}^{n} (MSC_{ij}^*)^2}{(MSC_{ij})^2 dx + \sum_{j=1}^{n} (MSC_{ij})^2} * \frac{\sum_{j=1}^{n} (MSC_{ij})^2}{\sum_{j=1}^{n} (MSC_{ij}^*)^2} \right) \quad (7)$$

Again, n is the total number of discrete segments that the structure has been split up into. Similar to Equation (5) described above the MSE may be used for example as described in Equation (8) to define a threshold for detecting damage to a structure.

3.1 Wavelet Transform Method

In contrast to the prior art techniques described supra in respect of FTM, MSC, MSE the methods according to embodiments of the invention exploiting wavelet transformation utilize a moving load as an input to an input/output technique. Accordingly, the inventors show that using the acceleration response of a structure to a moving load that it is possible to detect damage using a wavelet transform through a signal processing technique. Beneficially the method does not require any prior knowledge of the healthy state of the structure as with the other methods discussed supra. Accordingly, the Wavelet Transform Method (WTM) removes the requirement compare the intact and damaged states of the structure such as for example where either the difference between the two may be hard to observe or the undamaged state data does not exist such as with older structures, structures that have been repaired and no longer correspond to original design.

3.1 WTM Outline:

A wavelet is a waveform that has an average value of zero over its duration such as described in Equation (8) where $\psi(x)$ is a mother wavelet which can be translated and scaled to obtain the analyzing wavelets $\psi(x)_{\overline{xs}}$ as defined by Equation (9) where s is the scaling parameter and $\overline{x}$ represents the translation parameter. Accordingly, the continuous wavelet transform takes the form of Equation (10) where y(x) represents the original signal being analyzed and $Y(x,s)_W$ is the transformed quantity of the signal or the "wavelet coefficient".

$$\int_{-\infty}^{\infty} \psi(x) dx = 0 \quad (8)$$

$$\psi(x)_{\overline{xs}} = \frac{1}{\sqrt{s}} \psi\left(\frac{x - \overline{x}}{s}\right) \quad (9)$$

$$Y(x, s)_W = \int_{-\infty}^{\infty} y(x) \frac{1}{\sqrt{s}} \psi\left(\frac{x - \overline{x}}{s}\right) dx \quad (10)$$

In this manner wavelets may be exploited to detect singularities in signals using, for example, the following process. Initially the "mother" wavelet function is compared to a portion of the original time signal, from a device such as an accelerometer. From this comparison, the wavelet coefficient is calculated which is an indicator of how closely the mother wavelet is correlated with the portion of the signal in question. This process is repeated for the entire length of the signal. Then, the wavelet is scaled and the process is repeated such that a three-dimensional (3D) surface is created such as is depicted in FIG. 13 where the plot represents the wavelength coefficients for a moving load across a 10 meter (approximately 33 feet) long undamaged structure where the position on the horizontal axis represents the location of the moving load and the vertical axis the scale. The brightness (intensity) at any point is related to the wavelet coefficient such that higher wavelet coefficients are brighter. Higher scales, towards the upper portion of the graph, indicate slowly changing features and the coefficients associated correspond to low frequency content whilst lower scales, towards the bottom of the graph, indicate high frequency content. It is with this notion that high wavelet coefficients at a particular scale can be an indicator of frequency content of the signal at this time. Therefore it is possible to estimate the frequencies present in the signal, such as given by Equation (11) wherein the scale is related to a pseudo frequency.

$$F_S = \frac{F_C}{s\Delta} \quad (11)$$

where $F_S$ represents the pseudo frequency, $F_C$ is the center frequency of the wavelet used, s is the scale of the wavelet and $\Delta$ is the sampling frequency used.

Figure 14:
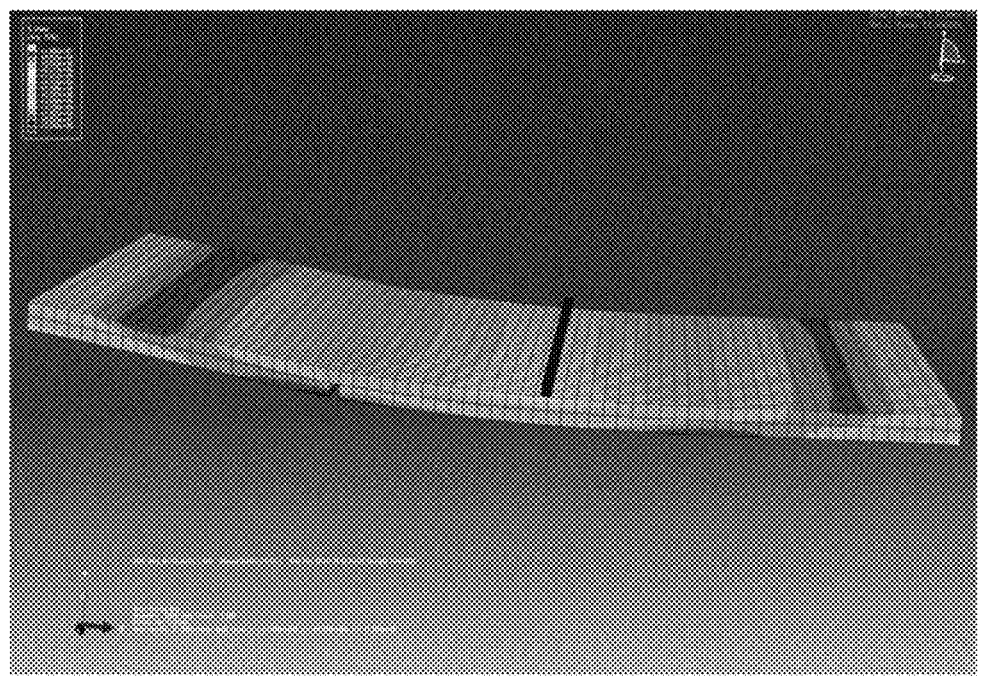
FIG. 14 depicts an ABAQUS simulation of a moving load traveling across a damaged concrete deck according to an embodiment of the invention.
Figure 15:
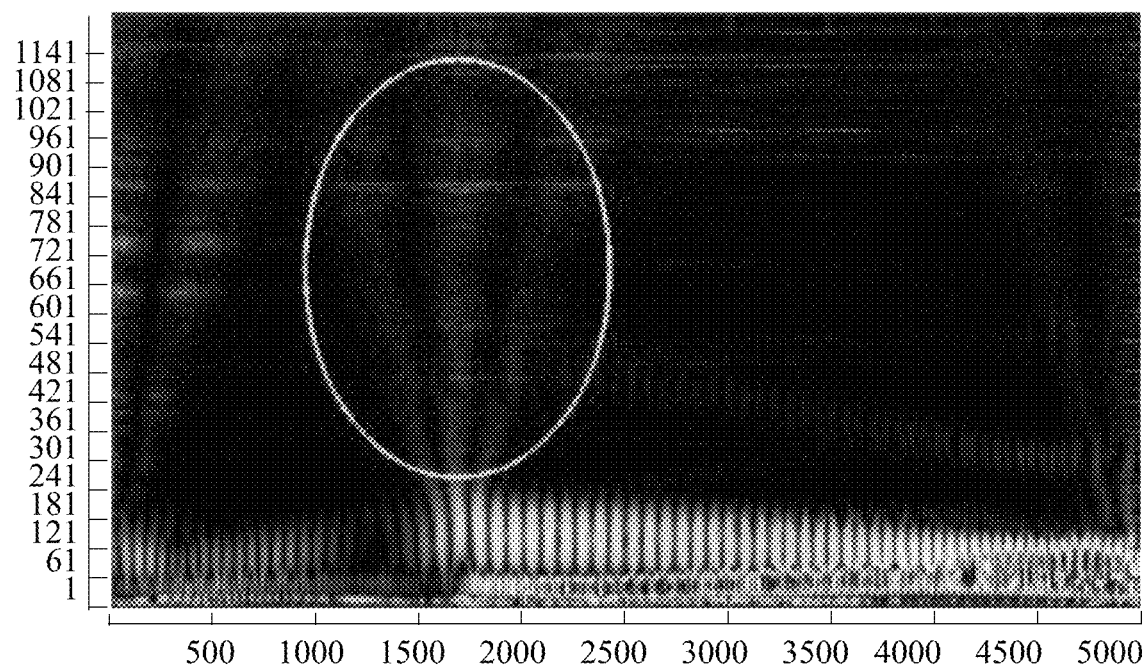
FIG. 15 depicts a 3D wavelet coefficient plot for damage located along the structure simulated in FIG. 13 according to an embodiment of the invention.

3.2 WTM Damage Detection:

Having established the WTM approach we now show how it can be applied to detect the damage in a concrete beam. Referring to FIG. 14 there is depicted a Finite Element (FE) simulation of a moving load traveling across a damaged 10 m×5 m×0.25 m (approximately 33'×16 ft×10") concrete deck as conducted in the ABAQUS Finite Element Analysis software suite. Within the simulation the damage was located a third (⅓) of the length of the beam. The results of this simulation are depicted in FIGS. 15 and 16 as 3D wavelength coefficient plot and 2D wavelet coefficient plot for scales 300-900 respectively.

As noted supra wavelet transforms are particularly useful for detecting singularities within a signal. Using this property of the wavelet transformation, the inventors proposed and have now demonstrated that it is possible to use measurements from an accelerometer to detect damage to a concrete structure both in respect of its existence but also location. Considering a moving load over a concrete structure then there are three response components:

Static: Response as if the load was moving across a 'healthy' structure incrementally ignoring the contribution of inertial forces of the bridge;

Dynamic: Vibrational response of the bridge; and

Damage: That portion of the static response due to the damaged portion of the structure.

Accordingly, as a moving load, such as a sky train car, truck, railway locomotive, etc. passes over a damaged part of the structure, a singularity is produced in the accelerometer signal which can be detected and isolated using the WTM approach. The static and damage components are very small compared to the dynamic response except when looking at the portion of the response far away from the main mode of vibration. Using Equation (13) and looking at FIG. 13, we can see that the main mode of vibration occurs at a pseudo frequency of 6.375 Hz. For the particular wavelet used the sampling frequency was chosen to be 0.002 s. A scale range well above the main mode of vibration must be chosen in order for the static and damaged portions to be more visible as is evident in FIG. 15. As evident from this figure the damaged location of the structure is successfully located at normalized position of x(t)=3.333. In order to observe more definable damage, scales well above those that correspond to the main mode of vibration must be chosen. As evident from FIG. 13 for the undamaged structure and FIG. 15 for the damaged structure the main mode of vibration is evident for scales be approximately 250.

Accordingly, scale of 300-900 were selected in order to produce the graph depicted in FIG. 16. Whilst FIGS. 15 and 16 were produced using a simple beam structure in which there was no noise and a significant amount of damage was introduced the contrast between scales 300-900 is high such that differentiation in real life situations can be obtained.

3.3 WTM Rebar Corrosion Detection

As noted supra in respect of WTM Damage Detection the method is capable of not only identifying that a structure has damage but also establishing a position along the structure wherein the damage is located. Accordingly, the inventors have extended this to the establishment of the detection of rebar corrosion within a concrete structure. As with the simulations supra these simulations were conducted using the ABAQUS Finite Element Analysis software suite and the wavelet transform was applied to the acceleration response of the structure to a moving load. The parameters for the simulations are given below in Table 1.

TABLE 1

Simulation Parameters

| | |
|---|---|
| Size of Concrete Deck | 10 m long × 5 m wide × 0.25 m thick |
| Concrete Density | 2400 kg/m³ (approximately 150 lb/ft³ |
| Concrete Poisson Ratio | 0.2 |
| Concrete Young's Modulus | 30 GPa |
| Concrete Young's Modulus | 20,000 kg (approximately 44,000 lb) |
| Speed of Moving Load | 1 m/s (approximately 3.6 km/h or 2.25 mph) |
| Sampling Rate | 500 Hz |
| Location of Damage | 3.33 m from left hand side of deck |
| Mother Wavelet Used | Bior6.8 |

In order to simulate corrosion within a concrete structure, two different models were created within ABAQUS. One was two piece model and the other a one piece model. For each model, the width of the corroded area was tested at 0.50 m and 0.25 m (approximately 20 and 10 inches respectively). The distance between the accelerometer and damaged area was also tested at 2.25 m, 4.00 m, and 6.00 m distances (approximately 7, 13, and 20 feet respectively). The latter pair corresponding approximately to accelerometers at either end of the structure from the location of the damage.

3.4 WTM One and Two Piece Model Description:

Within this model a concrete deck was explicitly separated into two separate parts, the healthy section of the concrete and the corroded section. Both sections were assigned the same concrete material properties as those shown in Table 1. A schematic of the two-piece model in ABAQUS is presented in FIG. 17. Within the two-piece model in order to simulate damage the sides of the interaction between the corroded and healthy sections were allowed to pass through one another. In contrast within the one-piece model depicted in FIG. 18 the entire concrete deck is simulated as being one continuous piece. However, different material properties are given to the corroded section relative to the un-corroded section. Table 2 outlines the material properties given to the corroded section within the one-piece model.

TABLE 2

Material Properties of Corroded Section

| | | | |
|---|---|---|---|
| Young's Modulus | $E_X$ = 3 GPa | $E_Y$ = 30 GPa | $E_Z$ 3 GPa |
| Poisson's Ratio | $V_{XY}$ = 0.02 | $V_{XZ}$ = 0.20 | $V_{YZ}$ = 0.02 |
| Shear Modulus | | $G_{XY} = G_{XZ} = G_{YZ}$ = 1 GPa | |

3.5 WTM Two-Piece Model Simulation Results

Referring to FIG. 19 the acceleration response due to moving load from a measurement point 6 m away from damage for the two-piece model is displayed for the case wherein the damaged area width was 0.25 m. Accordingly, from this acceleration data collected from the measurement point the two dimensional wavelet energy graph can be computed as shown in FIG. 20. The corresponding two dimensional wavelet energy graph from the acceleration data of the 0.5 m damaged section case is shown in FIG. 21. In addition to the damaged section being identified at the appropriate location in each simulation it can be seen that the magnitude of the peak does not significantly change with damage.

3.6 WTM One-Piece Model Simulation Results

Referring to FIG. 22 the acceleration response due to moving load from a measurement point 4 m away from damage for the one-piece model is displayed for the case wherein the damaged area width was 0.25 m.

Figure 25:
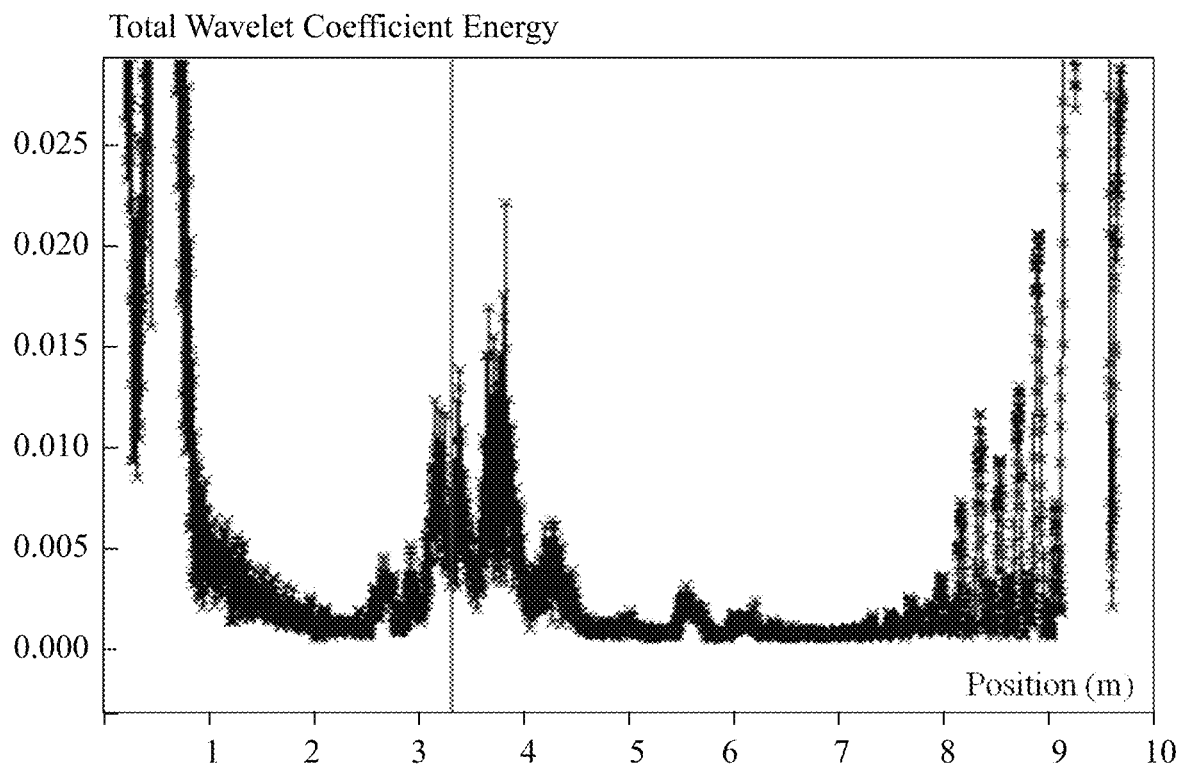
Figure 26:
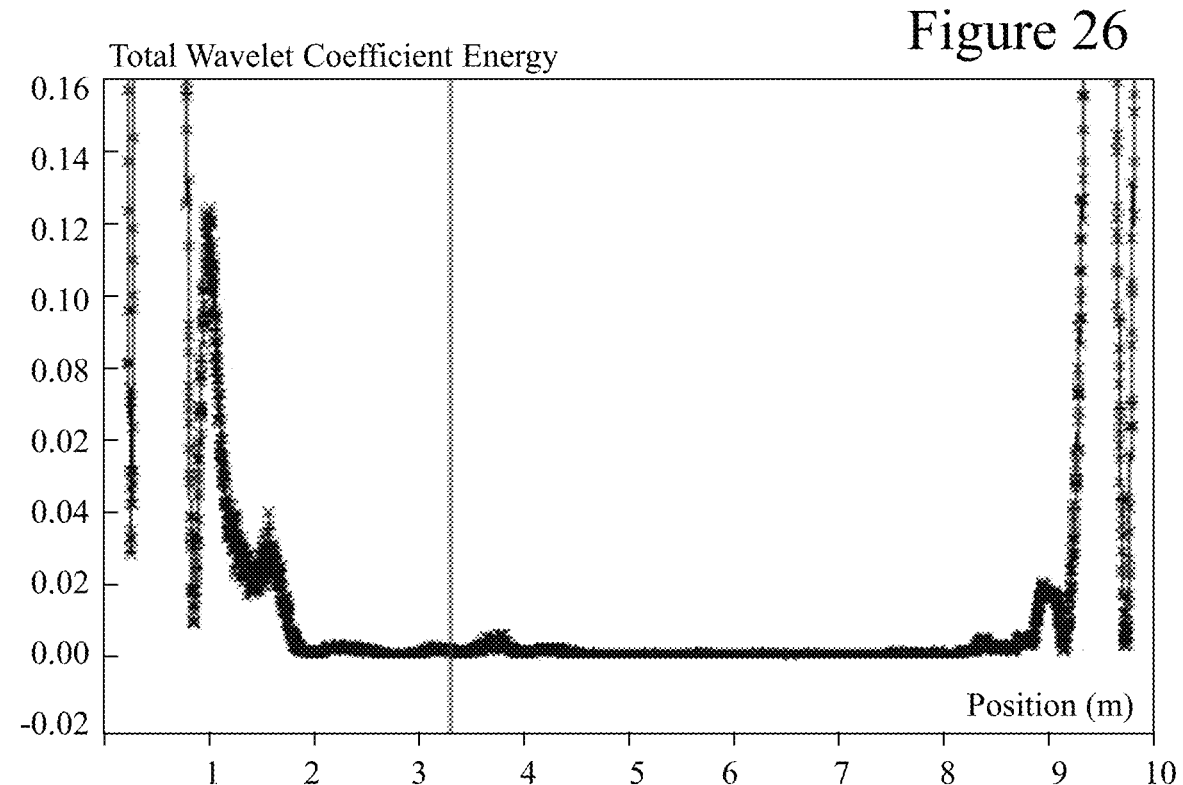
FIGS. 26 to 28 respectively depict 2D wavelet energy plots for measurements points 6 m, 4 m and 2.25 m respectively away from a damaged region of width 0.50 m according to an embodiment of the invention.
Figure 27:
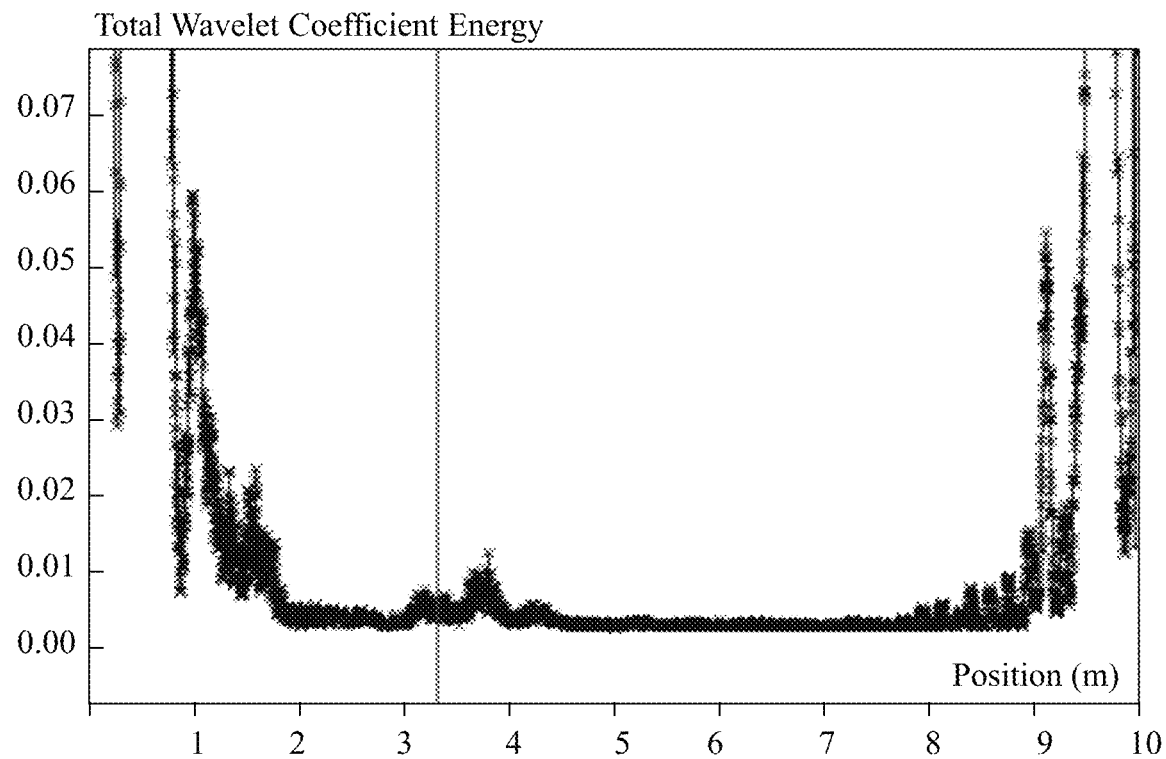
Figure 28:
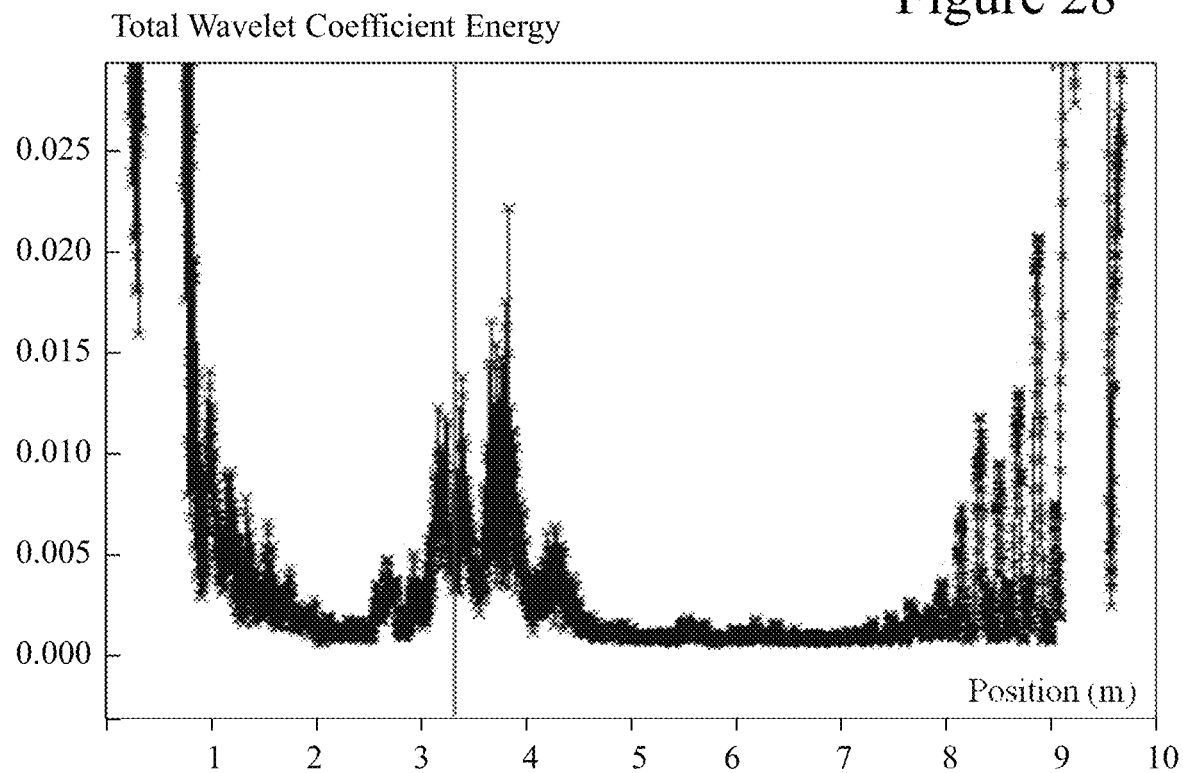

3.7 WTM Two-Piece Model Simulation Results with Varying Damage-Measurement Separation Referring to FIGS. 23 through 25 there are depicted two-dimensional wavelet energy plots from measurements points placed at varying distances from damage of 6 m, 4 m, and 2.25 m respectively (approximately 20, 13, and 7 feet respectively). FIGS. 26 through 28 depict the corresponding two-dimensional wavelet energy plots for the same damage—accelerometer configurations but now with the damage width of 0.5 m. In each of FIGS. 23 through 28 the vertical line indicates the location of damage. As noted with respect to FIGS. 20 and 21 and comparing similar separation simulation results, such as for example FIGS. 25 and 28 at 2.25 m separation, the height of the wavelet transform coefficients does not substantially change.

Accordingly, it would be evident to one skilled in the art that one or more accelerometers appropriately disposed upon or within a structure may provide the required acceleration data, such as that depicted in FIGS. 19 and 22. This data may then be processed using an automated wavelet transform process on a local or remote computer system to generate the appropriate three-dimensional and two-dimensional wavelet energy plots such as those depicted in respect of FIGS. 13, 15, 16, 20-21, and 23-28 respectively which may then be characterised, measured, analysed, stored, and assessed. These three-dimensional and two-dimensional plots and results derived therefrom may then be assessed by engineers or automatically characterised.

It would be evident that under different scenarios the accelerometers may be temporarily disposed upon or within the structure to be assessed or permanently disposed upon or within it. Consider, a first scenario wherein a plurality of accelerometers are disposed along the length of a bridge by a technician and an 18-wheeler truck of known weight is then driven at a predetermined speed across the bridge. Such an operation would close the bridge for a short period of time before the bridge was re-opened to traffic. In another scenario the plurality of accelerometers are disposed along the length of a bridge permanently or for an extended period together with a field deployable weigh bridge(s) wherein normal traffic would flow across the bridge with continuous data storage from the accelerometers and weight bridge(s).

Accordingly, defined discrete events of known load may be identified where the load is the only traffic across the bridge during the measurement allowing these corresponding accelerometer data to be used. In such a manner a structure may be periodically monitored without requiring the deployment of personnel and other resources such as traffic police, police, etc. In other scenarios the actual weight of the object may not be an important parameter except that the load moving exceed a predetermined minimum weight and be travelling within a predetermined speed range. In other scenarios a load may be characterised at a periodic weigh station and tracked through GPS location based services such that should the load may be correlated temporally and spatially to the event used in the wavelet analysis.

4. Automated Visual Inspection During Operational Lifetime of Concrete Structure Within the embodiments of the invention described supra in respect of FIGS. 12 through 28 concrete structures may be assessed in respect of damage through an automated process exploiting moving loads and wavelet transformations/analysis. As noted the damage may arise from a variety factors including a localized change in concrete parameters as the result of corrosion. In addition to such physical damage determination through such wavelet transformation analysis it may be beneficial to provide engineers and others with visual information relating to concrete structures.

4.1 Automated Visual Inspection

Figure 29:
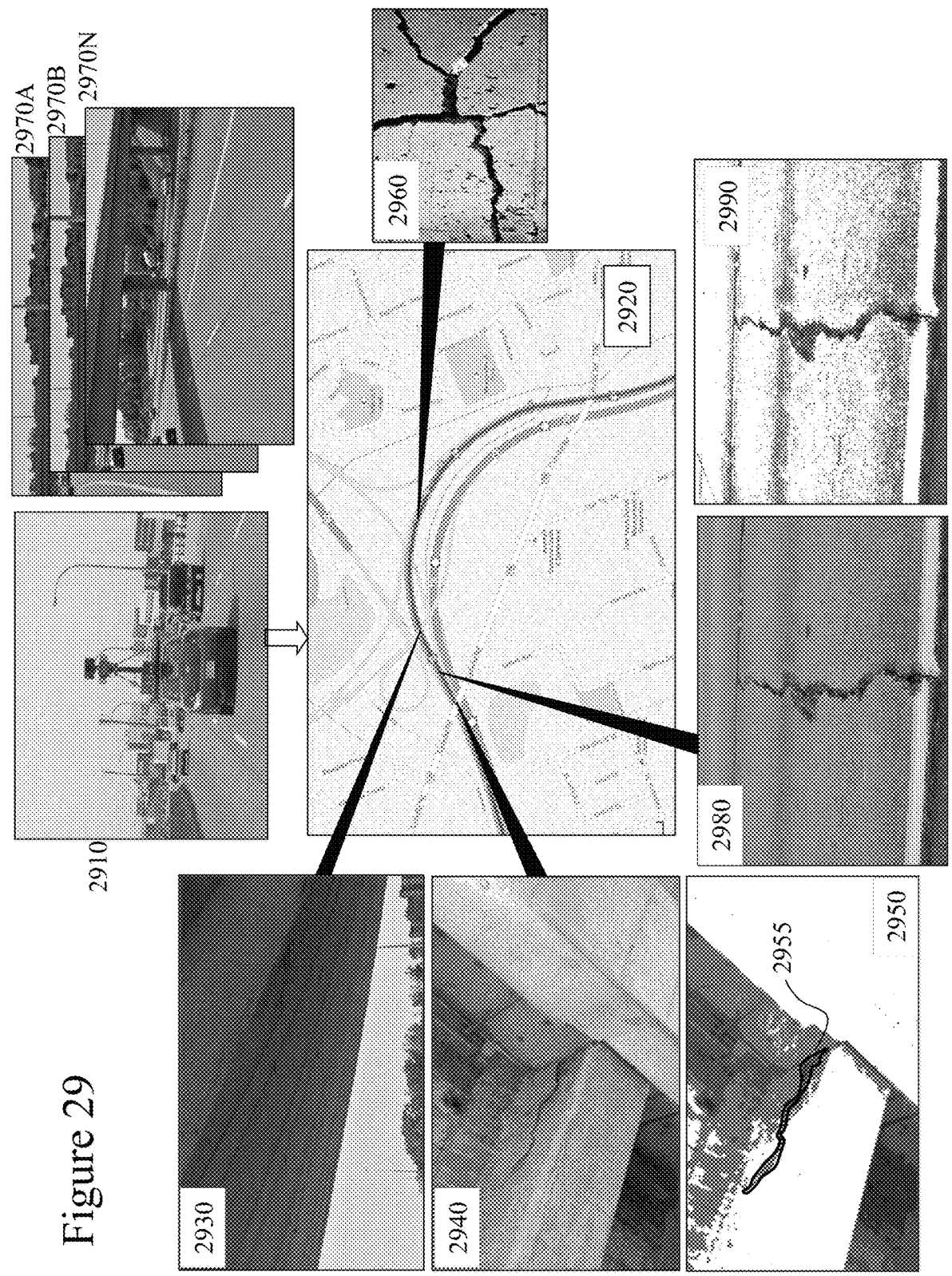
FIG. 29 depicts a mobile data acquisition system according to an embodiment of the invention for automatically detecting, categorizing and logging defects within concrete structures.

Accordingly in FIG. 29 a Vehicle 2910 is dispatched incorporating a data acquisition system which may, for example, be one or more digital image acquisition systems operating in the normal human visual range but may include others operating, for example, in the near infra-red, ultra violet, far infra-red, X-ray and terahertz regions of the electromagnetic spectrum. The Vehicle 2910 follows a Route 2920 along one or more roads acquiring a plurality of images from the one or more digital image acquisition systems which are temporally and spatially tagged, e.g. using GPS or another triangulation method such as wireless access points. Said digital image acquisition systems may be directed in different directions including towards the road surface, along the highway, angled down towards highway surface, up, to the left, to the right, and angled up away from highway surface. In this manner multiple perspectives may be obtained on damage or other features.

Accordingly, as the Vehicle 2910 traverses the route it captures a series of images 2970A . . . 2970N which are then stored together with metadata including, but not limited to, time, location, temperature, weather, and vehicle identity. These may then be associated through geographic data including, but not limited to, mapping data and municipal infrastructure data, to particular elements of infrastructure such as First Image 2930 to "Aviation Parkway East—Highway 417 West Overpass" and "Second Image 2940 to "Cyrville Road—Highway 417 West Overpass." Images may then be processed using one or more software algorithms in order to isolate, highlight, and classify defects observed within infrastructure elements including, but not limited to, the road surfaces, walls, bridges, overpasses, tunnels, and underpasses. For example Third Image 2960 shows extraction of damaged concrete from an image acquired at coordinates +45° 25' 23.52"N, −75° 37' 5.29"W as well as Fourth Image 2980 at location +45° 25' 21.43"N, −75° 37' 25.26"W. It would be evident that with a combination of such automated visual inspection and WTM structure condition measurements that damage may be assessed with improved accuracy as to impact. Hence, a crack within the road surface such as that within Fourth Image 2980 may in some instances when observed on the road surface of a concrete bridge for example be merely surface damage whilst in another instance the surface damage may be correlated to a location of damage within the structure from the WTM analysis.

In other instances the images are processed to highlight features such as depicted in Fifth and Sixth Images 2950 and 2960 respectively wherein digital image processing has been used to remove image content and accentuate the damaged region(s) within the image. In Fifth Image 2950 a combination of image processing and edge detection have been employed to yield highlight 2955 wherein in Sixth Image 2990 only image processing has been employed. It would be evident that in some embodiments of the invention these images may be obtained using infrared imaging, or other non-visible ranges, in combination with or in isolation of visual images. Similarly, in other embodiments the spectral characteristics of the overlaying concrete, asphalt etc., layers to the underlying base and sub-base materials may be exploited with or without illumination to determine whether damage has penetrated different depths and accordingly have different priorities and/or repair requirements. For example, a large number of shallow damage sections may have a lower priority than a single deep damaged section that has exposed the rebars within the structure or has propagated through the highway surface for example.

4.2 Automated Inspection Reporting

Figure 30:
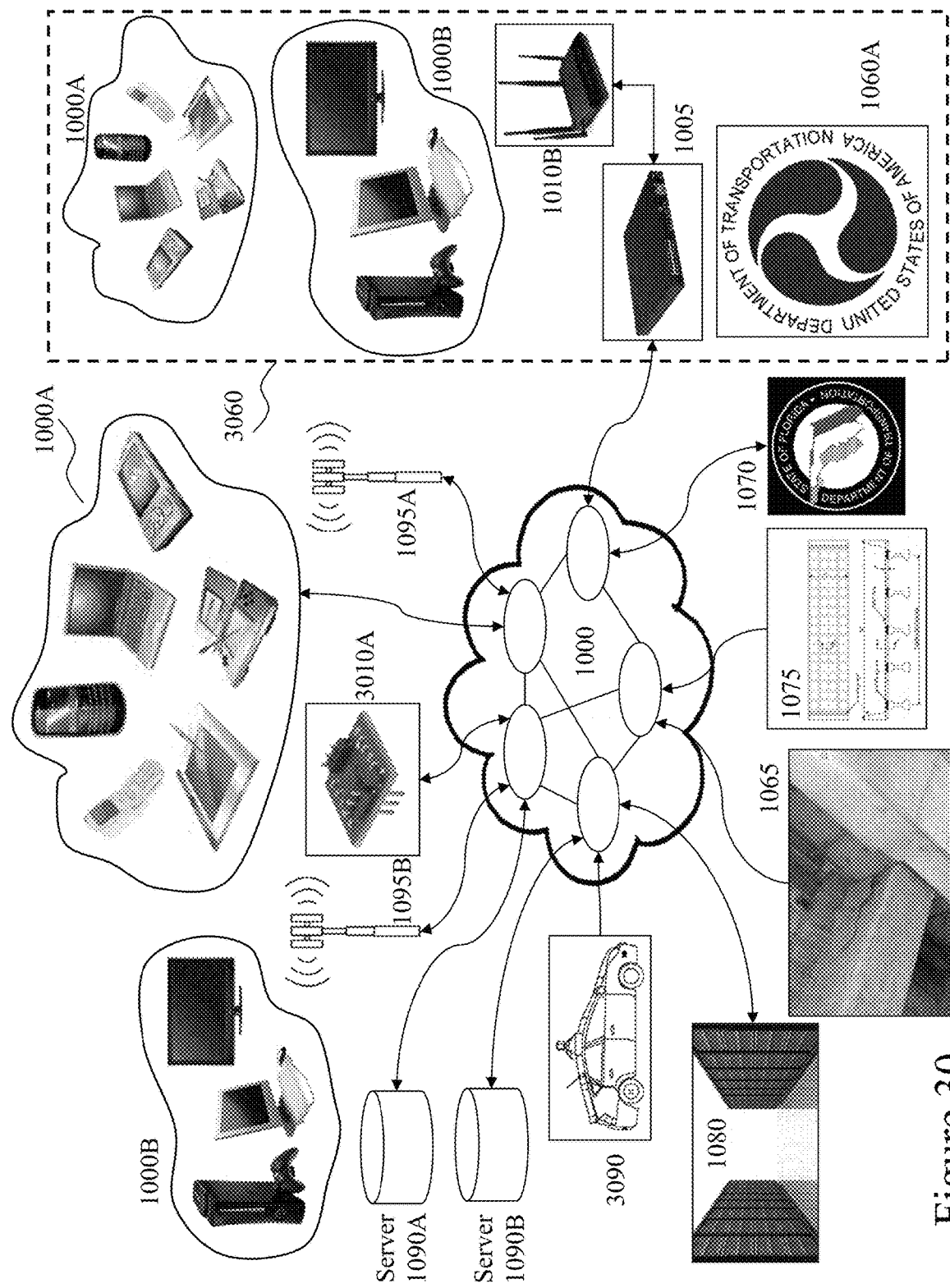
FIG. 30 depicts a network supporting communications to and from electronic devices, sensors, and organizations according to embodiments of the invention.

Now referring to FIG. 30 there is depicted a Network 1000 supporting communications to and from electronic devices acquiring, storing, analysis, and presenting data relating to infrastructure characteristics such as damage according to embodiments of the invention. As depicted the overall structure in FIG. 30 is similar to that shown in FIG. 10 except that also connected to Network 1000 is Vehicle 3090 which may, for example, be one performing the mapping of infrastructure such as described in respect of FIG. 29 and accordingly the acquired image data may be transmitted continuously and/or periodically through Network 1000 for storage/analysis/assessment/archiving etc. Alternatively Vehicle 3090 may be the vehicle providing the moving input to the structure in respect of FIGS. 13 through 28 described above and the WTM method of determining the location of damage. Vehicle 3090 may in this instance simply transmit data such as velocity, location, and time to the Network 1000 for storage/analysis/assessment/archiving in combination with the data acquired from the one or more Accelerometers 3010A which may be deployed permanently or temporarily upon the structure.

With low cost integrated circuit accelerometers exploiting silicon microelectromechanical structures (MEMS) these may be packaged to provide low cost permanently deployed accelerometers such as Accelerometers 3010A. Accordingly, in some embodiments of the invention the Accelerometers 3010A may contain only short-range wireless communications and be powered through solar cells such that they only communicate their data to the Vehicle 3090 when it is within range periodically or aperiodically. Vehicle 3090 then may combine this data together with that it acquires regarding location, speed, time, etc. to provide a combined record of a structure characterization. In this manner a truck configured to be essentially loaded over one axle may be driven around the highways and automatically acquire data for each bridge it travels over whilst one or more police vehicles may be employed to stop and hold traffic for a short period of time whilst the Vehicle 3090 traverses the structure.

Accordingly, it would be evident to one skilled in the art that data acquired and/or acquired relating to infrastructure damage and/or integrity according to embodiments of the invention described supra in respect of FIGS. 13 through 29 may be connected to a communications network such as Network 1000 either continuously or intermittently and accordi77ngly stored, analysed, retrieved etc. It would be further evident that the infrastructure damage and/or integrity together with the analysis of the measurements and their mapping may be triggered as a result of activities triggered by, for example, the Government Body 3060A and/or State Body 3070 in order to address regulatory requirements, safety concerns etc.

4.3 Smart Data Collection

According to embodiments of the invention the data collection for automated inspection, monitoring, and regulatory compliance/management of concrete structures may include, in addition to the features described and discussed elsewhere within this specification, features such as:

GPS Activation for the initiation of image collection automatically wherein the collection of images from a portable/mobile data collection system, such as Vehicle 2910 in FIG. 29 or Vehicle 3090 in FIG. 30, is automatically triggered based upon the GPS coordinates of the portable/mobile data collection system being within a predetermined offset from a value stored within a database. Such a database of GPS coordinates may be established for example by a regulatory authority, a municipality, or Government organization.

Gravity-based unit to automatically measure a distance for a surveyor, monitoring system, etc. wherein the portable/mobile data collection system as it travels across a concrete structure performing measurements automatically determines the distance travelled in isolation based upon the number of rotations of a wheel calculated by the number of changes in the gravity direction obtained using the installed sensor on the wheel forming part of the portable data collection system in contact with the surface of the concrete structure.

Stereo vision imaging using optical, ultrasound, radiofrequency, laser, etc. in isolation or in combination may be employed to provide perspective to the captured images as part of a portable/mobile data collection system according to an embodiment of the invention. Within an embodiment of the invention a stereo camera may be implemented using a single or double lens and single or double camera in combination with a mechanical or electro-optic switching mechanism such that the switching mechanism occludes sequentially each of the left and right halves of the lenses so that the cameras sequentially captures a left and right image perspectives.

Infra-red imaging may also be employed to detect areas of delamination within a portable/mobile data collection system according to an embodiment of the invention. For example, broadband, narrowband and multi-band thermal imaging may be employed as part of the portable/mobile data collection system either discretely or in combination with infra-red illumination/heating/scanning.

4.4 Advanced Image Processing Algorithms

According to embodiments of the invention the processing of images acquired for automated inspection, monitoring, and regulatory compliance/management of concrete structures may include, in addition to the features described and discussed elsewhere within this specification, features such as:

Stitching 3D panoramic/captured images collected for bridge inspection, wherein 3D panoramic images and/or captured images are digitally merged using advanced feature matching algorithms to form a continuous image of the concrete structure.

Detect presence of damage through processing of acquired images from a portable/mobile data collection system based upon, for example, characteristics of cracks relative to features of the concrete structure or comparison of acquired images with images acquired at completion of concrete structure.

Detect type of damage through processing of acquired images from a portable/mobile data collection system based upon characteristics of damage, e.g. cracks, spalling, and rust staining all present differently within acquired images.

Detect cause of damage through processing of images acquired from a portable/mobile data collection system, e.g. determining from the pattern of a crack whether it arose from Alkali-Silica reactions or corrosion, for example.

Measure the lateral dimensions, e.g. length and width of a crack or the area of spalling, based upon the acquisition of images with known zoom (see section 4.9 below) by the portable/mobile data collection system.

Measure the depth of features such as cracks, spalling, etc. through algorithmic processing of depth within flash-generated shadows in the spalled/crack areas knowing the angle of the flash and scale of the image(s) (see section 4.9 below) acquired by the portable/mobile data collection system.

Automatic assignment of damage classification based on a specific standard dataset of images containing defined features, e.g. spalling, and processing acquired images against these standard datasets for correlation.

4.5 Smart Data Management

Automatic alarm notification related to the status of a bridge by comparing the growth of crack or increase in size of spalling or rust stains between various inspections, which have been time stamped by the portable/mobile data collection system and have known scale to define a limit at which the alarm is triggered or define multiple limits at which different alarms are triggered. For example, a first alarm may be triggered notifying the infrastructure owner that an issue requires addressing whilst a second alarm may be triggered if the detected defect has not been addressed on a subsequent measurement or the determined defect requires that other action be taken requiring regulatory/Government input and/or action. For example, a small crack may require a municipality repair it whilst a large crack may require a State/Provincial regulatory and/or control body to limit traffic, axle weight, etc. until further analysis and/or correction is performed.

4.6 Automated Traffic Management

Automatic traffic-control during the bridge inspection allowing an inspector and/or portable/mobile data collection system to control traffic during an inspection automatically in combination with smart signs without requiring a support team to manually control traffic. For example, using smart signs that communicate with each other and through image processing determine whether there are queues either side and/or measure or estimate the number of vehicles within these to make decisions such that traffic management adapts to the actual scenario rather than being simple timed prior art systems and/or manned at either end. Optionally, such a smart signage system may be controlled via an application installed upon a PED such as that within the portable/mobile data collection system or that belonging to the inspector. Optionally, a system according to an embodiment of the invention may combine optical image techniques together with other sensors such as those counting the number of vehicles that have passed e.g. through laser based systems, surface deployed pressure tube systems, and/or image processing.

Accordingly, a single inspector may establish and manage a traffic flow/control system either prior to or during operation of a portable/mobile data collection system for example to acquire the required data. Further such a system may determine the presence of an articulated tractor trailer, establish the identity of the tractor trailer through pattern recognition/feature extraction of the registration, control the traffic such that the truck passes on its own, capture data during the tractor trailer crossing the bridge, for example, and transmit the data to remote server(s) for processing via wavelet analysis such as described supra wherein the tractor trailer data is employed to cross reference load weigh station data for the loading of the tractor trailer. Optionally, if the registration does not provide current load weigh station data for the tractor trailer then the automated system does not perform such a controlled roll of the tractor trailer over the concrete structure.

4.7 Mounted Display Visual Inspection

According to embodiments of the invention a portable/mobile data collection system may operate in conjunction with head mounted display and/or vision augmentation devices, e.g. Google Glass, on drones either remote-controlled or programmed, for example, for a path of inspection around a suspension bridge, as well as on robots for inspection of tunnels, pipelines to provide an operator/inspector with eyewear-assisted or remote-vision applications and features for visual inspection as well as providing communication with non-destructive testing probes, systems, etc. Accordingly, the operator/inspector may, for example, be presented with an overlay of the infra-red imaging with their view so that they may, for example, associate elements within both as they view them. Such associations from an inspector may be logged, analysed and used as part of learning networks/algorithms to improve the determination/classification of damage observed subsequently.

4.8 Wireless Half Cell

Within the descriptions of the prior art supra in FIG. 3 with deployment 330 a half-cell requires that electrical connections be made from the electrical voltmeter/multimeter to the half-cell reference electrode and rebar. However, according to an embodiment of the invention established by the inventors this electrical connection requirement is removed. Accordingly, sensors on the rebar and surface of the concrete are linked to one another or to a portable/mobile data collection system or a remote server. Within an embodiment of the invention a wireless link couples the sensor on the rebar to a sensor coupled to the concrete incorporating a half-cell, such as half-cell 310B.

Optionally, an embodiment of the invention may exploit one or more additional half-cells including, but not limited to, aqueous reference electrodes (e.g. standard and/or normal hydrogen electrode, palladium-hydrogen, etc.), non-aqueous reference electrodes, pseudo-reference electrodes, and quasi-reference electrodes.

4.9 Laser Assisted Scaling

Within embodiments of the invention images taken by smartphone or tablet forming part of a portable/mobile data collection system wherein, for example, a laser based grid may be projected onto the concrete surface from a laser based generator attached to the smartphone, tablet, and/or system capturing the image and/or a laser based system attached to the smartphone, tablet, and/or system capturing the image of the concrete surface so that the scale and distance may be determined automatically based upon the known characteristics of the camera and the optical pointing devices.

Such a laser assisted scaling and distance determination is required as the dimensions of objects in optical two-dimensional (2D) images cannot be easily determined without having additional information about the third dimension of the image. One technique to reconstruct a three-dimensional (3D) image of a scene is to use two cameras looking at the scene from two slightly different angles or as described supra in respect of an embodiment of the invention exploit a single camera with electro-optic switch to sequentially capture the two different angles. This technique is known as stereo vision and is currently used in many products and applications but suffers in that it requires extensive post-processing and computation effort.

Figure 32:
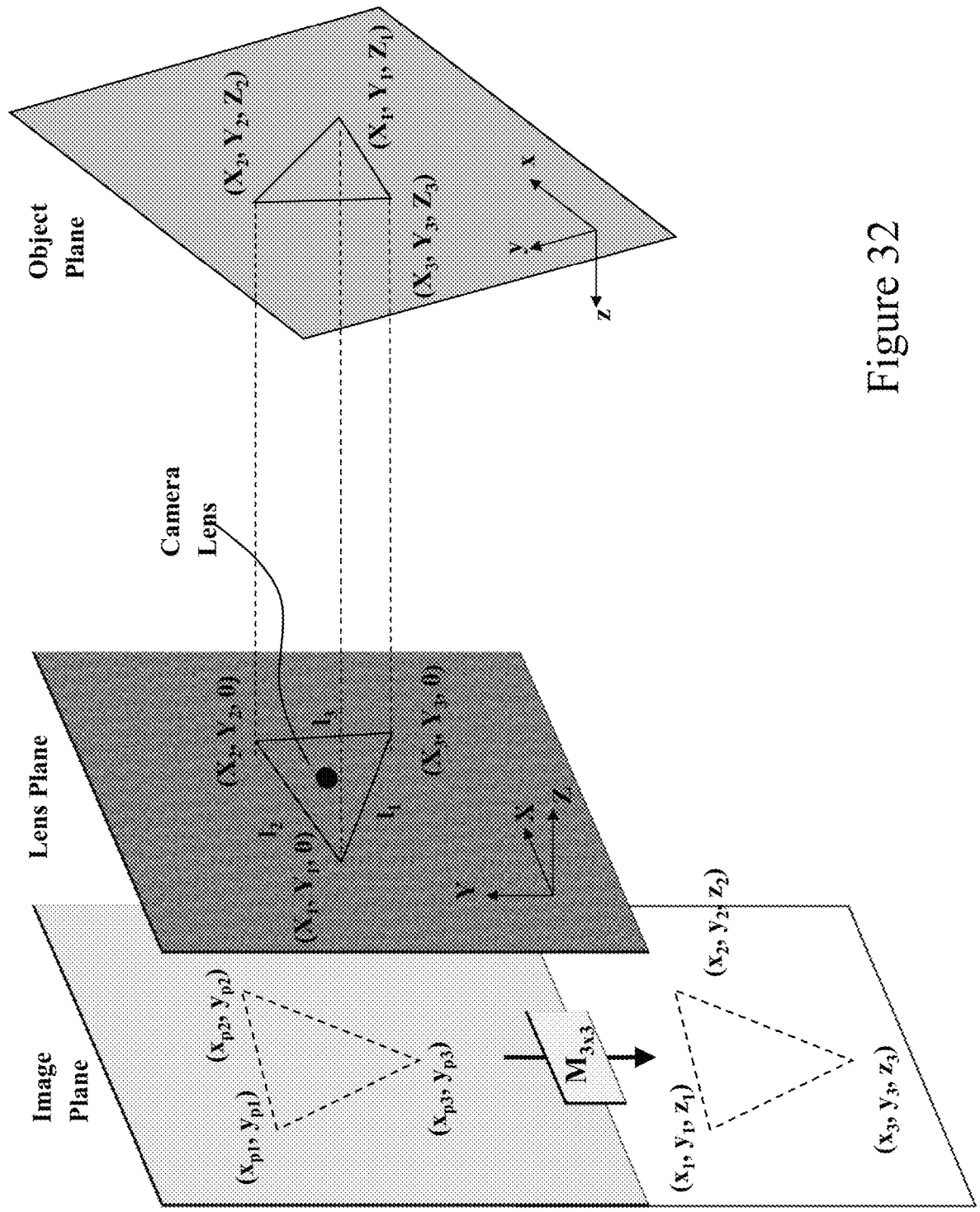
FIG. 32 depicts imaging scaling using optical pointing according to an embodiment of the invention.

However, according to an embodiment of the invention the inventors obtain the dimensional information as well as distance from the camera to a scene from the 2D image by reflecting at least 3 laser points from the scene. Within the ensuing description of the principle reference should be made to FIG. 32 which also depicts the principle of transforming to determine scale and distance according to an embodiment of the invention. Accordingly, in this embodiment with three laser points parallel to each other wherein the beams of these three laser points are reflected on the scene object. As the three lasers are affixed to the PED and/or portable/mobile data collection system then the distances between these points at the source are known and constant. For each point $$\begin{bmatrix} x_P \\ y_P \end{bmatrix}$$

in the image then we have a point in the image plane in the Cartesian coordinate $$\begin{bmatrix} x_n \\ y_n \end{bmatrix}$$

as determined by Equation (12) wherein $M_{3\times3}$ is a 3×3 conversion matrix that be defined by the specification of the camera, such as its focal length, and can be defined through a calibration process. Accordingly, $x_p$ and $y_p$ are in pixels such that $x_n$ and $y_n$ are defined by Equations (13A) and (13B) respectively where $X_n$, $Y_n$, $Z_n$ are the world coordinates of the point in the Cartesian coordinate system.

$$\begin{bmatrix} x_P \\ y_P \\ 1 \end{bmatrix} = M_{3\times3} \cdot \begin{bmatrix} x_n \\ y_n \\ 1 \end{bmatrix} \tag{12}$$

$$x_n = \frac{X_n}{Z_n} \tag{13A}$$

$$y_n = \frac{Y_n}{Z_n} \tag{13B}$$

Accordingly, for the three laser points within the image we have coordinates as defined in Equations (14A) to (14C) wherein we can find $x_1$, $x_2$, $x_3$, $y_1$, $y_2$, $y_3$ from Equation (14) using the locations of the laser points on the image. The goal is to determine the values for $X_1$, $Y_1$, $Z_1$, $X_2$, $Y_2$, $Z_2$, $X_3$, $Y_3$, $Z_3$ which provide the real world coordinates of the laser points on the object. Given that the distances between the three laser points are constant, and defined by $l_1$, $l_2$, $l_3$ from the first, second, and third lasers to the second, third and first lasers respectively then Equations (15A) to (15C) are correct.

$$x_1 = \frac{X_1}{Z_1}, y_1 = \frac{Y_1}{Z_1} \tag{14A}$$

$$x_2 = \frac{X_2}{Z_2}, y_2 = \frac{Y_2}{Z_2} \tag{14B}$$

$$x_3 = \frac{X_3}{Z_3}, y_3 = \frac{Y_3}{Z_3} \tag{14C}$$

$$(X_2 - X_1)^2 + (Y_2 - Y_1)^2 = l_2^2 \tag{15A}$$

$$(X_3 - X_1)^2 + (Y_3 - Y_1)^2 = l_1^2 \tag{15B}$$

$$(X_2 - X_3)^2 + (Y_2 - Y_3)^2 = l_3^2 \tag{15C}$$

By substituting Equations (14A) to (14C) into Equations (15A) to (15C) then we obtain Equations (16A) to (16C)

$$(x_2 Z_2 - x_1 Z_1)^2 + (y_2 Z_2 - y_1 Z_1)^2 = l_2^2 \tag{16A}$$

$$(x_3 Z_3 - x_1 Z_1)^2 + (y_3 Z_3 - y_1 Z_1)^2 = l_1^2 \tag{16B}$$

$$(x_2 Z_2 - x_3 Z_3)^2 + (y_2 Z_2 - y_3 Z_3)^2 = l_3^2 \tag{16C}$$

Accordingly, Equations (16A) to (16C) provide three equations for the three unknown parameters that can be solved numerically or analytically. Using Equations (14A) to (14C) $X_1$, $Y_1$, $X_2$, $Y_2$, $X_3$, $Y_3$ can also be determined. As a result, the equation of a plane passing through the three laser points can be obtained knowing their Cartesian coordinates, Equation (17) and then the distance between any two points (Point A and Point B) on this plane can be determined from pixel distance between two points on the image as given by Equations (18A) to (19).

Accordingly, substituting Equations (18A) to (18C) into Equation (17) yields Equation (21) from which $Z_n$ and accordingly $X_n$ and $Y_n$ can be calculated. The parameter Zn provides us the distance from the camera to the object, and $X_n$, $Y_n$, and $Z_n$ data of those two points can be used to measure the distance between the two points.

$$aX + bY + cZ + d = 0 \tag{17}$$

$$\begin{bmatrix} x_P \\ y_P \end{bmatrix} \xrightarrow{M_{3\times3}} \begin{bmatrix} x_n \\ y_n \end{bmatrix} \tag{18A}$$

$$X_n = x_n Z_n \tag{18B}$$

$$Y_n = y_n Z_n \tag{18C}$$

$$a \cdot x_n Z_n + b \cdot y_n Z_n + c \cdot Z_n + d = 0 \tag{19}$$

Accordingly, images acquired by an_portable/mobile data collection system may be defined by a scale allowing measurements of defects, cracks, spalling, etc. as well as allowing the scaling of multiple images to be performed for a combining process to generate larger views of the concrete structure, etc. as well as stitching sequential images or images acquired over a period of time.

5. Hand-Held Non-Contact Corrosion and Rebar Detection Technology

Figure 31A:
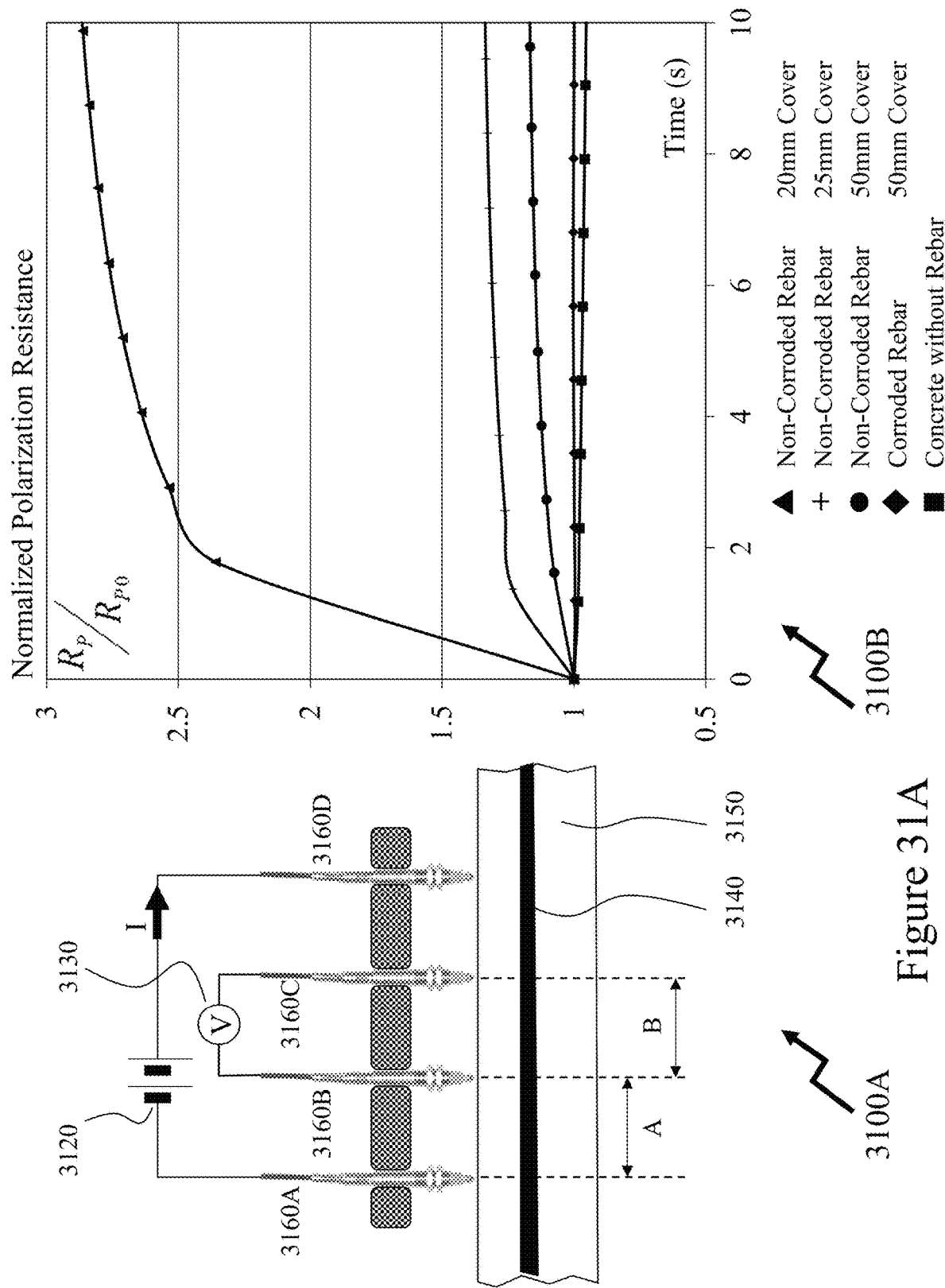
FIG. 31A depicts non-contact electrical characterization of corrosion and rebar presence within concrete according to an embodiment of the invention.

Referring to FIG. 31 there are depicted first and second images 3100A and 3100B respectively with respect to a non-contact electrical characterization of corrosion and rebar presence within concrete according to an embodiment of the invention. Accordingly, as depicted in first image 3100A of FIG. 31 the electrical response of rebar inside the concrete is determined from the surface of the concrete with four probes without an electrical connection to the rebar within the concrete. Accordingly, there are depicted four probes 3160A to 3160D in an electrical configuration similar to that of a prior art 4-point Wenner probe in that the outer pair of probes 3160A and 3160D respectively apply a signal and the inner pair of probes 3160B and 3160C measure the resulting potential difference between them via voltmeter 3130. However, in contrast to the prior art wherein the signal applied across the outer pair of probes 3160A to 3160D is an AC signal, typically at 40 Hz, the inventors have replaced this with a DC current source 3120.

Within the prior art a 4-point Wenner probe, wherein all probes are equally spaced, or a 4-point Schlumberger probe, wherein the spacing of the outer probes from the inner probes is equal but different to the separation of the inner probes, is employed to measure the electrical resistivity of concrete. However, rebar(s) within the concrete can disturb the electrical resistivity measurements and accordingly the recommended measurement orientation of the 4-point Wenner/Schlumberger probes is determined by the spacing of the rebars as ideally the orientation is diagonal to the square matrix of rebars but if this not possible then the orientation should be perpendicular to the rebar. However, in the majority of structures these orientations and spacings are at best approximate and generally assumed relative to the portion of the concrete structure being measured.

However, using the DC current source 3120 according to embodiments of the invention the inventors have established the ability to determine the presence of a rebar and/or its corrosion state based upon the temporal evolution of polarization resistance determined from the measured signals as indicated in second image 3100B in FIG. 31. Referring to second image 3100B it can be seen that for non-corroded rebar the evolution of the normalized polarization resistance is positive and the ratio after even only a couple of seconds is greater for rebars that are closer to the surface of the concrete. In contrast, the slope for a corroded rebar is close to zero for the same depth of rebar and also reduced in percentage deviation. A reference measurement of polarization resistance ratio in the absence of rebar within concrete is also depicted with a small negative slope.

The polarization resistance of rebar in concrete from the surface can be determined using Equation (20) wherein $R_P(t)$ is the polarization resistance of the rebar and concrete system, $V(t)$ is the potential measured at the two inner electrodes and $I(t)$ is the current applied at the two outer electrodes. $R_{P0}$ is the polarization resistance of the system at time zero.

$$R_P(t) = \frac{V(t)}{I(t)} \qquad (20)$$

As noted supra the relative polarization resistance of the reinforced concrete system, $R_P(t)/R_{P0}$, measured from the surface of concrete changes with time and depends upon the location and diameter of the rebar in the concrete as well as its corrosion condition, i.e. presence, severity and rate of corrosion. By decreasing the cover thickness of the concrete over the rebar then the increase in $R_P(t)/R_{P0}$ increases for non-corroding rebar. However, for a corroded rebar $R_P(t)/R_{P0}$ does not change significantly, and in fact is almost constant with no significant change.

This behavior is related to the polarization resistance of the passive film wherein the polarization resistance of rebar in concrete in the passive state (none-corroding condition) is much higher than that of the corroding rebar. As a result, for a corroding rebar, a portion of the current paths are through the rebar reinforcement as there is a little resistance on the surface of rebar against current flow. However, in the case of passive, non-corroded, rebar because of the high polarization resistance of the passive layer on the surface of the rebar the current passage through the rebar would be very limited, and therefore, increases over time as a result of polarization, i.e. charge of double layers of capacitors. Accordingly, the DC 4-probe measurement concept established by the inventors can be used to detect rebar corrosion from the surface of concrete without requiring any electrical connection to the rebar unlike other corrosion detection techniques in the prior art.

This method according to embodiments of the invention is also applicable to various types of rebar including, but not limited to, epoxy-coated rebar, stainless steel rebar, and galvanized steel rebar. Unlike other corrosion measurement techniques such as half-cell corrosion potential, linear polarization and galvanostatic pulse technique, this method is sensitive to the direction of rebars crossing each other. By changing the direction of the probe with respect to the reinforcement mesh then the measurement can detect the condition of only the rebar parallel to the direction of the measurement. Accordingly, the DC 4-probe technique can be used initially to verify that the thickness of concrete over the rebar within a new concrete structure meets the design requirements as the magnitude of $R_P(t)/R_{P0}$ for uncorroded rebar increases with decreasing rebar depth. At the same time it can also verify that the condition of initial rebars is acceptable post concrete pour and subsequently be used to monitor the status of rebars within concrete structures directly and isolate the condition of the rebars in each direction discretely.

Figure 31B:
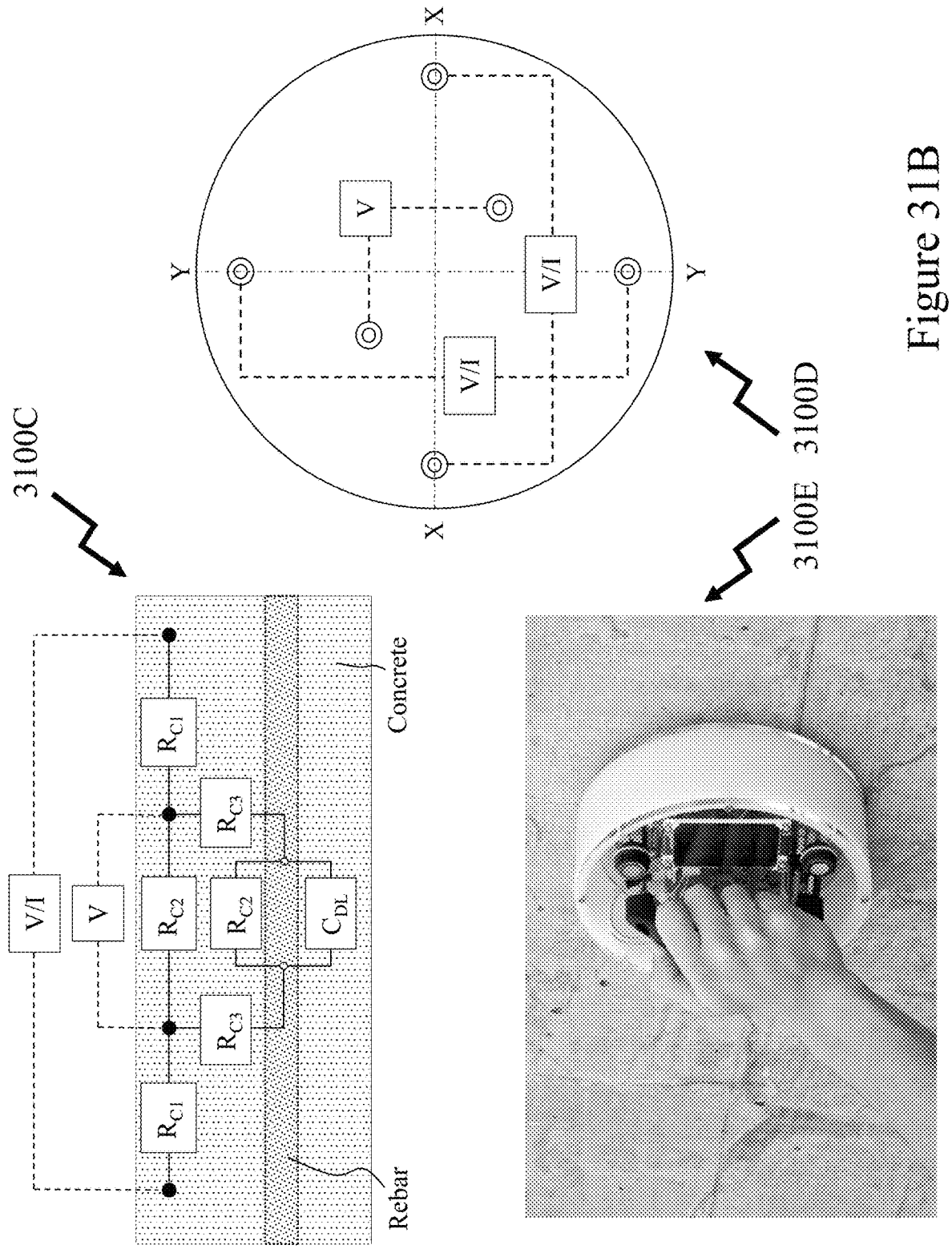
FIG. 31B depicts equivalent electrical circuit and hand held test instrument for extracting characteristics of a reinforced concrete system.

It would also be evident to one skilled in the art that such a DC 4-probe measurement technique may form part of an embedded sensor for corrosion monitoring as well as for periodic manual based monitoring. Referring to FIG. 31B there is depicted in first to third images 3100C to 3100D respectively a handheld non-contact corrosion detector instrument according to an embodiment of the invention. As depicted in first image 3100C different electrical characteristics of the reinforced concrete system can be extracted using a 6-point probe established by the inventors. As depicted in second image 3100D a pair of measurement contacts allow measurement of a voltage, V, to the concrete surface wherein the measurements are made by a first pair of excitation contacts aligned at 45° to the inner contacts and a second pair of excitation contacts aligned at −45° to the inner contacts such that the first and second pairs of excitation contacts are orthogonal to each other and offset at 45° relative to the inner contacts. A prototype instrument of such configuration is depicted in third image 3100E.

Then as evident from the equivalent electrical circuit in first image 3100C the following can be determined:

Polarization resistance of rebar (charge transfer resistance) ($R_P$): This parameter is related to the corrosion rate of rebar in concrete allowing the corrosion rate to be calculated from $R_P$ using $i_{COR} = B/(A \cdot R_P)$ Double layer capacitance ($C_{DL}$): The extent or severity of corrosion can be calculated from this parameter.

Electrical resistance of concrete ($R_{C1}$, $R_{C2}$): The intrinsic electrical resistivity of concrete can be calculated from these two parameters. The effect of the rebar would be excluded in the measurement using this approach according to embodiments of the invention which cannot be done with prior art AC measurement techniques.

Electrical resistance of concrete cover ($R_{C3}$): The relative value of this parameter with respect to $R_{C1}$ and $R_{C2}$ may be used to estimate the cover thickness of concrete.

Accordingly, using the novel configuration depicted in second image 3100D the inventors have established an instrument that allows the corrosion measurements on rebars along the X and Y directions to be performed separately. Also in this design, we use only two inner probes for the voltage measurement in both directions. Using this arrangement, only the direction of applied current or voltage on the external electrodes will be switched between the X and Y directions. In the other words, the same inner probes are used for the voltage measurement for both directions modified based on the 4-probe method.

6. Portable/Mobile Data Collection System

Within embodiments of the invention described supra a portable/mobile data collection system has been primarily described with respect to a vehicle, e.g. a car, van, truck, articulated truck, tractor-trailer, etc. However, it would be evident that such a portable/mobile data collection system may also be configured in other embodiments of the invention(s) to be mounted to a motorcycle, cycle, cart, golf buggy, etc. as well as a backpack, body pack, etc. for use by an individual.

7. In-Situ Concrete Testing

As discussed and described supra in respect of embodiments of the invention electrical measurements in-situ on concrete can provide information relating to cured concrete performance when made upon "wet" concrete and lifetime performance when made periodically subsequently. Accordingly, it would be beneficial to provide construction companies, builders, etc. with a test configuration that allowed for both of these to be performed without significant additional effort, expenditure or disruption. Now referring to FIG. 33 there is depicted a concrete assessment assembly (CONCAA) 3300A there is depicted an embodiment of such a test configuration. As depicted the CONCAA 3300A comprises a tube 3340 having internal diameter of 150 mm (6"), for example, and depth of 300 mm (12"). This tube 3340 is disposed within a structure prior to pouring with rods 3330 mounted within holder 3320 that fits onto the upper surface of the tube 3340. As such during the pour the concrete wells up within the tube 3340 surrounding the rods 3330.

Figure 33:
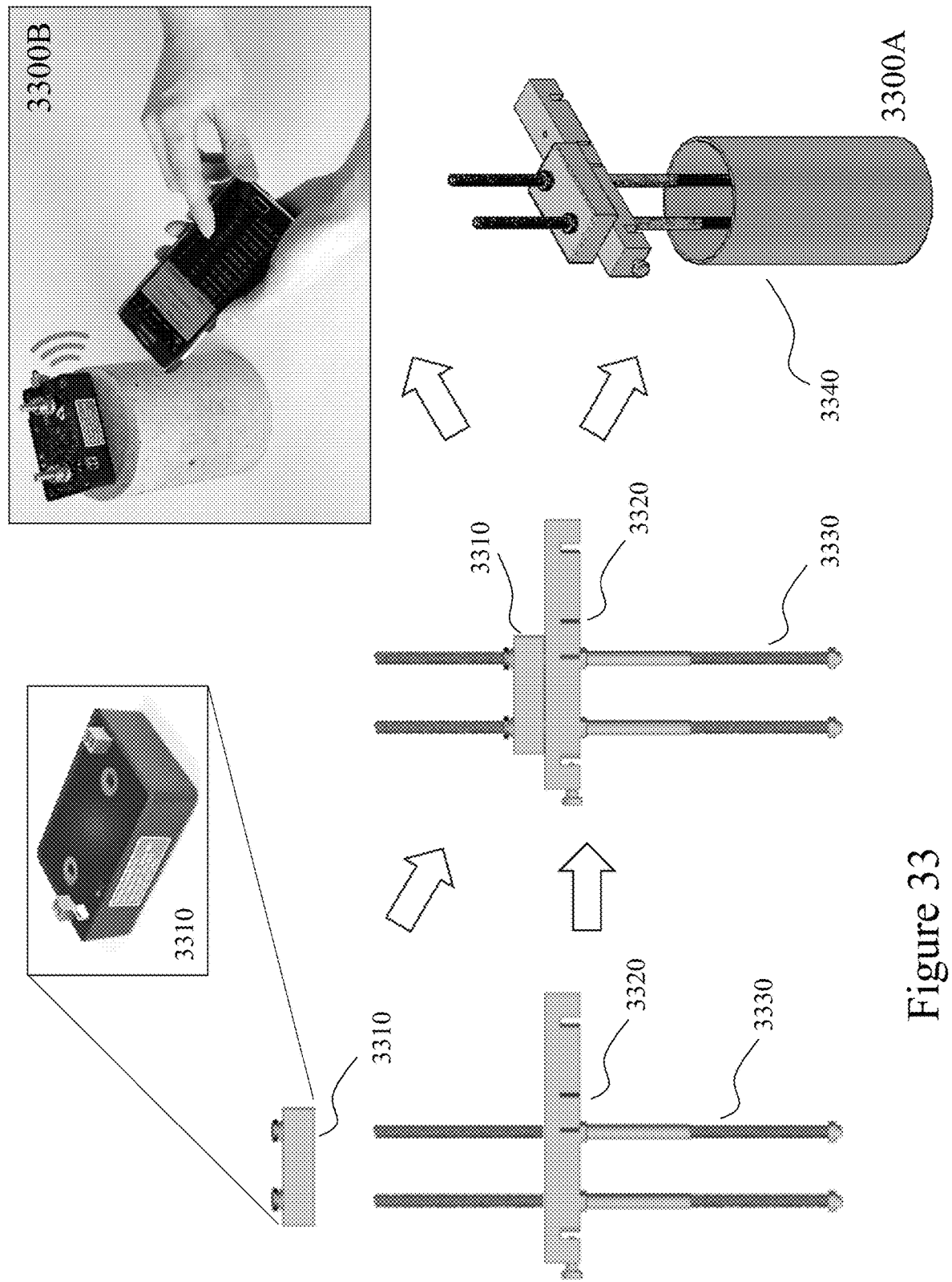
FIG. 33 depicts modular test assembly according to an embodiment of the invention for measuring concrete during its initial curing and subsequent lifetime of the concrete structure.

During the initial post-pour stage a tester 3310 is fitted to the upper exposed portions of the rods 3330 and retained in position with nuts on the threaded rods 3330. The tester 3310 then monitors the electrical parameters of the circuit formed between itself, the pair of rods 3330 and the concrete which is now curing. Subsequently, the recorded data from the tester 3310 can be retrieved, for example, wirelessly via a PED such as depicted in image 3300B. At some predetermined point later the tester 3310 can be removed and a protective cap applied to the CONCAA 3300A. This may be determined from a protocol established in dependence upon the electrical characteristic evolution such as described and depicted supra in respect of FIGS. 4 to 9B respectively. The testers 3310 can then be applied to a subsequent pour and/or be re-positioned periodically to perform ongoing concrete assessment. In the latter scenario the test engineer visits the site, for example, places the testers 3310 onto the CONCAA 3300A for a predetermined period of time before the measurements are retrieved from the testers 3310 and employed to define the properties of the concrete. This as depicted in FIG. 33 be via a wireless interrogation of the tester 3310 but it may alternatively be via a wired connection such that the reader, e.g. a smartphone or tablet, is connected to the CONCAA 3300A via a cable and connector or optical communications link.

8. Smart Concrete

It would be evident to one skilled in the art that the techniques, methodologies, etc. described supra in respect of FIGS. 4 to 9B, 31, and 33 are directed to lifetime characterization of concrete either from the viewpoint of the characterization of fresh concrete properties through to lifetime monitoring. Even assemblies such as CONCAA 3300A require that the construction team are provided with a detailed plan denoting where and when they are to be employed within the construction project. However, even these measurements whilst advancing the data and information available to the construction team, architect, quality management, surveyor, regulatory authority etc. have limitations with respect to the number that can be used, their locations, etc. and the fact that the measurements taken may require detailed data such as a maturity calibration curve from the concrete producer. Further, an essential portion of the "chain" is still not captured and accordingly pre-acceptance testing of the concrete may still be necessary prior to its being poured at the site.

Figure 34:
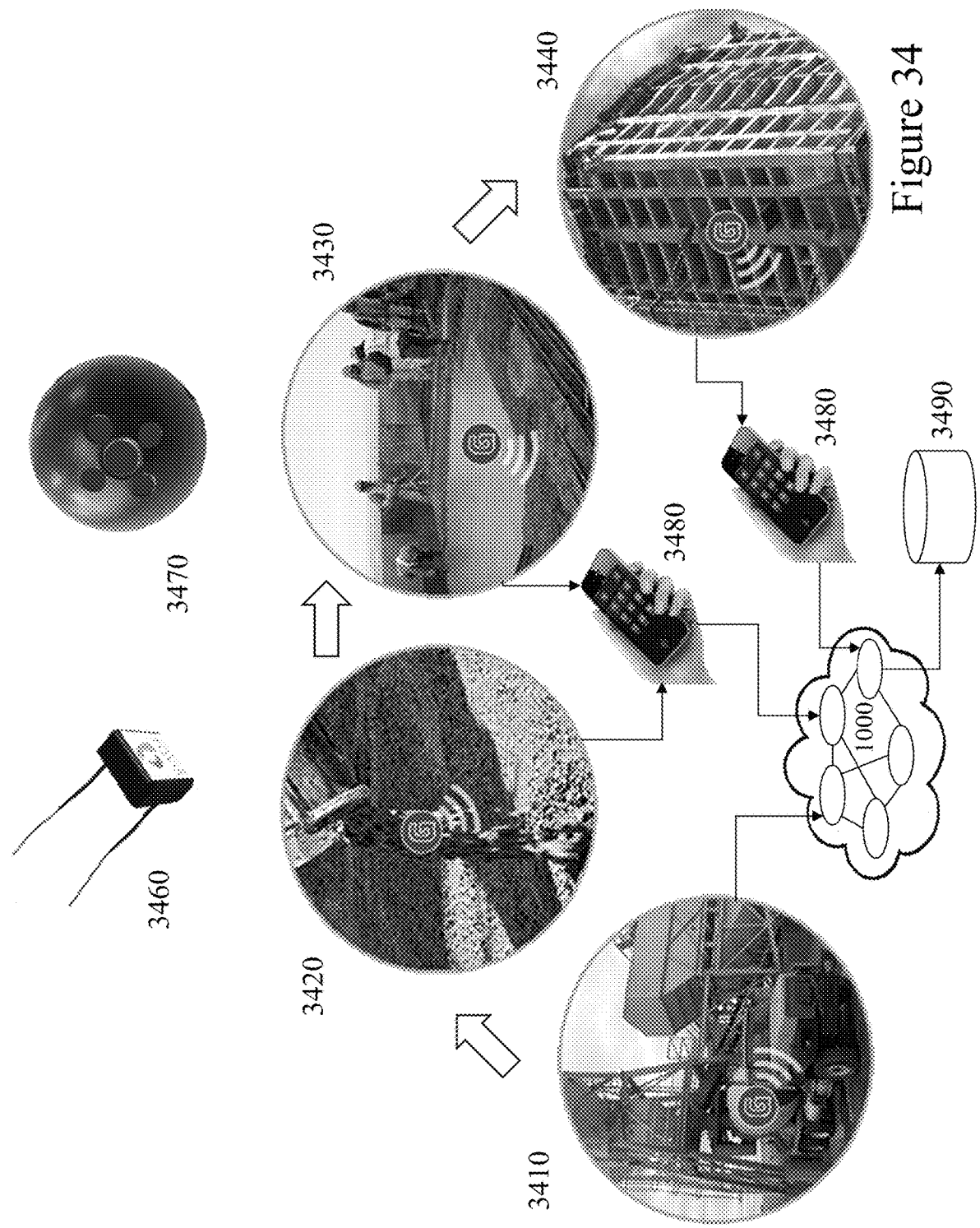
FIG. 34 depicts an embedded sensor methodology for data logging concrete properties from initial mix through pouring, curing, and subsequently according to an embodiment of the invention.

Accordingly, the inventors have established a methodology exploiting "embedded sensors" or what the inventors refer to as "smart rocks." As such these embedded sensors, such as depicted in prototype 3460 and production concept form 3470 in FIG. 34, are added to the concrete batch loaded onto the concrete truck at the batching plant. It is therefore possible to "tag", i.e. load into, the embedded sensor information relevant to the mix as well as delivery data etc. This information as well as other measurements made by the embedded sensors during the transportation, pouring, and placement can be accessed by wireless interface by the end user once the concrete is delivered to the construction site, as it is poured, and during its curing, maturation processes.

As such the tagging of the embedded sensors may include, but not be limited to, information such as batch identity, truck identity, date, time, location, batch mix parameters, etc. but also importantly information such as the maturity calibration curves for the mix established by the manufacturer. Accordingly, depending upon the degree of complexity embedded into the embedded sensor such data may be either retrieved for remote storage and subsequent use or it may be part of the embedded sensors processing of electrical measurement data such that calibration data of the concrete mix is already factored into the data provided by the embedded sensors. Accordingly, the embedded sensors, such as prototype 3460 and production concept form 3470 may be added to the concrete at the batching point 3410 either tagged already or tagged during loading. Subsequently upon delivery and pouring 3420 the embedded sensors may be read for information regarding the delivery process etc.

Once poured the embedded sensors may be read for curing information 3430 and then subsequently, depending upon the battery—power consumption etc., periodically read for lifetime data 3440 of the concrete. In each instance the acquired data may be acquired wirelessly and then pushed through network 1000 to one or more servers 3490. For devices wireless interrogating the embedded sensors these may be executing a software application which presents to the user concrete parameter data either as provided from the embedded sensor(s) directly using the calibration curves stored within or upon the device using calibration curve data stored within the embedded sensor but not processed by it, stored within the device or retrieved from the data stored upon the remote server 3490.

As depicted prototype sensor 3460 is enabled when an electrical circuit is completed via the flying leads. In production concept form 3470 the sensor may be enabled through a wireless signal, a vibration exceeding a threshold, via an electrical circuit being completed, etc. Accordingly, the embodiments of the invention support tagging the sensors and embedding the maturity calibration curves in the sensor. These curves are mix-specific and depending on the temperature history of the concrete can be used to estimate the strength of concrete. By embedded them within the sensors and the sensors employing this data the concrete manufacturer does not need to release commercially sensitive information such as their proprietary mix and calibration curves.

Based upon the combination of embedded sensors within the concrete mix in "smart rocks" with wireless interrogation and mobile/cloud based software applications other technical enhancements may be implemented, including for example:

- Weather forecast API, such that the ambient temperature prediction in conjunction with current concrete data can be used to predict/project the strength identifying quality problems earlier;
- Automatic detection of concrete pouring time, e.g. from electrical connection once the concrete is poured or change in the pressure, etc.;
- Tagging the sensor using NFC with smartphone;
- Data integrity and management on remote servers;
- Push notifications, such as for example the formwork company is notified when is the time to remove the formwork based upon actual concrete curing data; and
- Heat optimization wherein for example closed loop feedback of the temperature history and strength development can be employed to optimize heating employed in cold climates to ensure the concrete slabs gain sufficient strength within a specific period.

In addition to measuring, for example, temperature, DC electrical conductivity, and AC electrical conductivity it would be evident that additional parameters as discussed and described supra in respect of embodiments of the invention may be measured and monitored, including, but not limited to, concrete moisture content, concrete internal relative humidity, concrete pH, concrete mixture consistency, concrete workability (slump), and concrete air content.

Figure 35:
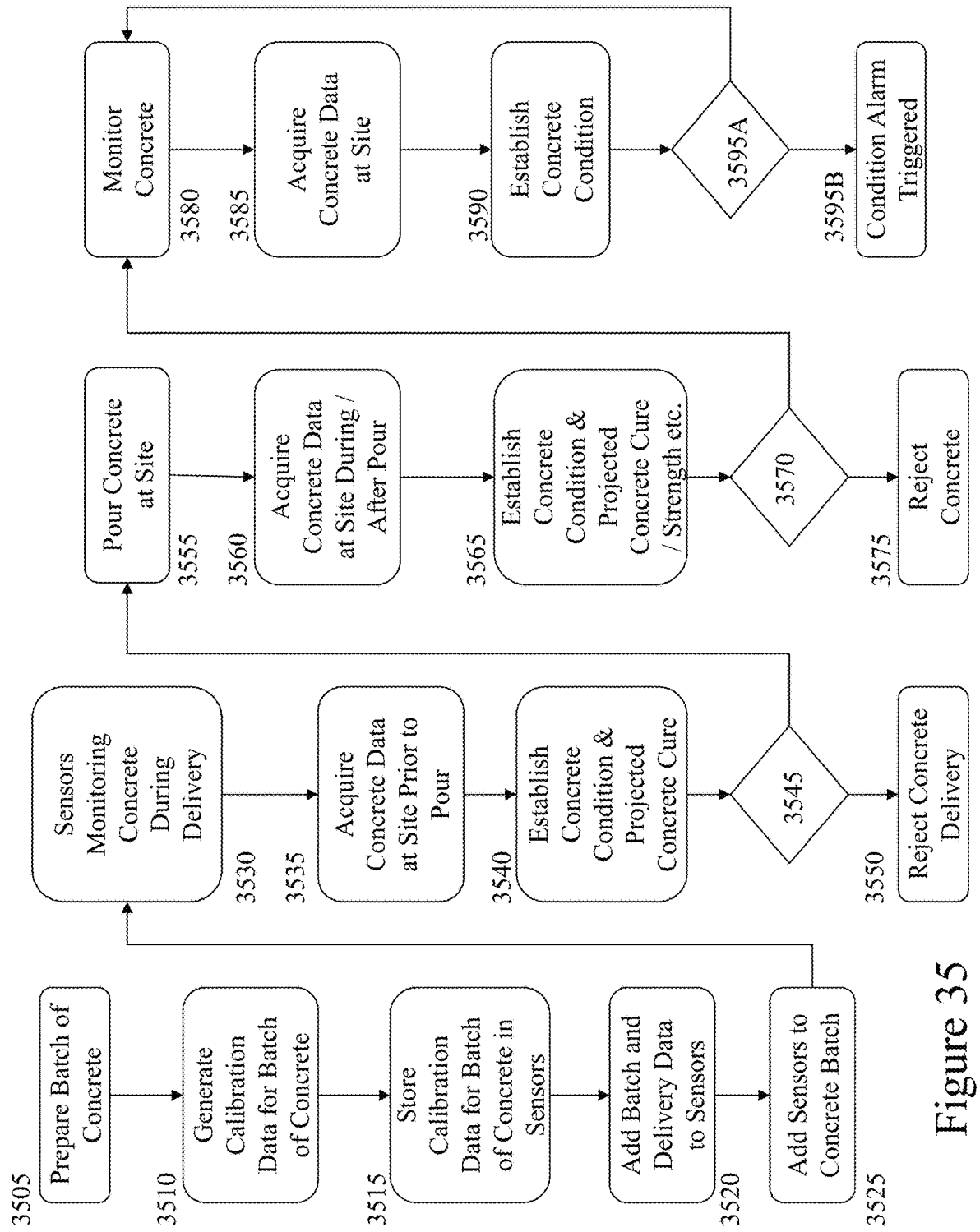
FIG. 35 depicts an exemplary process flow for an embedded sensor methodology for data logging concrete properties from initial mix through pouring, curing, and subsequently according to an embodiment of the invention.

Now referring to FIG. 35 there is depicted an exemplary flow for embedded sensor methodology for data logging concrete properties from initial mix through pouring, curing, and subsequently according to an embodiment of the invention. Accordingly, the process begins with step 3505 wherein a batch of concrete is prepared wherein in step 3510 the calibration data, for example the maturity calibration curves, is generated for that batch. Next in step 3515 this calibration data is stored within a batch of sensors which will be embedded with the concrete mix. Subsequently, in step 3520 additional data such as date, time, location, delivery identity, order data, manufacturer identity, etc. Once the sensors have been embedded with the data then they are mixed/embedded into the concrete for delivery.

Accordingly, the now embedded sensors monitor the concrete during the delivery—transportation sequence in step 3330 wherein at the site the current data is retrieved from the embedded sensors in step 3535 wherein this is employed to establish current concrete condition and projected cure in step 3540 wherein a delivery accept/reject decision is made in step 3545 wherein a rejection leads to step 3550 otherwise the process proceeds to step 3555 wherein the concrete is poured on site and the embedded sensors continue monitoring. Next in step 3560 the data from the sensors is retrieved either in a single retrieval event or multiple events such that in step 3565 the concrete condition, projected cure, projected strength, etc. are established. Next in step 3570 a decision on the concrete pour is made as to whether it will be allowed to continue curing or whether there is a problem and remedial work/tear-down etc. are required at which the process proceeds to step 3575 and terminates or proceeds to step 3580.

In step 3580 the embedded sensors continue monitoring the concrete but now for longer term characteristics as the cure has been passed at step 3570. Subsequently the embedded sensor data is acquired in step 3585 and used in step 3590 to establish the concrete's condition. If everything is within defined boundaries then the process proceeds from a decision step 3595A to loop otherwise it proceeds to step 3595B and an alarm is triggered with respect to the condition of the concrete. In this manner the life cycle of the concrete can be tracked with the embedded sensors.

Optionally, to provide extended lifetime of the embedded sensors their initial sampling rate during activation, transport, pour and curing may be amended to an increased period between sampling points wherein, for example, after a first predetermined period (e.g. 1 week) the sampling drops to a lower rate, then again at predetermined points either time based or concrete cure derived such that, for example, sampling drops to hourly, daily etc. to provide extended battery life. Alternatively, the embedded sensors may be designed for specific short life cycle for the initial portion of the concrete life cycle after which other methods are employed such as described supra in respect of FIGS. 31A and 31B for example.

Accordingly, data regarding the curing of a concrete structure throughout its structure may be derived rather than from a limited number of sampling points or concrete tests on delivered concrete. For example, the number of embedded sensors may be established as 1 per cubic meter, 1 per 2 cubic meter, 1 per 8 cubic meter, 4 per truck irrespective of load, etc. The number may be varied in accordance with concrete mix, architect schedule so that sensitive load bearing structures are more accurately plotted than others.

Whilst the embedded sensors have been described with respect to their use within concrete it would be apparent that variants may be employed within other materials in order to monitor, log, track, and verify aspects of their transport, delivery, and use.

Embedded sensors according to embodiments of the invention may be formed from a variety of materials include, but not limited, to metals, ceramics, plastics, resins, and rubbers according to the requirements for compatibility with the concrete, lifetime, crush resistance etc. Optionally, the embedded sensors may be hollow or solid with cavities for electronics/battery etc. Optionally, the embedded sensor may comprise a plurality of metallic elements isolated with respect to each other to form electrical connections between the electronics within the embedded sensor and the concrete.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor and may vary in implementation where the memory is employed in storing software codes for subsequent execution to that when the memory is employed in executing the software codes. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

The methodologies described herein are, in one or more embodiments, performable by a machine which includes one or more processors that accept code segments containing instructions. For any of the methods described herein, when the instructions are executed by the machine, the machine performs the method. Any machine capable of executing a set of instructions (sequential or otherwise) that specify actions to be taken by that machine are included. Thus, a typical machine may be exemplified by a typical processing system that includes one or more processors. Each processor may include one or more of a CPU, a graphics-processing unit, and a programmable DSP unit. The processing system further may include a memory subsystem including main RAM and/or a static RAM, and/or ROM. A bus subsystem may be included for communicating between the components. If the processing system requires a display, such a display may be included, e.g., a liquid crystal display (LCD). If manual data entry is required, the processing system also includes an input device such as one or more of an alphanumeric input unit such as a keyboard, a pointing control device such as a mouse, and so forth.

The memory includes machine-readable code segments (e.g. software or software code) including instructions for performing, when executed by the processing system, one of more of the methods described herein. The software may reside entirely in the memory, or may also reside, completely or at least partially, within the RAM and/or within the processor during execution thereof by the computer system. Thus, the memory and the processor also constitute a system comprising machine-readable code.

In alternative embodiments, the machine operates as a standalone device or may be connected, e.g., networked to other machines, in a networked deployment, the machine may operate in the capacity of a server or a client machine in server-client network environment, or as a peer machine in a peer-to-peer or distributed network environment. The machine may be, for example, a computer, a server, a cluster of servers, a cluster of computers, a web appliance, a distributed computing environment, a cloud computing environment, or any machine capable of executing a set of instructions (sequential or otherwise) that specify actions to be taken by that machine. The term "machine" may also be taken to include any collection of machines that individually or jointly execute a set (or multiple sets) of instructions to perform any one or more of the methodologies discussed herein.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A self-contained device comprising:
a shell comprising an outer surface and an interior;
an electrical circuit disposed within the shell and comprising a battery, a wireless transceiver operating according to a predetermined wireless protocol, a memory, and a microprocessor; and
a measurement circuit coupled to the microprocessor disposed within the shell and providing a predetermined electrical measurement of a characteristic of an environment; wherein
the environment is a predetermined material that the self-contained device is at least one of embedded within and will be embedded within;
the predetermined electrical measurement is an electrical impedance measurement;
the predetermined electrical measurement is adjusted in dependence upon a temperature established by the self-contained device at the time of the predetermined electrical measurement; wherein
the adjustment is performed in dependence upon an activation energy of a plurality of activation energies;
each activation energy of the plurality of activation energies relates to a different characteristic of the environment; and
the activation energy of the plurality of activation energies is determined in dependence upon the characteristic of the environment being determined.

2. The self-contained device according to claim 1, wherein
the microprocessor receives via the wireless transceiver and stores within the memory maturity calibration data comprising maturity calibration curves relating to a batch of the predetermined material;
the maturity calibration data relates to at least the predetermined electrical measurement of the characteristic of the environment; and
the maturity calibration data is employed by the microprocessor in generating the characteristic of the environment from the predetermined electrical measurement of the characteristic of the environment.

3. The self-contained device according to claim 1, wherein
the memory comprises maturity calibration data comprising maturity calibration curves relating to a batch of the predetermined material generated by a manufacturer of the batch of the predetermined material; and
the device transmits to a second wireless transceiver operating according to the predetermined wireless protocol data comprising at least one of:
the characteristic of the environment generated in dependence upon the maturity calibration data and the predetermined electrical measurement of the characteristic of the environment; and
the predetermined electrical measurement of the characteristic of the environment and the maturity calibration data stored within the memory.

4. The self-contained device according to claim 1, wherein
the shell comprises a pair of metallic elements isolated from each other via an insulating material;
an electrical circuit within the device is completed when the pair of metallic elements are in contact with the environment; and
the device is either turned on or transitioned from a sleep mode to an active mode when the electrical circuit has a resistance below a predetermined threshold resistance value.

5. The self-contained device according to claim 1, wherein
the microprocessor stores data received via the wireless transceiver into the memory; wherein
the data received and stored relates to at least one of:
an identity of a vehicle delivering the material to a worksite; and
batch mix parameters of the material.

6. The self-contained device according to claim 1, further comprising
a sensor connected to at least one of the microprocessor and measurement circuit;
wherein
the sensor relates to at least one of:
a relative humidity of the predetermined material;
a consistency of the predetermined material;
a measure of workability of the predetermined material;
a strength of the predetermined material;
a degradation of the predetermined material; and
an air content of the predetermined material.

7. The self-contained device according to claim 1, wherein
the memory stores computer executable instructions for execution by the microprocessor; and
the computer executable instructions when executed by the microprocessor configure the self-contained device to execute a process comprising:
receive a set of calibration data comprising maturity calibration curves from an external source via the wireless transceiver;
store the set of calibration data within the memory;
periodically perform the predetermined electrical measurement;
automatically generate the characteristic of the environment from the predetermined electrical measurement of the characteristic of the environment in dependence upon the stored set of calibration data; and
store the characteristic of the environment within the memory;
the set of calibration data relates to the characteristic of the environment; and
the set of calibration data relates to a batch of the environment and is generated by a manufacturer of the batch of the environment.

8. The self-contained device according to claim 1, wherein
the memory stores computer executable instructions for execution by the microprocessor; and
the computer executable instructions when executed by the microprocessor configure the self-contained device to execute a process comprising:
receive a set of calibration data comprising maturity calibration curves from an external source via the wireless transceiver;
store the set of calibration data within the memory;
periodically perform the predetermined electrical measurement;
automatically generate the characteristic of the environment from the predetermined electrical measurement of the characteristic of the environment in dependence upon the stored set of calibration data; and store the characteristic of the environment within the memory;

the set of calibration data relates to the characteristic of the environment;

the set of calibration data relates to a batch of the environment and is generated by a manufacturer of the batch of the environment;

the predetermined material is concrete; and the characteristic of the environment is one of:
the in-situ compressive strength;
a prediction of at least one of 7-day, 28-day and 56-day compressive strength; and
a value of a transport property of the predetermined material selected from the group comprising permeability, diffusivity and porosity.

9. The self-contained device according to claim 1, wherein the memory stores computer executable instructions for execution by the microprocessor; and the computer executable instructions when executed by the microprocessor configure the self-contained device to execute a process comprising:
receive a set of calibration data comprising maturity calibration curves from an external source via the wireless transceiver;
store the set of calibration data within the memory;
periodically perform the predetermined electrical measurement;
automatically generate the characteristic of the environment from the predetermined electrical measurement of the characteristic of the environment in dependence upon the stored set of calibration data; and
store the characteristic of the environment within the memory;

the set of calibration data relates to the characteristic of the environment;

the set of calibration data relates to a batch of the environment and is generated by a manufacturer of the batch of the environment, the predetermined material is concrete; and the characteristic of the environment is one of:
determination of an initial setting time of the predetermined material; and
determination of a final setting time of the predetermined material.

10. The self-contained device according to claim 1, wherein the memory stores computer executable instructions for execution by the microprocessor; and the computer executable instructions when executed by the microprocessor configure the self-contained device to execute a process comprising:
receive a set of calibration data comprising maturity calibration curves from an external source via the wireless transceiver; and
store the set of calibration data within the memory;

the set of calibration data relates to the characteristic of the environment; and the set of calibration data relates to a batch of the environment and is generated by a manufacturer of the batch of the environment.

11. The self-contained device according to claim 1, wherein the memory stores:
computer executable instructions for execution by the microprocessor; and
a set of calibration data comprising maturity calibration curves;

the computer executable instructions when executed by the microprocessor configure the self-contained device to execute a process comprising:
acquire from the measurement circuit the predetermined electrical measurement of a characteristic of an environment;
automatically generate the characteristic of the environment using the predetermined electrical measurement of the characteristic of the environment and the stored set of calibration data; and
transmit the generated characteristic of the environment to a second wireless transceiver operating according to the predetermined wireless protocol;

the set of calibration data relates to the characteristic of the environment; and the set of calibration data relates to a batch of the environment and is generated by a manufacturer of the batch of the environment.

12. The self-contained device according to claim 1, wherein the memory stores computer executable instructions for execution by the microprocessor;

the computer executable instructions when executed by the microprocessor configure the self-contained device to execute a process comprising:
acquire for a plurality of time periods a plurality of measurements from the measurement circuit the predetermined electrical measurement of a characteristic of an environment;
store each measurement of the plurality of measurements within the memory;

a periodicity of the measurements is determined in dependence upon a period of the plurality of time periods;

a first time period of the plurality of time periods is from initial activation of the self-contained device and has a first predetermined length of time;

each subsequent time period of the plurality of time periods is from the end of a preceding time period of the plurality of time periods; and each subsequent time period of the plurality of time periods has a predetermined length of time.

13. The self-contained device according to claim 1, wherein the memory stores:
computer executable instructions for execution by the microprocessor; and
a set of calibration data comprising maturity calibration curves;

the computer executable instructions when executed by the microprocessor configure the self-contained device to execute a process comprising:
acquire for a plurality of time periods a plurality of measurements from the measurement circuit the predetermined electrical measurement of a characteristic of an environment;
automatically generate the characteristic of the environment for each measurement of the plurality of measurements in dependence upon the stored set of calibration data; and store the generated characteristic of the environment for each measurement of the plurality of measurements within the memory;
a periodicity of the measurements is determined in dependence upon a period of the plurality of time periods;
a first time period of the plurality of time periods is from initial activation of the self-contained device and has a first predetermined length of time;
each subsequent time period of the plurality of time periods is from the end of a preceding time period of the plurality of time periods; and
each subsequent time period of the plurality of time periods continues until a predetermined condition with respect to the generated characteristic of the environment is met.

14. The self-contained device according to claim 1, wherein
the memory stores computer executable instructions for execution by the microprocessor; and
the computer executable instructions when executed by the microprocessor configure the self-contained device to execute a process comprising:
receive a set of first data from an external source of a plurality of external sources via the wireless transceiver;
store the set of first data within the memory;
receive a plurality of sets of second data, each set of second data from a predetermined external source of the plurality of external sources; and
store the plurality of sets of second data within the memory;
the set of first data relates to at least one of:
a batch identity defining a batch of the predetermined material that the self-contained device is at least one of embedded within and will be embedded within;
an identity of a vehicle delivering the predetermined material that the self-contained device is at least one of embedded within and will be embedded within; and
batch mix parameters of the predetermined material that the self-contained device is at least one of embedded within and will be embedded within; and
each set of second data of the plurality of second sets of data relates to at least one of a time and a geographical location associated with an event relating to the predetermined material that the self-contained device is embedded within.

15. The self-contained device according to claim 1, wherein
the memory stores computer executable instructions for execution by the microprocessor; and
the computer executable instructions when executed by the microprocessor configure the self-contained device to execute a process comprising:
receive a set of calibration data comprising maturity calibration curves from an external source via the wireless transceiver; and
store the set of calibration data within the memory; and
the set of calibration data relates to the characteristic of the environment.

16. The self-contained device according to claim 1, wherein
the memory stores:
computer executable instructions for execution by the microprocessor; and
a set of calibration data comprising maturity calibration curves;
the computer executable instructions when executed by the microprocessor configure the self-contained device to execute a process comprising:
acquire from the measurement circuit a plurality of raw measurements, each raw measurement comprising a predetermined electrical measurement of a characteristic of an environment;
store the plurality of raw measurements within the memory;
automatically generate a plurality of processed measurements, each processed measurement comprising the characteristic of the environment established in dependence upon a raw measurement of the plurality of raw measurements and the stored set of calibration data;
store the plurality of processed measurements within the memory;
transmit the plurality of raw measurements to a second wireless transceiver operating according to the predetermined wireless protocol; and
transmit the plurality of processed measurements to the second wireless transceiver; and
the set of calibration data relates to the characteristic of the environment.

17. The self-contained device according to claim 1, wherein
the memory stores computer executable instructions for execution by the microprocessor; and
the computer executable instructions when executed by the microprocessor configure the self-contained device to execute a process comprising:
receive a set of calibration data comprising maturity calibration curves from an external source via the wireless transceiver; and
store the set of calibration data within the memory;
the set of calibration data relates to the characteristic of the environment; and
the set of calibration data relates to a batch of the environment and is generated by a manufacturer of the batch of the environment; and
the external source transmits the set of calibration data to the self-contained device at least one of prior to the self-contained device being added to the predetermined material or at the point the self-contained device is added to the predetermined material.

18. The self-contained device according to claim 1, wherein
the self-contained device further comprises a temperature sensor in communication with the microprocessor;
the memory stores computer executable instructions for execution by the microprocessor which when executed by the microprocessor configure the self-contained device to execute a process comprising:
acquire from the measurement circuit a plurality of measurements of the predetermined electrical measurement of a characteristic of an environment;
acquire from the temperature sensor a plurality of temperature measurements, each temperature measurement of the plurality of temperature measurements obtained at the time that a measurement of the plurality of measurements was acquired; and
transmit the plurality of measurements and the plurality of temperature measurements to a device comprising a second wireless transceiver operating according to the predetermined wireless protocol and therein from the device to a remote server for processing;

the environment is a predetermined material that the self-contained device is at least one of embedded within and will be embedded within; and the remote server generates a projection of a strength of the predetermined material in dependence upon the plurality of measurements acquired from the self-contained device, the plurality of temperature measurements acquired from the self-contained device, and an ambient temperature prediction for a location of the self-contained sensor established through a weather forecast application programming interface.

19. The self-contained device according to claim 1, wherein the self-contained device further comprises a temperature sensor in communication with the microprocessor;

the memory stores computer executable instructions for execution by the microprocessor which when executed by the microprocessor configure the self-contained device to execute a process comprising:

receive a set of calibration data comprising maturity calibration curves from an external source via the wireless transceiver; and store the set of calibration data within the memory;

acquire from the measurement circuit a plurality of raw measurements, each raw measurement being a predetermined electrical measurement of the characteristic of an environment;

acquire from the temperature sensor a plurality of temperature measurements, each temperature measurement of the plurality of temperature measurements obtained at the time that a raw measurement of the plurality of raw measurements was acquired;

automatically generate a plurality of processed measurements, each processed measurement comprising the characteristic of the environment established in dependence upon a raw measurement of the plurality of raw measurements, the temperature measurement of the plurality of temperature measurements acquired at when the raw measurement of the plurality of raw measurements was acquired; and the stored set of calibration data;

store the plurality of processed measurements within the memory; and transmit data to a device comprising a second wireless transceiver operating according to the predetermined wireless protocol;

the environment is a predetermined material that the self-contained device is at least one of embedded within and will be embedded within;

the data is at least one:
the plurality of processed measurements; and
the set of calibration data, the plurality of raw measurements, and the plurality of temperature measurements; and the device at least one of:
generates a push notification to a predetermined third party upon determining a predetermined criteria with respect to the data either of directly or in dependence upon processing the data has been met; and
employs the data either directly or in dependence upon processing the data for closed loop feedback of a heating system associated with the predetermined material.

20. The self-contained device according to claim 1, wherein the self-contained device further comprises a temperature sensor in communication with the microprocessor;

the memory stores computer executable instructions for execution by the microprocessor which when executed by the microprocessor configure the self-contained device to execute a process comprising:

receive a set of calibration data comprising maturity calibration curves from an external source via the wireless transceiver; and store the set of calibration data within the memory;

acquire from the measurement circuit a plurality of raw measurements, each raw measurement being a predetermined electrical measurement of the characteristic of an environment;

acquire from the temperature sensor a plurality of temperature measurements, each temperature measurement of the plurality of temperature measurements obtained at the time that a raw measurement of the plurality of raw measurements was acquired;

automatically generate a plurality of processed measurements, each processed measurement comprising the characteristic of the environment established in dependence upon a raw measurement of the plurality of raw measurements, the temperature measurement of the plurality of temperature measurements acquired at when the raw measurement of the plurality of raw measurements was acquired; and the stored set of calibration data;

store the plurality of processed measurements within the memory; and transmit data to a device comprising a second wireless transceiver operating according to the predetermined wireless protocol;

the environment is a predetermined material that the self-contained device is at least one of embedded within and will be embedded within;

the data is at least one:
the plurality of processed measurements; and
the set of calibration data, the plurality of raw measurements, and the plurality of temperature measurements; and the device establishes an accept/reject decision with respect to the predetermined material in dependence upon the either of directly or in dependence upon processing the data.

21. A self-contained device comprising:
a shell comprising an outer surface and an interior;
an electrical circuit disposed within the shell and comprising a battery, a wireless transceiver operating according to a predetermined wireless protocol, a memory, and a microprocessor; and
a measurement circuit coupled to the microprocessor disposed within the shell and providing a predetermined electrical measurement of a characteristic of an environment; wherein the environment is a predetermined material that the self-contained device is at least one of embedded within and will be embedded within;

the memory stores computer executable instructions for execution by the microprocessor;

the computer executable instructions when executed by the microprocessor configure the self-contained device to execute a process comprising:

receive a set of calibration data comprising maturity calibration curves from an external source via the wireless transceiver;

store the set of calibration data within the memory;

periodically perform the predetermined electrical measurement;

automatically generate the characteristic of the environment from the predetermined electrical measurement of the characteristic of the environment in dependence upon the stored set of calibration data; and store the characteristic of the environment within the memory;

the set of calibration data relates to the characteristic of the environment;

the set of calibration data relates to a batch of the environment and is generated by a manufacturer of the batch of the environment, the predetermined material is concrete; and the characteristic of the environment is one of:
  determination of an initial setting time of the predetermined material; and
  determination of a final setting time of the predetermined material.

22. A self-contained device comprising:

a shell comprising an outer surface and an interior;

an electrical circuit disposed within the shell and comprising a battery, a wireless transceiver operating according to a predetermined wireless protocol, a memory, and a microprocessor; and a measurement circuit coupled to the microprocessor disposed within the shell and providing a predetermined electrical measurement of a characteristic of an environment; wherein the environment is a predetermined material that the self-contained device is at least one of embedded within and will be embedded within;

the memory stores computer executable instructions for execution by the microprocessor;

the computer executable instructions when executed by the microprocessor configure the self-contained device to execute a process comprising:
  acquire for a plurality of time periods a plurality of measurements from the measurement circuit the predetermined electrical measurement of a characteristic of an environment;
  store each measurement of the plurality of measurements within the memory;

a periodicity of the measurements is determined in dependence upon a period of the plurality of time periods;

a first time period of the plurality of time periods is from initial activation of the self-contained device and has a first predetermined length of time;

each subsequent time period of the plurality of time periods is from the end of a preceding time period of the plurality of time periods; and each subsequent time period of the plurality of time periods has a predetermined length of time.

23. A self-contained device comprising:

a shell comprising an outer surface and an interior;

an electrical circuit disposed within the shell and comprising a battery, a wireless transceiver operating according to a predetermined wireless protocol, a memory, and a microprocessor; and a measurement circuit coupled to the microprocessor disposed within the shell and providing a predetermined electrical measurement of a characteristic of an environment; wherein the environment is a predetermined material that the self-contained device is at least one of embedded within and will be embedded within;

the memory stores:
  computer executable instructions for execution by the microprocessor; and
  a set of calibration data comprising maturity calibration curves;

the computer executable instructions when executed by the microprocessor configure the self-contained device to execute a process comprising:
  acquire for a plurality of time periods a plurality of measurements from the measurement circuit the predetermined electrical measurement of a characteristic of an environment;
  automatically generate the characteristic of the environment for each measurement of the plurality of measurements in dependence upon the stored set of calibration data; and
  store the generated characteristic of the environment for each measurement of the plurality of measurements within the memory;

a periodicity of the measurements is determined in dependence upon a period of the plurality of time periods;

a first time period of the plurality of time periods is from initial activation of the self-contained device and has a first predetermined length of time;

each subsequent time period of the plurality of time periods is from the end of a preceding time period of the plurality of time periods; and each subsequent time period of the plurality of time periods continues until a predetermined condition with respect to the generated characteristic of the environment is met.

24. A self-contained device comprising:

a shell comprising an outer surface and an interior;

an electrical circuit disposed within the shell and comprising a battery, a wireless transceiver operating according to a predetermined wireless protocol, a memory, and a microprocessor; and a measurement circuit coupled to the microprocessor disposed within the shell and providing a predetermined electrical measurement of a characteristic of an environment; wherein the environment is a predetermined material that the self-contained device is at least one of embedded within and will be embedded within;

the memory stores computer executable instructions for execution by the microprocessor; and the computer executable instructions when executed by the microprocessor configure the self-contained device to execute a process comprising:
  receive a set of first data from an external source of a plurality of external sources via the wireless transceiver;
  store the set of first data within the memory;
  receive a plurality of sets of second data, each set of second data from a predetermined external source of the plurality of external sources; and
  store the plurality of sets of second data within the memory;

the set of first data relates to at least one of:
  a batch identity defining a batch of the predetermined material that the self-contained device is at least one of embedded within and will be embedded within;
  an identity of a vehicle delivering the predetermined material that the self-contained device is at least one of embedded within and will be embedded within; and batch mix parameters of the predetermined material that the self-contained device is at least one of embedded within and will be embedded within; and each set of second data of the plurality of second sets of data relates to at least one of a time and a geographical location associated with an event relating to the predetermined material that the self-contained device is embedded within.

25. A self-contained device comprising:

a shell comprising an outer surface and an interior;

an electrical circuit disposed within the shell and comprising a battery, a wireless transceiver operating according to a predetermined wireless protocol, a memory, and a microprocessor; and a measurement circuit coupled to the microprocessor disposed within the shell and providing a predetermined electrical measurement of a characteristic of an environment; wherein the environment is a predetermined material that the self-contained device is at least one of embedded within and will be embedded within;

the self-contained device further comprises a temperature sensor in communication with the microprocessor;

the memory stores computer executable instructions for execution by the microprocessor which when executed by the microprocessor configure the self-contained device to execute a process comprising:
  acquire from the measurement circuit a plurality of measurements of the predetermined electrical measurement of a characteristic of an environment;
  acquire from the temperature sensor a plurality of temperature measurements, each temperature measurement of the plurality of temperature measurements obtained at the time that a measurement of the plurality of measurements was acquired; and
  transmit the plurality of measurements and the plurality of temperature measurements to a device comprising a second wireless transceiver operating according to the predetermined wireless protocol and therein from the device to a remote server for processing;

the environment is a predetermined material that the self-contained device is at least one of embedded within and will be embedded within; and the remote server generates a projection of a strength of the predetermined material in dependence upon the plurality of measurements acquired from the self-contained device, the plurality of temperature measurements acquired from the self-contained device, and an ambient temperature prediction for a location of the self-contained sensor established through a weather forecast application programming interface.

26. A self-contained device comprising:

a shell comprising an outer surface and an interior;

an electrical circuit disposed within the shell and comprising a battery, a wireless transceiver operating according to a predetermined wireless protocol, a memory, and a microprocessor; and a measurement circuit coupled to the microprocessor disposed within the shell and providing a predetermined electrical measurement of a characteristic of an environment; wherein the environment is a predetermined material that the self-contained device is at least one of embedded within and will be embedded within;

the self-contained device further comprises a temperature sensor in communication with the microprocessor;

the memory stores computer executable instructions for execution by the microprocessor which when executed by the microprocessor configure the self-contained device to execute a process comprising:
  receive a set of calibration data comprising maturity calibration curves from an external source via the wireless transceiver; and
  store the set of calibration data within the memory;
  acquire from the measurement circuit a plurality of raw measurements, each raw measurement being a predetermined electrical measurement of the characteristic of an environment;
  acquire from the temperature sensor a plurality of temperature measurements, each temperature measurement of the plurality of temperature measurements obtained at the time that a raw measurement of the plurality of raw measurements was acquired;
  automatically generate a plurality of processed measurements, each processed measurement comprising the characteristic of the environment established in dependence upon a raw measurement of the plurality of raw measurements, the temperature measurement of the plurality of temperature measurements acquired at when the raw measurement of the plurality of raw measurements was acquired; and the stored set of calibration data;
  store the plurality of processed measurements within the memory; and
  transmit data to a device comprising a second wireless transceiver operating according to the predetermined wireless protocol;

the environment is a predetermined material that the self-contained device is at least one of embedded within and will be embedded within;

the data is at least one:
  the plurality of processed measurements; and
  the set of calibration data, the plurality of raw measurements, and the plurality of temperature measurements; and the device at least one of:
  generates a push notification to a predetermined third party upon determining a predetermined criteria with respect to the data either of directly or in dependence upon processing the data has been met; and
  employs the data either directly or in dependence upon processing the data for closed loop feedback of a heating system associated with the predetermined material.

27. A self-contained device comprising:

a shell comprising an outer surface and an interior;

an electrical circuit disposed within the shell and comprising a battery, a wireless transceiver operating according to a predetermined wireless protocol, a memory, and a microprocessor; and a measurement circuit coupled to the microprocessor disposed within the shell and providing a predetermined electrical measurement of a characteristic of an environment; wherein the environment is a predetermined material that the self-contained device is at least one of embedded within and will be embedded within;

the self-contained device further comprises a temperature sensor in communication with the microprocessor;

the memory stores computer executable instructions for execution by the microprocessor which when executed by the microprocessor configure the self-contained device to execute a process comprising:

receive a set of calibration data comprising maturity calibration curves from an external source via the wireless transceiver; and store the set of calibration data within the memory;

acquire from the measurement circuit a plurality of raw measurements, each raw measurement being a predetermined electrical measurement of the characteristic of an environment;

acquire from the temperature sensor a plurality of temperature measurements, each temperature measurement of the plurality of temperature measurements obtained at the time that a raw measurement of the plurality of raw measurements was acquired;

automatically generate a plurality of processed measurements, each processed measurement comprising the characteristic of the environment established in dependence upon a raw measurement of the plurality of raw measurements, the temperature measurement of the plurality of temperature measurements acquired at when the raw measurement of the plurality of raw measurements was acquired; and the stored set of calibration data;

store the plurality of processed measurements within the memory; and transmit data to a device comprising a second wireless transceiver operating according to the predetermined wireless protocol;

the environment is a predetermined material that the self-contained device is at least one of embedded within and will be embedded within;

the data is at least one:
  the plurality of processed measurements; and
  the set of calibration data, the plurality of raw measurements, and the plurality of temperature measurements; and the device establishes an accept/reject decision with respect to the predetermined material in dependence upon the either of directly or in dependence upon processing the data.

* * * * *